(12) United States Patent
Minn et al.

(10) Patent No.: US 10,183,914 B2
(45) Date of Patent: Jan. 22, 2019

(54) 2-AMINO-5-KETO-PYRIMIDINE DERIVATIVES AND THE USE THEREOF FOR CONTROLLING UNDESIRED PLANT GROWTH

(71) Applicant: BAYER CROPSCIENCE AKTIENGESELLSCHAFT, Duesseldorf (DE)

(72) Inventors: Klemens Minn, Hattersheim (DE); Hansjoerg Dietrich, Liederbach am Taunus (DE); Elmar Gatzweiler, Bad Nauheim (DE); Christopher Hugh Rosinger, Hofheim (DE); Dirk Schmutzler, Hattersheim (DE); Estella Buscató Arsequell, Frankfurt am Main (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/321,629

(22) PCT Filed: Jun. 29, 2015

(86) PCT No.: PCT/EP2015/064661
§ 371 (c)(1),
(2) Date: Dec. 22, 2016

(87) PCT Pub. No.: WO2016/001118
PCT Pub. Date: Jan. 7, 2016

(65) Prior Publication Data
US 2017/0158644 A1    Jun. 8, 2017

(30) Foreign Application Priority Data
Jul. 1, 2014 (EP) .................... 14175250

(51) Int. Cl.
| | | |
|---|---|---|
| *A01N 43/54* | (2006.01) | |
| *C07D 239/42* | (2006.01) | |
| *C07D 239/78* | (2006.01) | |
| *C07D 239/84* | (2006.01) | |
| *C07D 405/12* | (2006.01) | |

(52) U.S. Cl.
CPC ........... *C07D 239/42* (2013.01); *A01N 43/54* (2013.01); *C07D 239/78* (2013.01); *C07D 239/84* (2013.01); *C07D 405/12* (2013.01)

(58) Field of Classification Search
CPC .. C07D 405/12; C07D 239/42; C07D 239/78; C07D 239/84; A01N 43/54
See application file for complete search history.

(56) References Cited

U.S. PATENT DOCUMENTS

| | | |
|---|---|---|
| 5,280,009 A | 1/1994 | Hamprecht et al. |
| 8,329,717 B2 | 12/2012 | Minn et al. |
| 8,445,408 B2 | 5/2013 | Minn et al. |
| 9,375,002 B2 | 6/2016 | Minn et al. |
| 2015/0094205 A1* | 4/2015 | Minn ................... C07D 403/12 504/242 |

FOREIGN PATENT DOCUMENTS

| | | |
|---|---|---|
| EP | 0523533 A1 | 1/1993 |
| WO | 2010/076009 A1 | 7/2010 |
| WO | 2010076010 A1 | 8/2010 |
| WO | 2013/144187 A1 | 10/2013 |

OTHER PUBLICATIONS

International Search Report of PCT/EP2015/064661 dated Aug. 15, 2015.

* cited by examiner

*Primary Examiner* — John Pak
(74) *Attorney, Agent, or Firm* — McBee Moore Woodward & Vanik IP, LLC

(57) ABSTRACT

What are described are compounds of the general formula (I) and agrochemically acceptable salts thereof

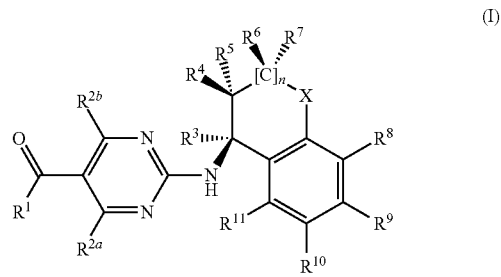

and the use thereof in the crop protection sector.

23 Claims, No Drawings

2-AMINO-5-KETO-PYRIMIDINE DERIVATIVES AND THE USE THEREOF FOR CONTROLLING UNDESIRED PLANT GROWTH

CROSS REFERENCE TO RELATED APPLICATIONS

This application is a § 371 National State Application of PCT/EP2015/064661, filed Jun. 29, 2015, which claims priority to European Application No. 14175250.1 filed Jul. 1, 2014.

FIELD AND SUMMARY OF INVENTION

The invention relates to the technical field of crop protection compositions, particularly to that of herbicides for selective control of broad-leaved weeds and weed grasses in crops of useful plants and in the ornamental garden sector and for general control of broad-leaved weeds and weed grasses in areas of the environment where plant growth is disruptive.

More particularly, the invention relates to substituted 2-amino-5-ketopyrimidine derivatives, to processes for preparation thereof and to the use thereof for control of harmful plants.

The inventive compounds of the formula (I) have, in the 5 position of the pyrimidine, a ketone and, in the 2 position of the pyrimidine, a partly hydrogenated bicyclic substituent bonded via an amine to the aromatic system in the alpha position, where the pyrimidine may likewise be substituted in the 4 position and 6 position and the ketone together with the substituent in the adjacent position may form a ring.

DESCRIPTION OF RELATED ART

The herbicidal action of diaminopyrimidines and also of monoaminopyrimidines is already known from the prior art.

Monoaminopyrimidine derivatives having herbicidal action, namely 5-aminopyrimidine derivatives, are disclosed, for example, in document WO 2013/144187 A1, while 2,4-diaminopyrimidines and the use thereof in the crop protection sector are disclosed, for example, by documents EP 0523533 A1, WO 2010/076009 and WO 2010/076010.

2,4-Diaminopyrimidines with a bicyclic radical which have (1R,2S) configuration on the bridged and adjacent carbon atoms and additionally feature herbicidal efficacy are known from US 2010/0167934 A1.

However, the use of the known pyrimidine derivatives as selective herbicides for control of harmful plants or as plant growth regulators in various crops of useful plants frequently entails an application rate that incurs high costs or results in unwanted damage to the useful plants. Moreover, in many cases, the use of the active ingredients is uneconomic owing to comparatively high production costs.

It is therefore desirable to provide alternative chemical active ingredients based on pyrimidine derivatives which can be used as herbicides or plant growth regulators and which are associated with certain advantages compared to systems known from the prior art.

OBJECT AND SUMMARY

It is an object of the present invention to provide alternative pyrimidine derivatives which can be used as herbicides or plant growth regulators, having satisfactory herbicidal action and a broad spectrum of activity against harmful plants and/or having high selectivity in crops of useful plants.

Moreover, compared to the pyrimidine derivatives known from the prior art, the alternative pyrimidine derivatives are to display a better profile of properties, particularly better herbicidal activity against harmful plants, a broader spectrum of harmful plants and/or higher selectivity in crops of useful plants.

The object is achieved by means of specifically substituted 2-amino-5-ketopyrimidine derivatives of the formula (I) as claimed in claim 1, which can advantageously be used as herbicides and also as plant growth regulators.

The present invention therefore provides novel compounds of the formula (I)

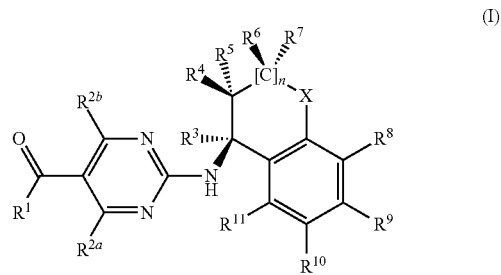

(I)

and the agrochemically acceptable salts thereof in which
$R^1$ is selected from the group consisting of
($C_1$-$C_6$)-alkyl, ($C_1$-$C_6$)-haloalkyl, ($C_1$-$C_6$)-alkylcarbonyl-($C_1$-$C_4$)-alkyl;
($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;
($C_2$-$C_6$)-alkenyl, ($C_2$-$C_6$)-haloalkenyl;
($C_2$-$C_6$)-alkynyl, ($C_2$-$C_6$)-haloalkynyl;
tri-($C_1$-$C_6$)-alkylsilyl-($C_2$-$C_6$)-alkynyl, di-($C_1$-$C_6$)-alkylsilyl-($C_2$-$C_6$)-alkynyl, mono-($C_1$-$C_6$)-alkylsilyl-($C_2$-$C_6$)-alkynyl; phenylsilyl-($C_2$-$C_6$)-alkynyl;
($C_6$-$C_{14}$)-aryl which may be substituted in the aryl moiety in each case by halogen, ($C_1$-$C_6$)-alkyl and/or ($C_1$-$C_6$)-haloalkyl;
($C_6$-$C_{14}$)-aryl-($C_1$-$C_6$)-alkyl;
aminocarbonyl-($C_1$-$C_6$)-alkyl;
($C_1$-$C_6$)-alkoxy-($C_1$-$C_6$)-alkyl;
($C_3$-$C_8$)-cycloalkyl which may optionally be substituted in the cycloalkyl radical by ($C_1$-$C_6$)-alkyl and/or halogen; ($C_3$-$C_8$)-cycloalkyl-($C_1$-$C_6$)-alkyl, ($C_3$-$C_8$)-cycloalkyl-($C_1$-$C_6$)-haloalkyl
($C_3$-$C_8$)-cycloalkenyl, ($C_3$-$C_8$)-cycloalkenyl-($C_1$-$C_6$)-alkyl, ($C_3$-$C_8$)-cycloalkenyl-($C_1$-$C_6$)-haloalkyl, hydroxy-($C_1$-$C_6$)-alkyl, cyano-($C_1$-$C_6$)-alkyl;
($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl, and
$R^{2a}$ and $R^{2b}$ are each independently selected from the group consisting of hydrogen, halogen, hydroxyl, cyano, nitro, C(O)OH, C(O)NH$_2$;

$(C_1-C_6)$-alkyl, $(C_1-C_6)$-haloalkyl, $(C_1-C_6)$-alkylcarbonyl, $(C_1-C_6)$-haloalkylcarbonyl, $(C_1-C_6)$-alkylcarbonyloxy, $(C_1-C_6)$-haloalkylcarbonyloxy, $(C_1-C_6)$-alkylcarbonyl-$(C_1-C_4)$-alkyl;

$(C_1-C_6)$-alkoxy, $(C_1-C_6)$-haloalkoxy, $(C_1-C_6)$-alkoxycarbonyl, $(C_1-C_6)$-haloalkoxycarbonyl, $(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkoxycarbonyl-$(C_1-C_6)$-haloalkyl, $(C_1-C_6)$-haloalkoxycarbonyl-$(C_1-C_6)$-haloalkyl;

$(C_2-C_6)$-alkenyl, $(C_2-C_6)$-haloalkenyl, $(C_2-C_6)$-alkenylcarbonyl, $(C_2-C_6)$-haloalkenylcarbonyl, $(C_2-C_6)$-alkenyloxy, $(C_2-C_6)$-haloalkenyloxy, $(C_2-C_6)$-alkenyloxycarbonyl, $(C_2-C_6)$-haloalkenyloxycarbonyl;

$(C_2-C_6)$-alkynyl, $(C_2-C_6)$-haloalkynyl, $(C_2-C_6)$-alkynylcarbonyl, $(C_2-C_6)$-haloalkynylcarbonyl, $(C_2-C_6)$-alkynyloxy, $(C_2-C_6)$-haloalkynyloxy, $(C_2-C_6)$-alkynyloxycarbonyl, $(C_2-C_6)$-haloalkynyloxycarbonyl;

tri-$(C_1-C_6)$-alkylsilyl-$(C_2-C_6)$-alkynyl, di-$(C_1-C_6)$-alkylsilyl-$(C_2-C_6)$-alkynyl, mono-$(C_1-C_6)$-alkylsilyl-$(C_2-C_6)$-alkynyl; phenylsilyl-$(C_2-C_6)$-alkynyl;

$(C_6-C_{14})$-aryl, $(C_6-C_{14})$-aryloxy, $(C_6-C_{14})$-arylcarbonyl and $(C_6-C_{14})$-aryloxycarbonyl, each of which may be substituted in the aryl moiety by halogen, $(C_1-C_6)$-alkyl and/or $(C_1-C_6)$-haloalkyl;

$(C_6-C_{14})$-aryl-$(C_1-C_6)$-alkyl, $(C_6-C_{14})$-aryl-$(C_1-C_6)$-alkoxy, $(C_6-C_{14})$-aryl-$(C_1-C_6)$-alkylcarbonyl, $(C_6-C_{14})$-aryl-$(C_1-C_6)$-alkylcarbonyloxy, $(C_6-C_{14})$-aryl-$(C_1-C_6)$-alkoxycarbonyl, $(C_6-C_{14})$-aryl-$(C_1-C_6)$-alkoxycarbonyloxy;

aminocarbonyl-$(C_1-C_6)$-alkyl, di-$(C_1-C_6)$-alkylaminocarbonyl-$(C_1-C_6)$-alkyl;

N—(($C_1-C_6$)-haloalkanoyl)-aminocarbonyl, mono-(($C_6-C_{14}$)-aryl)-aminocarbonyl, di-(($C_6-C_{14}$)-aryl)-aminocarbonyl;

$(C_1-C_6)$-alkoxy-$(C_1-C_6)$-alkyl, $(C_1-C_6)$-alkoxy-$(C_1-C_6)$-alkoxy, $(C_1-C_6)$-alkoxycarbonyl-$(C_1-C_6)$-alkoxy;

$(C_3-C_8)$-cycloalkyl which may optionally be substituted in the cycloalkyl radical by $(C_1-C_6)$-alkyl and/or halogen; $(C_3-C_8)$-cycloalkoxy, $(C_3-C_8)$-cycloalkyl-$(C_1-C_6)$-alkyl, $(C_3-C_8)$-cycloalkyl-$(C_1-C_6)$-haloalkyl, $(C_3-C_8)$-cycloalkyl-$(C_1-C_6)$-alkoxy, $(C_3-C_8)$-cycloalkyl-$(C_1-C_6)$-haloalkoxy, $(C_3-C_8)$-cycloalkylcarbonyl, $(C_3-C_8)$-cycloalkoxycarbonyl, $(C_3-C_8)$-cycloalkyl-$(C_1-C_6)$-alkylcarbonyl, $(C_3-C_8)$-cycloalkyl-$(C_1-C_6)$-haloalkylcarbonyl, $(C_3-C_8)$-cycloalkyl-$(C_1-C_6)$-alkoxycarbonyl, $(C_3-C_8)$-cycloalkyl-$(C_1-C_6)$-haloalkoxycarbonyl, $(C_3-C_8)$-cycloalkylcarbonyloxy, $(C_3-C_8)$-cycloalkoxycarbonyloxy, $(C_3-C_8)$-cycloalkyl-$(C_1-C_6)$-alkylcarbonyloxy, $(C_3-C_8)$-cycloalkyl-$(C_1-C_6)$-haloalkylcarbonyloxy, $(C_3-C_8)$-cycloalkyl-$(C_1-C_6)$-alkoxycarbonyloxy, $(C_3-C_8)$-cycloalkyl-$(C_1-C_6)$-haloalkoxycarbonyloxy;

$(C_3-C_8)$-cycloalkenyl, $(C_3-C_8)$-cycloalkenyloxy, $(C_3-C_8)$-cycloalkenyl-$(C_1-C_6)$-alkyl, $(C_3-C_8)$-cycloalkenyl-$(C_1-C_6)$-haloalkyl, $(C_3-C_8)$-cycloalkenyl-$(C_1-C_6)$-alkoxy, $(C_3-C_8)$-cycloalkenyl-$(C_1-C_6)$-haloalkoxy, $(C_3-C_8)$-cycloalkenylcarbonyl, $(C_3-C_8)$-cycloalkenyloxycarbonyl, $(C_3-C_8)$-cycloalkenyl-$(C_1-C_6)$-alkylcarbonyl, $(C_3-C_8)$-cycloalkenyl-$(C_1-C_6)$-haloalkylcarbonyl, $(C_3-C_8)$-cycloalkenyl-$(C_1-C_6)$-alkoxycarbonyl, $(C_3-C_8)$-cycloalkenyl-$(C_1-C_6)$-haloalkoxycarbonyl, $(C_3-C_8)$-cycloalkenylcarbonyloxy, $(C_3-C_8)$-cycloalkenyloxycarbonyloxy, $(C_3-C_8)$-cycloalkenyl-$(C_1-C_6)$-alkylcarbonyloxy, $(C_3-C_8)$-cycloalkenyl-$(C_1-C_6)$-haloalkylcarbonyloxy, $(C_3-C_8)$-cycloalkenyl-$(C_1-C_6)$-alkoxycarbonyloxy, $(C_3-C_8)$-cycloalkenyl-$(C_1-C_6)$-haloalkoxycarbonyloxy;

hydroxy-$(C_1-C_6)$-alkyl, hydroxy-$(C_1-C_6)$-alkoxy, cyano-$(C_1-C_6)$-alkoxy, cyano-$(C_1-C_6)$-alkyl; and $(C_1-C_6)$-alkylsulfonyl, $(C_1-C_6)$-alkylthio, $(C_1-C_6)$-alkylsulfinyl, $(C_1-C_6)$-haloalkylsulfonyl, $(C_1-C_6)$-haloalkylthio, $(C_1-C_6)$-haloalkylsulfinyl, $(C_1-C_6)$-alkylsulfonyl-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-haloalkylthio-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-haloalkyl, $(C_1-C_6)$-alkylthio-$(C_1-C_6)$-haloalkyl, $(C_1-C_6)$-alkylsulfinyl-$(C_1-C_6)$-haloalkyl, $(C_1-C_6)$-haloalkylsulfonyl-$(C_1-C_6)$-haloalkyl, $(C_1-C_6)$-haloalkylthio-$(C_1-C_6)$-haloalkyl, $(C_1-C_6)$-haloalkylsulfinyl-$(C_1-C_6)$-haloalkyl, $(C_1-C_6)$-alkylsulfonyloxy, $(C_1-C_6)$-haloalkylsulfonyloxy, $(C_1-C_6)$-alkylthiocarbonyl, $(C_1-C_6)$-haloalkylthiocarbonyl, $(C_1-C_6)$-alkylthiocarbonyloxy, $(C_1-C_6)$-haloalkylthiocarbonyloxy, $(C_1-C_6)$-alkylthio-$(C_1-C_6)$-alkyl, $(C_1-C_6)$-alkylthio-$(C_1-C_6)$-alkoxy, $(C_1-C_6)$-alkylthio-$(C_1-C_6)$-alkylcarbonyl, $(C_1-C_6)$-alkylthio-$(C_1-C_6)$-alkylcarbonyloxy; $(C_4-C_{14})$-arylsulfonyl, $(C_6-C_{14})$-arylthio, $(C_6-C_{14})$-arylsulfinyl, $(C_3-C_8)$-cycloalkylthio, $(C_3-C_8)$-alkenylthio, $(C_3-C_8)$-cycloalkenylthio, $(C_3-C_6)$-alkynylthio; and $R^1$ and $R^{2a}$ may be joined to one another via a bond so as to form, together with carbon 4 of the pyrimidine ring (or carbon 6 of the pyrimidine ring, depending on the way of counting) and carbon 5 of the pyrimidine and the carbonyl group in the 5 position of the pyrimidine, a 5- to 7-membered partly hydrogenated carbo- or heterocycle which may also be substituted;

$R^3$ is selected from the group consisting of hydrogen, $(C_1-C_6)$-alkyl, $(C_1-C_6)$-alkoxy, $(C_1-C_6)$-alkoxy-$(C_1-C_6)$-alkyl, $(C_1-C_6)$-alkoxycarbonyl and aminocarbonyl;

$R^4$ and $R^5$ are each independently selected from the group consisting of hydrogen, $(C_1-C_6)$-alkyl, $(C_1-C_6)$-haloalkyl, hydroxy, $(C_1-C_6)$-alkoxy and $(C_1-C_6)$-haloalkoxy; or the radicals $R^4$ and $R^5$ together with the carbon atom to which they are attached form a three- to seven-membered ring;

$R^6$ and $R^7$ are each independently selected from the group consisting of hydrogen, $(C_1-C_6)$-alkyl, $(C_1-C_6)$-haloalkyl, $(C_1-C_6)$-alkoxy, $(C_1-C_6)$-haloalkoxy, $(C_6-C_{14})$-aryl, $(C_6-C_{14})$-aryloxy, $(C_6-C_{14})$-arylcarbonyl and $(C_6-C_{14})$-aryloxycarbonyl; or the $R^6$ and $R^7$ radicals together form a $(C_1-C_7)$-alkylene group which may contain one or more oxygen and/or sulfur atoms, where the $(C_1-C_7)$-alkylene group may be mono- or polysubstituted by halogen and the respective halogen substituents may be the same or different, and n is the serial number 0, 1 or 2 and $R^8$, $R^9$, $R^{10}$ and $R^{11}$ are each independently selected from the group consisting of hydrogen, halogen, cyano, C(O)OH, C(O)NH$_2$, $(C_1-C_6)$-alkyl, $(C_1-C_6)$-alkylcarbonyl, $(C_1-C_6)$-alkyloxycarbonyl, $(C_1-C_6)$-alkylaminocarbonyl, $(C_1-C_6)$-dialkylaminocarbonyl, $(C_1-C_6)$-haloalkyl, $(C_1-C_6)$-alkoxy, $(C_1-C_6)$-haloalkoxy, $(C_2-C_6)$-alkenyl, $(C_2-C_6)$-alkynyl, $(C_2-C_6)$-haloalkynyl, $(C_2-C_6)$-alkynylcarbonyl, $(C_2-C_6)$-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl and nitro;

X is a bond (if n=1 or n=2), $CH_2$, O, S, carbonyl, NH, $CR^{12}R^{13}$ and $NR^{14}$ or $CH_2O$, $CH_2S$, where the carbon atom in the two latter groups is bonded to the aromatic moiety and the heteroatom O or S to the partly hydrogenated amine moiety; and $R^{12}$ and $R^{13}$ are each independently selected from the group consisting of hydrogen, ($C_1$-$C_6$)-alkyl and ($C_1$-$C_6$)-haloalkyl; and $R^{14}$ is selected from the group consisting of hydrogen, ($C_1$-$C_6$)-alkyl and ($C_1$-$C_6$)-haloalkyl.

The inventive 2-amino-5-ketopyrimidines of the formula (I) differ from the herbicides having 2,4-diaminopyrimidine structure that are known from EP 0523533 A1, WO 2010/076009 and WO 2010/076010 in the number of amino groups; in other words, the 2-amino-5-ketopyrimidines of the invention are substituted by just one amino group.

In the inventive monoaminopyrimidines of the formula (I), the $R^{2a}$ and $R^{2b}$ radicals are thus not an amino group; in other words, $R^{2a}$ and $R^{2b}$ are not bonded to the pyridine ring via a nitrogen atom.

The amino group in the 2 position of the pyridine, in the inventive monoaminopyrimidines of the formula (I), has a partly hydrogenated bicyclic substituent, said partly hydrogenated bicyclic substituent being bonded to the amine in the alpha position to the aromatic system.

By contrast, the 2-amino-5-ketopyrimidines of the formula (I) of the present invention differ from the pyrimidines having just one amino substituent (monoaminopyrimidines) that are known from document WO 2013/144187 A1 in that the amino group is arranged in the 2 position, i.e. between the two nitrogen atoms that form part of the pyrimidine ring, and not in the 5 position.

DETAILED DESCRIPTION OF A PREFERRED EMBODIMENT

As well as a good profile of efficacy and good crop plant compatibility, the compounds of the formula (I) are notable for their inexpensive preparation, since the substances of the invention can be prepared from inexpensive and readily available precursors by inexpensive processes. It is therefore possible to dispense with the use of intermediates that are costly and difficult to obtain.

In a preferred embodiment of the invention, the compound 1-[2-[(7-methoxy-2,2-dimethylchroman-4-yl)amino]-4-methylpyrimidin-5-yl)ethanone having the empirical formula $C_{19}H_{23}N_3O_3$ is excluded from the scope of protection of claim 1 (disclaimer 1). The aforementioned disclaimer relates to a chemical compound disclosed merely as a product offered for sale that can be ordered, but the preparability of the compound is merely suggested by the Internet offer and therefore cannot be regarded as proven.

Regardless of the question of whether the 1-[2-[(7-methoxy-2,2-dimethylchroman-4-yl)amino]-4-methylpyrimidin-5-yl)ethanone compound disclosed as a product offered for sale is relevant for the assessment of patentability of similar or else identical compounds, it can be stated that the use of the aforementioned compound as a pesticide is unknown. The same applies to the more specific use of the aforementioned compound as a herbicide.

With regard to the 1-[2-[(7-methoxy-2,2-dimethylchroman-4-yl)amino]-4-methylpyrimidin-5-yl)ethanone compound which is merely disclosed as a product offered for sale, in a further preferred embodiment of the present invention, the group of compounds of the general formula (I) according to claim 1 excludes those compounds with n=1 and X=O (oxygen) and $R^6$=$CH_3$ and $R^7$=$CH_3$ (disclaimer 2). Thus, the aforementioned embodiment excludes those compounds of the formula (I) having, as bicyclic radical, a benzopyran substituted in the 2 position by two methyl radicals.

There follows a description of preferred, particularly preferred and very particularly preferred definitions of each of the individual substituents. The other substituents of the general formula (I) which are not specified hereinafter have the definition given above. The same also applies to the serial number n, meaning that the serial number n in the embodiments which follow is 0, 1 or 2.

A first embodiment of the present invention encompasses compounds of the general formula (I) in which $R^1$ is preferably selected from the group consisting of ($C_1$-$C_6$)-alkyl, ($C_1$-$C_6$)-haloalkyl, ($C_1$-$C_6$)-alkoxy, ($C_1$-$C_6$)-alkoxy-($C_1$-$C_6$)-alkyl, ($C_3$-$C_8$)-cycloalkyl, ($C_3$-$C_8$)-cycloalkyl-($C_1$-$C_6$)-alkyl and ($C_3$-$C_8$)-cycloalkyl-($C_1$-$C_6$)-haloalkyl, where the cycloalkyl radical in each case is unsubstituted or substituted by ($C_1$-$C_6$)-alkyl and/or halogen;

$R^1$ is more preferably selected from the group consisting of ($C_1$-$C_3$)-alkyl, ($C_1$-$C_3$)-haloalkyl, ($C_1$-$C_3$)-alkoxy, ($C_1$-$C_3$)-alkoxy-($C_1$-$C_3$)-alkyl, ($C_3$-$C_6$)-cycloalkyl and ($C_3$-$C_6$)-cycloalkyl-($C_1$-$C_3$)-alkyl;

$R^1$ is even more preferably $CH_3$, $CH_2CH_3$, $CH_2CH_2CH_3$, $CH(CH_3)_2$, $CF_3$, cyclopropyl, cyclobutyl, cyclopentyl, cyclohexyl, $CH_2$-cyclopropyl or $CH_2$-cyclohexyl.

A second embodiment of the present invention encompasses compounds of the general formula (I) in which $R^{2a}$ and $R^{2b}$ are preferably each independently selected from the group consisting of hydrogen, ($C_1$-$C_6$)-alkyl, ($C_1$-$C_6$)-haloalkyl, ($C_1$-$C_6$)-alkoxy, ($C_1$-$C_6$)-alkoxy-($C_1$-$C_6$)-alkyl, ($C_3$-$C_8$)-cycloalkyl, ($C_3$-$C_8$)-cycloalkyl-($C_1$-$C_6$)-alkyl and ($C_3$-$C_8$)-cycloalkyl-($C_1$-$C_6$)-haloalkyl, where the cycloalkyl radical in each case is unsubstituted or substituted by ($C_1$-$C_6$)-alkyl and/or halogen;

$R^{2a}$ and $R^{2b}$ are more preferably each independently selected from the group consisting of hydrogen, ($C_1$-$C_3$)-alkoxy, ($C_1$-$C_3$)-alkoxy-($C_1$-$C_3$)-alkyl, ($C_3$-$C_8$)-cycloalkyl, ($C_3$-$C_8$)-cycloalkyl-($C_1$-$C_3$)-alkyl and ($C_3$-$C_8$)-cycloalkyl-($C_1$-$C_3$)-haloalkyl, where the cycloalkyl radical in each case is unsubstituted or substituted by ($C_1$-$C_3$)-alkyl and/or halogen;

$R^{2a}$ and $R^{2b}$ are even more preferably each independently selected from the group consisting of hydrogen, $CH_3$, $CH_2CH_3$, $CH(CH_3)_2$, $C(CH_3)_3$, $CF_3$, $CF_2H$, $CF_2Cl$, cyclopropyl and $CH_2OCH_3$.

A third embodiment of the present invention encompasses compounds of the general formula (I) in which $R^3$ is preferably selected from the group consisting of hydrogen, ($C_1$-$C_6$)-alkyl, ($C_1$-$C_6$)-alkoxy, ($C_1$-$C_6$)-alkoxy-($C_1$-$C_6$)-alkyl, ($C_1$-$C_6$)-alkoxycarbonyl and aminocarbonyl;

$R^3$ is more preferably selected from the group consisting of hydrogen, $CH_3$, $CH_2CH_2OCH_3$, $COOCH_3$ and $CONH_2$; and $R^3$ is most preferably selected from the group consisting of hydrogen, $CH_3$ and $COOCH_3$; and in which $R^3$ is even more preferably hydrogen.

A fourth embodiment of the present invention encompasses compounds of the general formula (I) in which $R^4$ and $R^5$ are preferably each independently selected from the group consisting of hydrogen, hydroxyl, $(C_1-C_6)$-alkyl, $(C_1-C_6)$-alkylphenyl and $(C_1-C_6)$-alkoxy;

$R^4$ and $R^5$ are more preferably each independently selected from the group consisting of hydrogen, $(C_1-C_6)$-alkyl and $(C_1-C_6)$-alkoxy;

$R^4$ and $R^5$ are even more preferably each independently selected from the group consisting of hydrogen, $(C_1-C_3)$-alkyl, $(C_1-C_6)$-alkoxy; and in which $R^4$ and $R^5$ are most preferably each independently hydrogen or methyl.

In this fourth embodiment, it is especially preferable when at least one of the $R^4$ and $R^5$ radicals is hydrogen. In other words, when at least one of the $R^4$ and $R^5$ radicals is hydrogen and the other $R^4$ and $R^5$ radical is not hydrogen, especially $(C_1-C_6)$-alkyl, preferably methyl ($CH_3$).

A fifth embodiment of the present invention encompasses compounds of the general formula (I) in which $R^6$ and $R^7$ are preferably each independently selected from the group consisting of hydrogen, $(C_1-C_6)$-alkyl and $(C_6-C_{14})$-aryl;

$R^6$ and $R^7$ are more preferably independently selected from the group consisting of hydrogen, methyl and phenyl; and in which $R^6$ and $R^7$ are even more preferably each hydrogen or methyl.

A sixth embodiment of the present invention encompasses compounds of the general formula (I) in which $R^8$ is preferably selected from the group consisting of hydrogen, halogen, $(C_1-C_6)$-alkyl, $(C_1-C_6)$-alkoxy and $(C_6-C_{14})$-aryl;

$R^8$ is more preferably selected from the group consisting of hydrogen, halogen, $(C_1-C_3)$-alkyl and $(C_6-C_8)$-aryl; and $R^8$ is even more preferably selected from the group consisting of hydrogen, fluorine, chlorine, $CH_3$ and phenyl.

A seventh embodiment of the present invention encompasses compounds of the general formula (I) in which $R^9$ is preferably selected from the group consisting of hydrogen, halogen, $(C_1-C_6)$-alkyl and $(C_1-C_6)$-alkoxy;

$R^9$ is more preferably selected from the group consisting of hydrogen, chlorine, fluorine and $(C_1-C_3)$-alkoxy; and $R^9$ is even more preferably selected from the group consisting of hydrogen, fluorine, chlorine and methoxy.

An eighth embodiment of the present invention encompasses compounds of the general formula (I) in which $R^{10}$ is preferably selected from the group consisting of hydrogen, halogen, cyano, aminocarbonyl, hydroxycarbonyl, $(C_1-C_6)$-alkyl, $(C_1-C_6)$-haloalkyl, $(C_1-C_6)$-alkoxy, $(C_2-C_6)$-alkenyl, $(C_2-C_6)$-alkynyl, $(C_1-C_6)$-alkyl-$(C_2-C_6)$-alkynyl, hydroxy-$(C_1-C_6)$-alkyl-$(C_2-C_6)$-alkynyl, $(C_1-C_6)$-alkoxy-$(C_2-C_6)$-alkynyl and aryl-$(C_2-C_6)$-alkynyl;

$R^{10}$ is more preferably selected from the group consisting of hydrogen, fluorine, chlorine, bromine, iodine, cyano, methoxy ($OCH_3$), $(C_1-C_3)$-alkyl, $(C_1-C_3)$-haloalkyl, $(C_1-C_3)$-alkoxy, $(C_2-C_4)$-alkenyl, $(C_2-C_4)$-alkynyl, $(C_1-C_3)$-alkyl-$(C_2-C_4)$-alkynyl, hydroxy-$(C_1-C_3)$-alkyl-$(C_2-C_4)$-alkynyl, $(C_1-C_3)$-alkoxy-$(C_2-C_4)$-alkynyl and phenyl-$(C_2-C_4)$-alkynyl;

$R^{10}$ is most preferably selected from the group consisting of hydrogen, fluorine, chlorine, bromine, iodine, cyano, methyl, trifluoromethyl, methoxy, $CH=CH_2$, $C\equiv CH$, $C\equiv CCH_3$, $C\equiv CPh$, $C\equiv CCH_2OH$ and $C\equiv CCH_2OCH_3$.

A ninth embodiment of the present invention encompasses compounds of the general formula (I) in which $R^{11}$ is preferably selected from the group consisting of hydrogen and $(C_1-C_6)$-alkyl;

$R^{11}$ is more preferably selected from the group consisting of hydrogen and $(C_1-C_4)$-alkyl; and $R^{11}$ is even more preferably hydrogen or methyl.

A tenth embodiment of the present invention encompasses compounds of the general formula (I) in which X is preferably selected from the group consisting of O, S, carbonyl, $CH_2$, NH, N$(C_1-C_6)$alkyl, CH$(C_1-C_6)$alkyl, di-$(C_1-C_6)$-alkylalkylene, O—$(C_1-C_7)$alkylene, S—$(C_1-C_7)$alkylene and $(C_1-C_6)$-alkylamino, or in which X is a chemical bond.

X is more preferably selected from the group consisting of O, S, carbonyl, $CH_2$, NH, $CHCH_3$, $NCH_3$, $C(CH_3)_2$, $OCH_2$ and $SCH_2$, or in which X is a chemical bond; and X is even more preferably selected from the group consisting of
O, S, $CH_2$, $CHCH_3$, $OCH_2$, $SCH_2$ and $NCH_3$, or in which X is a chemical bond.

An eleventh embodiment of the present invention encompasses compounds of the general formula (I) in which the radicals are as follows:

$R^1$ and $R^{2a}$ are preferably joined to one another via a bond so as to give, together with carbons 4 and 5 of the pyrimidine and the carbonyl group in the 5 position of the pyrimidine, a 5- to 7-membered partly hydrogenated carbo- or heterocycle in which the heteroatoms are selected from the group consisting of oxygen and sulfur, where a sulfoxide group or a sulfonyl group may be present in place of the sulfur, and the carbo- or heterocycle is unsubstituted or at least monosubstituted and where the substituents are selected from the group consisting of $(C_1-C_6)$-alkyl, $(C_1-C_6)$-haloalkyl, aryl, especially phenyl ($C_6H_5$) which is unsubstituted or at least monosubstituted by fluorine, chlorine, bromine or iodine, and $(C_1-C_6)$-cycloalkyl;

$R^1$ and $R^{2a}$ are more preferably joined to one another via a bond so as to give, together with carbons 4 and 5 of the pyrimidine and the carbonyl group in the 5 position of the pyrimidine, a 5- to 7-membered partly hydrogenated carbo- or heterocycle in which the heteroatoms are selected from the group consisting of oxygen and sulfur, where a sulfoxide group or sulfonyl group may be present in place of the sulfur, and the carbo- or heterocycle is unsubstituted or at least monosubstituted and where the substituents are selected from the group consisting of $(C_1-C_3)$-alkyl, $(C_1-C_3)$-haloalkyl, phenyl ($C_6H_5$) which is unsubstituted or at least monosubstituted by fluorine, chlorine, bromine or iodine, and $(C_1-C_3)$-cycloalkyl;

$R^1$ and $R^{2a}$ are even more preferably joined to one another via a bond so as to give, together with carbons 4 and 5 of the pyrimidine and the carbonyl group in the 5 position of the pyrimidine, a six-membered partly hydrogenated carbo- or heterocycle in which the heteroatoms are selected from the group consisting of oxygen and sulfur, where a sulfoxide group or sulfonyl group may be present in place of the sulfur, and the carbo- or heterocycle is unsubstituted or at least monosubstituted and where the substituents are selected from the group consisting of methyl, ethyl, trifluoromethyl and phenyl ($C_6H_5$) which mono- or disubstituted by fluorine, and $(C_1-C_3)$-cyclopropyl, and/or in which the $R^9$ and $R^{10}$ radicals are joined to one another via a bond consisting of the —O—$CH_2$—O— group, i.e. the $R^9$ and $R^{10}$ radicals form the aforementioned group.

In the context of the present invention, it is possible to combine the individual preferred, more preferred and even more preferred definitions of the substituents $R^1$ to $R^{11}$ and X with one another as desired, where the serial number n is 0, 1 or 2.

This means that the present invention encompasses compounds of the general formula (I) in which, for example, the substituent $R^1$ has a preferred definition and the substituents $R^2$ to $R^{14}$ have the general definition or else the substituent $R^2$ has a preferred definition, the substituent $R^3$ has a more preferred or even more preferred definition and the remaining substituents have a general definition.

Three of these combinations of the definitions given above for the substituents $R^1$ to $R^{11}$ and X are elucidated in detail hereinafter and each are disclosed as further embodiments:

- combination of the definitions referred to above as being more preferred for the substituents $R^1$ to $R^{11}$ and X (twelfth embodiment),
- combination of the definitions referred to above as being even more preferred for the substituents $R^1$ to $R^{11}$ and X (thirteenth embodiment), and
- combination of the definition referred to above as being even more preferred for the substituent $R^1$ with the definitions referred to above as being even more preferred for the substituents $R^2$ to $R^{11}$ and X (fourteenth embodiment).

The aforementioned further embodiments that are based on the combinations of the substituents are disclosed explicitly hereinafter for reasons of clarity:

A twelfth embodiment of the present invention encompasses compounds of the general formula (I) in which $R^1$ is selected from the group consisting of hydrogen, $(C_1-C_6)$-alkyl, $(C_1-C_6)$-haloalkyl, $(C_1-C_6)$-alkoxy, $(C_1-C_6)$-alkoxy-$(C_1-C_6)$-alkyl, $(C_3-C_8)$-cycloalkyl, $(C_3-C_8)$-cycloalkyl-$(C_1-C_6)$-alkyl and $(C_3-C_8)$-cycloalkyl-$(C_1-C_6)$-haloalkyl, where the cycloalkyl radical in each case is unsubstituted or substituted by $(C_1-C_6)$-alkyl and/or halogen;

$R^{2a}$ and $R^{2b}$ are each independently selected from the group consisting of hydrogen, $(C_1-C_6)$-alkyl, $(C_1-C_6)$-haloalkyl, $(C_1-C_6)$-alkoxy, $(C_1-C_6)$-alkoxy-$(C_1-C_6)$-alkyl, $(C_3-C_8)$-cycloalkyl, $(C_3-C_8)$-cycloalkyl-$(C_1-C_6)$-alkyl and $(C_3-C_8)$-cycloalkyl-$(C_1-C_6)$-haloalkyl, where the cycloalkyl radical in each case is unsubstituted or substituted by $(C_1-C_6)$-alkyl and/or halogen;

$R^3$ is selected from the group consisting of hydrogen, $(C_1-C_6)$-alkyl, $(C_1-C_6)$-alkoxy, $(C_1-C_6)$-alkoxy-$(C_1-C_6)$-alkyl, $(C_1-C_6)$-alkoxycarbonyl and aminocarbonyl;

$R^4$ and $R^5$ are each independently selected from the group consisting of hydrogen, hydroxyl, $(C_1-C_6)$-alkyl, $(C_1-C_6)$-alkylphenyl and $(C_1-C_6)$-alkoxy;

$R^6$ and $R^7$ are each independently selected from the group consisting of hydrogen, $(C_1-C_6)$-alkyl and $(C_6-C_{14})$-aryl;

$R^8$ is selected from the group consisting of hydrogen, halogen, $(C_1-C_6)$-alkyl, $(C_1-C_6)$-alkoxy and $(C_6-C_{14})$-aryl;

$R^9$ is selected from the group consisting of hydrogen, halogen, $(C_1-C_6)$-alkyl and $(C_1-C_6)$-alkoxy;

$R^{10}$ is selected from the group consisting of hydrogen, halogen, cyano, aminocarbonyl, hydroxycarbonyl, $(C_1-C_6)$-alkyl, $(C_1-C_6)$-haloalkyl, $(C_1-C_6)$-alkoxy, $(C_2-C_6)$-alkenyl, $(C_2-C_6)$-alkynyl, $(C_1-C_6)$-alkyl-$(C_2-C_6)$-alkynyl, hydroxy-$(C_1-C_6)$-alkyl-$(C_2-C_6)$-alkynyl, $(C_1-C_6)$-alkoxy-$(C_2-C_6)$-alkynyl and aryl-$(C_2-C_6)$-alkynyl;

$R^{11}$ is selected from the group consisting of hydrogen and $C_1-C_6$-alkyl; and X is selected from the group consisting of O, S, carbonyl, $CH_2$, NH, $N(C_1-C_6)$alkyl, $CH(C_1-C_6)$alkyl, di-$(C_1-C_6)$-alkylalkylene, $O—(C_1-C_7)$alkylene, $S—(C_1-C_7)$alkylene and $(C_1-C_6)$-alkylamino, or in which X is a chemical bond.

A thirteenth embodiment of the present invention encompasses compounds of the general formula (I) in which $R^1$ is selected from the group consisting of $(C_1-C_3)$-alkyl, $(C_1-C_3)$-haloalkyl, $(C_1-C_3)$-alkoxy, $(C_1-C_3)$-alkoxy-$(C_1-C_3)$-alkyl, $(C_3-C_6)$-cycloalkyl and $(C_3-C_6)$-cycloalkyl-$(C_1-C_3)$-alkyl;

$R^{2a}$ and $R^{2b}$ are each independently selected from the group consisting of hydrogen, $(C_1-C_3)$-alkoxy, $(C_1-C_3)$-alkoxy-$(C_1-C_3)$-alkyl, $(C_3-C_8)$-cycloalkyl, $(C_3-C_8)$-cycloalkyl-$(C_1-C_3)$-alkyl and $(C_3-C_8)$-cycloalkyl-$(C_1-C_3)$-haloalkyl, where the cycloalkyl radical in each case is unsubstituted or substituted by $(C_1-C_3)$-alkyl and/or halogen;

$R^3$ is selected from the group consisting of hydrogen, $CH_3$, $CH_2CH_2OCH_3$, $COOCH_3$ and $CONH_2$; and $R^4$ and $R^5$ are each independently selected from the group consisting of hydrogen, $(C_1-C_6)$-alkyl and $(C_1-C_6)$-alkoxy;

$R^6$ and $R^7$ are independently selected from the group consisting of hydrogen, methyl and phenyl;

$R^8$ is selected from the group consisting of hydrogen, halogen, $(C_1-C_3)$-alkyl and $(C_6-C_8)$-aryl;

$R^9$ is selected from the group consisting of hydrogen, chlorine, fluorine and $(C_1-C_3)$-alkoxy;

$R^{10}$ is selected from the group consisting of hydrogen, fluorine, chlorine, bromine, iodine, cyano, methoxy ($OCH_3$), $(C_1-C_3)$-alkyl, $(C_1-C_3)$-haloalkyl, $(C_1-C_3)$-alkoxy, $(C_2-C_4)$-alkenyl, $(C_2-C_4)$-alkynyl, $(C_1-C_3)$-alkyl-$(C_2-C_4)$-alkynyl, hydroxy-$(C_1-C_3)$-alkyl-$(C_2-C_4)$-alkynyl, $(C_1-C_3)$-alkoxy-$(C_2-C_4)$-alkynyl and phenyl-$(C_2-C_4)$-alkynyl;

$R^{11}$ is selected from the group consisting of hydrogen and $C_1-C_4$-alkyl; and X is selected from the group consisting of O, S, carbonyl, $CH_2$, NH, $CHCH_3$, $NCH_3$, $C(CH_3)_2$, $OCH_2$ and $SCH_2$, or in which X is a chemical bond.

A fourteenth embodiment of the present invention encompasses compounds of the general formula (I) in which $R^1$ is $CH_3$, $CH_2CH_3$, $CH_2CH_2CH_3$, $CH(CH_3)_2$, $CF_3$, cyclopropyl, cyclobutyl, cyclopentyl, cyclohexyl, $CH_2$-cyclopropyl or $CH_2$-cyclohexyl;

$R^{2a}$ and $R^{2b}$ are each independently selected from the group consisting of hydrogen, $CH_3$, $CH_2CH_3$, $CH(CH_3)_2$, $C(CH_3)_3$, $CF_3$, $CF_2H$, $CF_2Cl$, cyclopropyl and $CH_2OCH_3$;

$R^3$ is selected from the group consisting of hydrogen, $CH_3$ and $COOCH_3$;

$R^4$ and $R^5$ are each independently selected from the group consisting of hydrogen, $(C_1-C_3)$-alkyl and $(C_1-C_6)$-alkoxy;

$R^6$ and $R^7$ are each hydrogen or methyl;

$R^8$ is selected from the group consisting of hydrogen, fluorine, chlorine, $CH_3$ and phenyl;

$R^9$ is selected from the group consisting of hydrogen, fluorine, chlorine and methoxy;

$R^{10}$ is selected from the group consisting of hydrogen, fluorine, chlorine, bromine, iodine, cyano, methyl, trifluoromethyl, methoxy, $CH=CH_2$, $C\equiv CH$, $C\equiv CCH_3$, $C\equiv CPh$, $C\equiv CCH_2OH$ and $C\equiv CCH_2OCH_3$;

$R^{11}$ is hydrogen or methyl; and

X is selected from the group consisting of O, S, $CH_2$, $CHCH_3$, $OCH_2$, $SCH_2$ and $NCH_3$, or in which X is a chemical bond.

In the context of the present invention, the compound of the general formula (I) also includes compounds quaternized on a nitrogen atom by a) protonation, b) alkylation or c)

oxidation. In this respect, particular mention should be made of the corresponding N-oxides.

The compounds of the formula (I) are capable of forming salts. Salts may be formed by the action of a base on those compounds of the formula (I) that bear an acidic hydrogen atom. Examples of suitable bases are organic amines such as trialkylamines, morpholine, piperidine or pyridine, and the hydroxides, carbonates and hydrogencarbonates of ammonium, alkali metals or alkaline earth metals, especially sodium hydroxide, potassium hydroxide, sodium carbonate, potassium carbonate, sodium hydrogencarbonate and potassium hydrogencarbonate. These salts are compounds in which the acidic hydrogen is replaced by an agriculturally suitable cation, for example metal salts, especially alkali metal salts or alkaline earth metal salts, especially sodium and potassium salts, or else ammonium salts, salts with organic amines or quaternary ammonium salts, for example with cations of the formula [NRR'R"R'"]⁺ in which R to R'" are each independently of one another an organic radical, especially alkyl, aryl, aralkyl or alkylaryl. Also suitable are alkylsulfonium and alkylsulfoxonium salts, such as ($C_1$-$C_4$)-trialkylsulfonium and ($C_1$-$C_4$)-trialkylsulfoxonium salts.

The compounds of the formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. In such a case, these salts will comprise the conjugate base of the acid as the anion.

Suitable substituents present in deprotonated form, such as, for example, sulfonic acids or carboxylic acids, may form inner salts with groups which for their part can be protonated, such as amino groups.

The compounds of the formula (I) and their salts are also referred to hereinafter as "compounds (I)" according to the invention or used in accordance with the invention.

In the general formula (I) and in all the other formulae of the present invention, the radicals alkyl, alkoxy, haloalkyl, haloalkoxy, alkylamino, alkylthio, haloalkylthio and the corresponding unsaturated and/or substituted radicals can in each case be straight-chain or branched in the carbon skeleton. Unless stated specifically, preference is given for these radicals to the lower carbon skeletons, for example those having 1 to 6 carbon atoms, especially 1 to 4 carbon atoms, or in the case of unsaturated groups having 2 to 6 carbon atoms, especially 2 to 4 carbon atoms. Alkyl radicals, both alone and in composite definitions such as alkoxy, haloalkyl, etc., are, for example, methyl, ethyl, n-propyl or isopropyl, n-butyl, isobutyl, tert-butyl or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the definition of the possible unsaturated radicals corresponding to the alkyl radicals; where at least one double bond or triple bond is present, preferably one double bond or triple bond, respectively. Alkenyl is, for example, vinyl, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, ethynyl, propargyl, but-2-yn-1-yl, but-3-yn-1-yl and 1-methylbut-3-yn-1-yl.

Cycloalkyl groups are, for example, cyclopropyl, cyclobutyl, cyclopentyl, cyclohexyl, cycloheptyl and cyclooctyl. The cycloalkyl groups can be present in bi- or tricyclic form.

If haloalkyl groups and haloalkyl radicals of haloalkoxy, haloalkylthio, haloalkenyl, haloalkynyl etc. are stated, the lower carbon skeletons of these radicals having, for example, 1 to 6 carbon atoms or 2 to 6 carbon atoms, especially 1 to 4 carbon atoms or preferably 2 to 4 carbon atoms, and the corresponding unsaturated and/or substituted radicals are in each case straight-chain or branched in the carbon skeleton. Examples are difluoromethyl, 2,2,2-trifluoroethyl, trifluoroallyl, 1-chloroprop-1-yl-3-yl.

Alkylene groups in these radicals are the lower carbon skeletons, for example those having 1 to 10 carbon atoms, especially 1 to 6 carbon atoms, or preferably 2 to 4 carbon atoms, and also the corresponding unsaturated and/or substituted radicals in the carbon skeleton which may in each case be straight-chain or branched. Examples are methylene, ethylene, n- and isopropylene and n-, s-, iso-, t-butylene.

Hydroxyalkyl groups in these radicals are the lower carbon skeletons, for example those having 1 to 6 carbon atoms, especially 1 to 4 carbon atoms, and also the corresponding unsaturated and/or substituted radicals in the carbon skeleton which may in each case be straight-chain or branched. Examples of these are 1,2-dihydroxyethyl and 3-hydroxypropyl.

Halogen is fluorine, chlorine, bromine or iodine. Haloalkyl, -alkenyl and -alkynyl are alkyl, alkenyl and alkynyl partly or fully substituted by halogen, preferably by fluorine, chlorine or bromine, especially by fluorine and/or chlorine, for example monohaloalkyl, perhaloalkyl, $CF_3$, $CF_2Cl$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same correspondingly applies to haloalkenyl and other halogen-substituted radicals.

Aryl is a monocyclic, bicyclic or polycyclic aromatic system, for example phenyl or naphthyl, preferably phenyl.

Primarily for reasons of higher herbicidal activity, better selectivity and/or better preparability, inventive compounds of the general formula (I) or the agrochemical salts or quaternary N derivatives thereof that are of particular interest are those in which individual radicals have one of the preferred definitions already specified or specified below, or especially those in which one or more of the preferred definitions already specified or specified below occur in combination.

The abovementioned general or preferred radical definitions apply both to the end products of the general formula (I) and, correspondingly, to the starting materials and intermediates required in each case for the preparation. These radical definitions can be exchanged for one another as desired, i.e. including combinations between the given preferred ranges.

If tautomers are possible, the form described embraces all possible tautomeric structures. As shown below, when, for example $R^{2a}$ and/or $R^{2b}$=hydroxyl, the possible keto tautomers are likewise embraced.

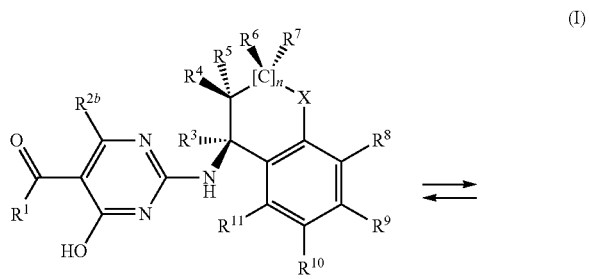

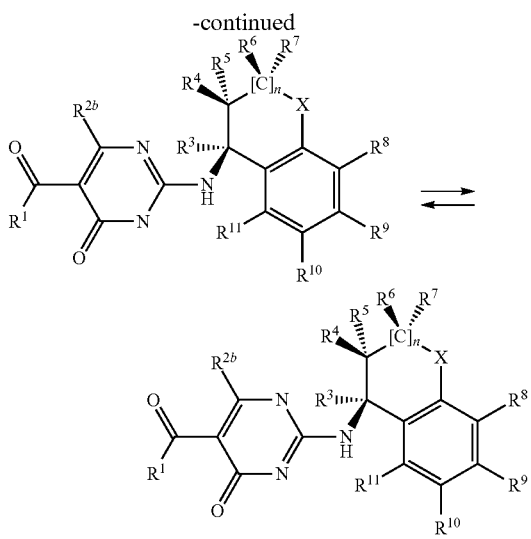

The present compounds of the general formula (I) have, at the bonding site to the aminopyrimidine, a chiral carbon atom which, in the structure shown below, is indicated by the marker (*):

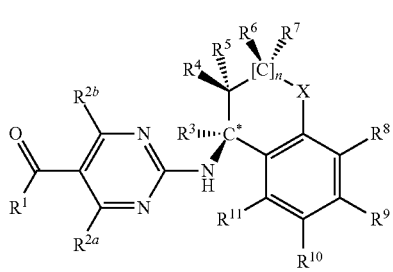

According to the rules of Cahn, Ingold and Prelog (CIP rules), this carbon atom can have either an (R) configuration or an (S) configuration.

The present invention encompasses compounds of the general formula (I) both with (S) and with (R) configuration, meaning that the present invention encompasses the compounds of the general formula (I) in which the carbon atom in question has
(1) an (R) configuration; or
(2) an (S) configuration.

In addition, the scope of the present invention also encompasses
(3) any mixtures of compounds of the general formula (I) having an (R) configuration (compounds of the general formula (I-(R)) with compounds of the general formula (I) having an (S) configuration (compounds of the general formula (I-(S)),
with a racemic mixture of the compounds of the general formula (I) having (R) and (S) configuration likewise being embraced by the present invention.

However, within the context of the present invention, preference is given to using particularly compounds of the general formula (I) having (R) configuration with a selectivity of 60 to 100%, preferably 80 to 100%, especially 90 to 100%, even more preferably 95 to 100%, where the particular (R) compound is present with an enantioselectivity of in each case more than 50% ee, preferably 60 to 100% ee, especially 80 to 100% ee, very particularly 90 to 100% ee, most preferably 95 to 100% ee, based on the total content of (R) compound in question.

Accordingly, the present invention relates especially to compounds of the general formula (I*) in which the stereochemical configuration on the carbon atom marked by (*) is present with a stereochemical purity of 60 to 100% (R), preferably 80 to 100% (R), especially 90 to 100% (R), very particularly 95 to 100% (R).

Taking into account the Cahn, Ingold and Prelog rules, at the carbon atom marked (*) there may also be a situation in which, owing to the priority of the substituent in question, the (S) configuration is preferred at the carbon atom marked (*). This is the case, for example, when the radicals $R^4$ and/or $R^5$ correspond to a $C_1$-$C_6$-alkoxy radical.

Accordingly, within the context of the present invention, preference is given especially to compounds of the general formula (I) whose spatial arrangement corresponds to that of the compounds of the general formula (I) where $R^4$ and $R^5$=hydrogen having the (R) configuration, with a selectivity of 60 to 100%, preferably 80 to 100%, especially 90 to 100%, even more preferably 95 to 100%, where the respective (R)-analogous compound is present with an enantioselectivity of in each case more than 50% ee, preferably 60 to 100% ee, especially 80 to 100% ee, even more preferably 90 to 100% ee, most preferably 95 to 100% ee, based on the total content of (R) analog compound in question. Accordingly, the present invention relates especially to compounds of the general formula (I) in which the stereochemical configuration on the carbon atom marked by (*) is present with a stereochemical purity of 60 to 100% (R or R analog), preferably 80 to 100% (R or R analog), especially 90 to 100% (R or R analog), very particularly 95 to 100% (R or R analog).

In particular, the inventive compounds of the general formula (I) may have further centers of chirality at the carbon atoms marked () and (*):

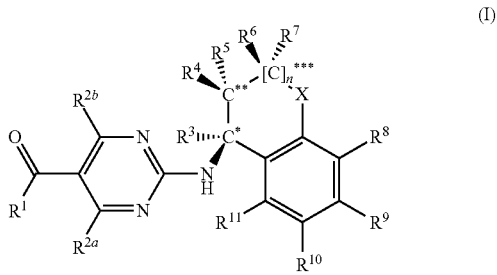

In the context of the present invention, any stereochemical configurations are possible at the carbon atoms marked (*), () and (*):

| Configuration of carbon atom (*) | Configuration of carbon atom () | Configuration of carbon atom (*) |
| --- | --- | --- |
| R | R | R |
| R | R | S |
| R | S | R |
| S | R | R |
| R | S | S |
| S | R | S |
| S | S | R |
| S | S | S |

In addition, depending on the respective radicals chosen, further stereoelements may be present in the inventive compounds of the general formula (I).

If, for example, one or more alkenyl groups are present, diastereomers (Z and E isomers) may occur.

If, for example, one or more asymmetric carbon atoms are present, enantiomers and diastereomers may occur.

Corresponding stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention thus also relates to all stereoisomers which are encompassed by the general formula (I) but are not shown in their specific stereomeric form, and to mixtures thereof.

The possible combinations of the various substituents of the general formula (I) should be understood such that the general principles of the construction of chemical compounds have to be observed, i.e. the formula (I) does not encompass any compounds known by the person skilled in the art to be chemically impossible.

Examples of the compounds of the general formula (I) are shown below in tabular form.

Tables 1 and 2 below specify the substituents defined in general terms in formula (I). In these tables:

"StNR$^3$" represents the stereochemical arrangement on the carbon atom to which NH and R$^3$ are bonded, "StR$^4$R$^5$" and "StR$^6$R$^7$" analogously represent the carbon atoms to which the respective substituents are bonded, the bond of the substituents is on the left in each case, if two bonding sites are reported for X, the left-hand bond is bonded to the aromatic ring and the right-hand bond to the hydrogenated moiety of the bicyclic amine, a hyphen "-" denotes a direct bond, and if n=0, the table does not contain an entry in the corresponding field for R$^6$ and R$^7$.

TABLE 1

| No. | R$^1$ | R$^{2a}$ | R$^{2b}$ | R$^3$ | StNR$^3$ | R$^4$ | R$^5$ | StR$^4$R$^5$ | R$^6$ |
|---|---|---|---|---|---|---|---|---|---|
| 1. 1. | CH$_3$ | H | H | H | rac | H | H | | H |
| 1. 2. | CH$_3$ | H | H | H | R | H | H | | H |
| 1. 3. | CH$_3$ | H | H | H | R | H | H | | H |
| 1. 4. | CH$_3$ | H | H | H | R | H | H | | H |
| 1. 5. | CH$_3$ | H | H | H | R | H | H | | H |
| 1. 6. | CH$_3$ | H | H | H | R | H | H | | H |
| 1. 7. | CH$_3$ | H | H | H | rac | H | H | | H |
| 1. 8. | CH$_3$ | H | H | H | rac | H | H | | H |
| 1. 9. | CH$_2$CH$_3$ | H | H | H | R | CH$_3$ | H | S | H |
| 1. 10. | CH$_3$ | H | H | H | R | CH$_3$ | H | S | H |
| 1. 11. | Cyclopropyl | H | H | H | R | CH$_3$ | H | S | H |
| 1. 12. | CH$_2$CH$_2$CH$_3$ | H | H | H | R | CH$_3$ | H | S | H |
| 1. 13. | CH$_3$ | H | H | H | R | CH$_3$ | H | S | H |
| 1. 14. | CH$_3$ | H | H | H | R | H | H | | H |
| 1. 15. | CH$_3$ | H | H | H | R | H | H | | H |
| 1. 16. | CH$_3$ | H | H | H | R | H | H | | H |
| 1. 17. | CH$_3$ | H | H | H | rac | H | H | | H |
| 1. 18. | CH$_3$ | H | H | H | rac | H | H | | H |
| 1. 19. | CH$_3$ | H | H | H | rac | H | H | | H |
| 1. 20. | CH$_3$ | H | H | H | rac | CH$_3$ | H | rac | H |
| 1. 21. | CH$_3$ | H | H | H | rac | CH$_3$ | H | rac | H |
| 1. 22. | CH$_3$ | CH$_3$ | H | H | rac | CH$_3$ | H | rac | H |
| 1. 23. | CH$_3$ | CH$_3$ | H | H | rac | H | H | | H |
| 1. 24. | CH$_3$ | CH$_3$ | H | H | R | H | H | | H |
| 1. 25. | CH$_3$ | CH$_3$ | H | H | R | CH$_3$ | H | S | H |
| 1. 26. | CH$_3$ | CH$_3$ | H | H | R | CH$_3$ | H | S | H |
| 1. 27. | CH$_3$ | CH$_3$ | H | H | R | CH$_3$ | H | S | H |
| 1. 28. | CH$_2$CH$_2$CH$_3$ | CH$_3$ | H | H | R | CH$_3$ | H | S | H |
| 1. 29. | Cyclobutyl | CH$_3$ | H | H | R | CH$_3$ | H | S | H |
| 1. 30. | Cclopentyl | CH$_3$ | H | H | R | CH$_3$ | H | S | H |
| 1. 31. | Cyclohexyl | CH$_3$ | H | H | R | CH$_3$ | H | S | H |
| 1. 32. | CH$_2$-Cyclohexyl | CH$_3$ | H | H | R | CH$_3$ | H | S | H |
| 1. 33. | CH$_2$-Cyclopropyl | CH$_3$ | H | H | R | CH$_3$ | H | S | H |
| 1. 34. | Cyclobutyl | CH$_3$ | H | H | R | CH$_3$ | H | S | H |
| 1. 35. | CH$_3$ | CH$_3$ | H | H | R | H | H | | H |
| 1. 36. | CH$_3$ | CH$_3$ | H | H | R | CH$_3$ | H | S | H |
| 1. 37. | CH$_3$ | CH$_3$ | H | H | R | CH$_3$ | H | S | H |
| 1. 38. | CH$_3$ | CH$_3$ | H | H | R | H | H | | H |
| 1. 39. | CH$_3$ | CH$_3$ | H | H | rac | H | H | | H |
| 1. 40. | CH$_2$CH$_3$ | CH$_2$CH$_3$ | H | H | R | CH$_3$ | H | S | H |
| 1. 41. | Cyclopropyl | Cyclopropyl | H | H | R | CH$_3$ | H | S | H |
| 1. 42. | CH$_3$ | CF$_3$ | H | H | R | CH$_3$ | H | S | H |
| 1. 43. | CH$_3$ | Cyclopropyl | H | H | R | CH$_3$ | H | S | H |
| 1. 44. | CH$_2$CH$_3$ | CF$_3$ | H | H | R | CH$_3$ | H | S | H |
| 1. 45. | CH$_3$ | CH$_3$ | CH$_3$ | H | R | CH$_3$ | H | S | H |
| 1. 46. | CH$_3$ | CH$_2$OCH$_3$ | H | H | R | CH$_3$ | H | S | H |
| 1. 47. | CH$_3$ | CH$_2$OCH$_3$ | H | H | R | CH$_3$ | H | S | H |
| 1. 48. | CH$_3$ | CH$_2$OCH$_3$ | H | H | R | CH$_3$ | H | S | H |
| 1. 49. | CH$_3$ | CH$_2$OCH$_3$ | CH$_3$ | H | R | CH$_3$ | H | S | H |
| 1. 50. | CH$_3$ | Cyclopropyl | CH$_3$ | H | R | CH$_3$ | H | S | H |
| 1. 51. | CF$_3$ | CH$_2$OCH$_3$ | H | H | R | CH$_3$ | H | S | H |
| 1. 52. | CF$_3$ | CH$_3$ | H | H | R | CH$_3$ | H | S | H |

TABLE 1-continued

| No. | | | | | | | | | |
|---|---|---|---|---|---|---|---|---|---|
| 1. | 53. | CF$_3$ | CH$_2$CH$_3$ | H | H | R | CH$_3$ | H | S | H |
| 1. | 54. | CF$_3$ | CH$_3$ | CH$_3$ | H | R | CH$_3$ | H | S | H |
| 1. | 55. | CF$_3$ | H | H | H | R | CH$_3$ | H | S | H |
| 1. | 56. | CF$_3$ | CH$_3$ | H | H | R | H | H | | H |
| 1. | 57. | CF$_3$ | H | H | H | R | H | H | | H |
| 1. | 58. | CF$_3$ | CH$_2$OCH$_3$ | H | H | R | H | H | | H |
| 1. | 59. | CF$_3$ | CH$_2$OCH$_3$ | H | H | R | H | H | | H |
| 1. | 60. | CF$_3$ | CH$_3$ | H | H | R | H | H | | H |
| 1. | 61. | CF$_3$ | CH$_3$ | H | H | R | CH$_3$ | H | S | H |
| 1. | 62. | CF$_3$ | H | H | H | R | CH$_3$ | H | S | H |
| 1. | 63. | CH$_3$ | CH$_3$ | CH$_3$ | H | R | CH$_3$ | H | S | H |
| 1. | 64. | CH$_3$ | CF$_3$ | H | H | R | H | H | | H |
| 1. | 65. | CH$_3$ | CH$_3$ | CH$_3$ | H | rac | H | H | | H |
| 1. | 66. | CH$_3$ | CH$_3$ | H | H | rac | H | H | | H |
| 1. | 67. | CH$_3$ | CH$_3$ | H | H | rac | H | H | | H |
| 1. | 68. | CH$_3$ | CH$_3$ | H | H | rac | H | H | | H |
| 1. | 69. | CH$_3$ | CH$_3$ | H | H | rac | H | H | | CH$_3$ |
| 1. | 70. | CH$_3$ | CH$_3$ | H | H | rac | CH$_3$ | CH$_3$ | | H |
| 1. | 71. | CH$_3$ | CH$_3$ | H | H | rac | H | H | | CH$_3$ |
| 1. | 72. | CH$_3$ | CH$_3$ | H | H | rac | H | H | | H |
| 1. | 73. | CH$_2$CH$_3$ | CH$_3$ | H | H | rac | H | H | | H |
| 1. | 74. | CH$_3$ | CH$_3$ | H | H | rac | H | H | | |
| 1. | 75. | CH$_3$ | CH$_3$ | H | H | rac | CH$_3$ | H | rac | H |
| 1. | 76. | CH$_3$ | H | H | H | rac | H | H | | H |
| 1. | 77. | CH$_3$ | H | H | H | rac | H | H | | |
| 1. | 78. | CH$_3$ | H | H | H | rac | H | H | | H |
| 1. | 79. | CH$_3$ | H | H | H | rac | H | H | | H |
| 1. | 80. | CH$_3$ | H | H | H | rac | H | H | | H |
| 1. | 81. | CH$_3$ | CH$_3$ | H | COOCH$_3$ | rac | H | H | | H |
| 1. | 82. | CH$_3$ | CH$_3$ | H | H | R | H | H | | H |
| 1. | 83. | CH$_3$ | CH$_3$ | H | H | rac | H | H | | H |
| 1. | 84. | CH$_3$ | H | H | H | R | H | H | | H |
| 1. | 85. | CH$_2$—CH$_2$—CH$_2$—CH$_3$ | H | H | CH$_3$ | R | CH$_3$ | H | S | H |
| 1. | 86. | CH$_2$-Cyclopropyl | H | H | CH$_3$ | R | CH$_3$ | H | S | H |
| 1. | 87. | CH$_3$ | CH$_3$ | H | H | rac | H | H | | H |
| 1. | 88. | CH$_3$ | CH$_3$ | H | H | R | H | H | | H |
| 1. | 89. | CH$_3$ | CH$_3$ | H | H | R | H | H | | H |
| 1. | 90. | CH$_3$ | H | H | H | R | H | H | | H |
| 1. | 91. | CH$_3$ | CH$_3$ | H | H | rac | H | H | | H |
| 1. | 92. | CH$_3$ | CH$_3$ | H | H | rac | H | H | | H |
| 1. | 93. | CH$_3$ | CH$_3$ | H | H | rac | H | H | | H |
| 1. | 94. | CH$_3$ | CH$_3$ | H | H | rac | H | H | | H |
| 1. | 95. | CH$_3$ | H | H | H | R | H | H | | H |
| 1. | 96. | CH$_3$ | CH$_3$ | H | H | rac | H | H | | CH$_3$ |

| | No. | R$^7$ | n | St R$^6$ R$^7$ | R$^8$ | R$^9$ | R$^{10}$ | R$^{11}$ | X |
|---|---|---|---|---|---|---|---|---|---|
| 1. | 1. | H | 2 | | CH$_3$ | H | CH$_3$ | H | — |
| 1. | 2. | H | 2 | | H | H | H | H | — |
| 1. | 3. | H | 2 | | H | H | H | H | — |
| 1. | 4. | H | 1 | | H | H | H | H | O |
| 1. | 5. | H | 1 | | F | H | H | H | O |
| 1. | 6. | H | 1 | | H | H | H | H | O |
| 1. | 7. | H | 1 | | CH$_3$ | H | H | H | O |
| 1. | 8. | H | 1 | | CH$_3$ | H | H | H | O |
| 1. | 9. | H | 1 | | H | H | H | H | — |
| 1. | 10. | H | 1 | | H | H | H | H | — |
| 1. | 11. | H | 1 | | H | H | H | H | — |
| 1. | 12. | H | 1 | | H | H | H | H | — |
| 1. | 13. | H | 1 | | H | H | H | H | — |
| 1. | 14. | H | 1 | | H | H | H | H | — |
| 1. | 15. | H | 1 | | H | H | F | H | — |
| 1. | 16. | H | 1 | | H | H | Cl | H | — |
| 1. | 17. | H | 1 | | H | OCH$_3$ | OCH$_3$ | H | — |
| 1. | 18. | H | 1 | | H | H | CCH | H | — |
| 1. | 19. | H | 2 | | H | H | CH$_3$ | H | — |
| 1. | 20. | H | 2 | | H | H | H | H | — |
| 1. | 21. | H | 1 | | H | H | H | H | O |
| 1. | 22. | H | 2 | | H | H | H | H | — |
| 1. | 23. | H | 2 | | CH$_3$ | H | CH$_3$ | H | — |
| 1. | 24. | H | 2 | | H | H | CH$_3$ | H | — |
| 1. | 25. | H | 2 | | H | H | H | H | — |
| 1. | 26. | H | 1 | | H | H | CH$_3$ | H | — |
| 1. | 27. | H | 1 | | H | H | CH$_3$ | H | — |
| 1. | 28. | H | 1 | | H | H | CH$_3$ | H | — |
| 1. | 29. | H | 1 | | H | H | CH$_3$ | H | — |
| 1. | 30. | H | 1 | | H | H | CH$_3$ | H | — |
| 1. | 31. | H | 1 | | H | H | CH$_3$ | H | — |

TABLE 1-continued

| No. | No. | R¹ | R²ᵃ | StN | R³ | R⁴ | R⁵ | R⁶ | A |
|---|---|---|---|---|---|---|---|---|---|
| 1. | 32. | H | 1 |  | H | H | CH₃ | H | — |
| 1. | 33. | H | 1 |  | H | H | CH₃ | H | — |
| 1. | 34. | H | 1 |  | F | H | CH₃ | H | O |
| 1. | 35. | H | 1 |  | F | H | H | H | O |
| 1. | 36. | H | 1 |  | F | H | H | H | O |
| 1. | 37. | H | 2 |  | F | H | H | H | — |
| 1. | 38. | H | 2 |  | F | H | H | H | — |
| 1. | 39. | H | 2 |  | F | H | H | H | — |
| 1. | 40. | H | 1 |  | H | H | CH₃ | H | — |
| 1. | 41. | H | 1 |  | H | H | CH₃ | H | — |
| 1. | 42. | H | 1 |  | H | H | CH₃ | H | — |
| 1. | 43. | H | 1 |  | H | H | CH₃ | H | — |
| 1. | 44. | H | 1 |  | H | H | CH₃ | H | — |
| 1. | 45. | H | 1 |  | H | H | CH₃ | H | — |
| 1. | 46. | H | 1 |  | H | H | CH₃ | H | — |
| 1. | 47. | H | 1 |  | H | H | H | H | — |
| 1. | 48. | H | 2 |  | H | H | CH₃ | H | — |
| 1. | 49. | H | 1 |  | H | H | CH₃ | H | — |
| 1. | 50. | H | 1 |  | H | H | CH₃ | H | — |
| 1. | 51. | H | 1 |  | H | H | CH₃ | H | — |
| 1. | 52. | H | 1 |  | H | H | CH₃ | H | — |
| 1. | 53. | H | 1 |  | H | H | CH₃ | H | — |
| 1. | 54. | H | 1 |  | H | H | CH₃ | H | — |
| 1. | 55. | H | 1 |  | H | H | CH₃ | H | — |
| 1. | 56. | H | 2 |  | F | H | H | H | — |
| 1. | 57. | H | 2 |  | F | H | H | H | — |
| 1. | 58. | H | 2 |  | F | H | H | H | — |
| 1. | 59. | H | 1 |  | F | H | H | H | O |
| 1. | 60. | H | 1 |  | F | H | H | H | — |
| 1. | 61. | H | 1 |  | F | H | H | H | — |
| 1. | 62. | H | 1 |  | F | H | H | H | O |
| 1. | 63. | H | 1 |  | F | H | H | H | O |
| 1. | 64. | H | 1 |  | F | H | H | H | O |
| 1. | 65. | H | 1 |  | F | H | H | H | S |
| 1. | 66. | H | 1 |  | H | H | H | H | —NMe— |
| 1. | 67. | H | 1 |  | H | H | H | H | —CHMe— |
| 1. | 68. | H | 1 |  | H | H | H | H | —C(=O)— |
| 1. | 69. | H | 1 | rac | H | H | H | H | O |
| 1. | 70. | H | 1 |  | H | H | H | H | — |
| 1. | 71. | CH₃ | 1 |  | H | H | H | H | —OH₂— |
| 1. | 72. | H | 1 |  | CH₃ | H | CH₃ | H | O |
| 1. | 73. | H | 2 |  | CH₃ | H | CH₃ | H | — |
| 1. | 74. |  | 0 |  | H | H | H | H | O |
| 1. | 75. | H | 1 |  | CH₃ | H | CH₃ | H | — |
| 1. | 76. | H | 1 |  | CH₃ | H | H | CH₃ | — |
| 1. | 77. | H | 1 |  | Cl | H | H | H | — |
| 1. | 78. | H | 1 |  | CH₃ | H | H | H | — |
| 1. | 79. | H | 1 |  | H | H | I | H | — |
| 1. | 80. | H | 1 |  | H | H | CN | H | — |
| 1. | 81. | H | 2 |  | H | H | H | H | — |
| 1. | 82. | H | 2 |  | H | H | H | H | — |
| 1. | 83. | H | 1 |  | H | H | H | H | — |
| 1. | 84. | H | 2 |  | CH₃ | H | CH₃ | H | — |
| 1. | 85. | H | 1 |  | H | H | H | H | — |
| 1. | 86. | H | 1 |  | H | H | CH3 | H | — |
| 1. | 87. | H | 1 |  | CH₃ | H | F | H | O |
| 1. | 88. | H | 2 |  | H | F | H | H | — |
| 1. | 89. | H | 1 |  | H | H | H | H | — |
| 1. | 90. | H | 1 |  | F | H | H | H | — |
| 1. | 91. | H | 1 |  | H | H | i-prop | H | — |
| 1. | 92. | H | 1 |  | H | OCH₃ | H | H | — |
| 1. | 93. | H | 1 |  | CH₃ | CH₃ | H | H | O |
| 1. | 94. | H | 1 |  | H | H | i-prop | H | O |
| 1. | 95. | H | 1 |  | CH₃ | H | CH3 | H | — |
| 1. | 96. | CH₃ | 1 |  | H | OCH₃ | H | H | O |

TABLE 2

| No. | R¹ | R²ᵃ | R²ᵇ | R³ | StN R³ | R⁴ | R⁵ | StR⁴ R⁵ | R⁶ |
|---|---|---|---|---|---|---|---|---|---|
| 2. 1. | —CH₂—CH₂—CH₂— |  | H | H | rac | H | H |  | H |
| 2. 2. | —CH₂—CHMe—CH₂— |  | H | H | rac | H | H |  | H |
| 2. 3. | —CH₂—CHEt—CH₂— |  | H | H | rac | H | H |  | H |
| 2. 4. | —CH₂—CMe₂—CH₂— |  | H | H | rac | H | H |  | H |
| 2. 5. | —CH₂—O—CH₂— |  | H | H | rac | H | H |  | H |

TABLE 2-continued

| | | | | | | | | | |
|---|---|---|---|---|---|---|---|---|---|
| 2. | 6. | —CH₂—CH(CF₃)—CH₂— | H | H | rac | H | H | | H |
| 2. | 7. | —CH₂—CH(2-F—Ph)—CH₂— | H | H | rac | H | H | | H |
| 2. | 8. | —CH₂—CH(2,4-di-F—Ph)—CH₂— | H | H | rac | H | H | | H |
| 2. | 9. | —CH₂—CH(4-F—Ph)—CH₂— | H | H | rac | H | H | | H |
| 2. | 10. | —CH₂—CH₂—CH₂—CH₂— | H | H | rac | H | H | | H |
| 2. | 11. | —CH₂—CH₂—CH₂— | CH₃ | H | rac | H | H | | H |
| 2. | 12. | —CH₂—CH₂—CH₂— | CF₃ | H | rac | H | H | | H |
| 2. | 13. | —CH₂—CH₂—CH₂— | H | H | R | H | H | | H |
| 2. | 14. | —CH₂—CHMe—CH₂— | H | H | R | H | H | | H |
| 2. | 15. | —CH₂—CMe₂—CH₂— | H | H | R | H | H | | H |
| 2. | 16. | —CH₂—CH(CF₃)—CH₂— | H | H | R | H | H | | H |
| 2. | 17. | —CH₂—O—CH₂— | H | H | R | H | H | | H |
| 2. | 18. | —CH₂—CH(2-F—Ph)—CH₂— | H | H | R | H | H | | H |
| 2. | 19. | —CH₂—CH₂—CH₂— | H | H | R | H | H | | H |
| 2. | 20. | —CH₂—CH₂—CH₂— | H | H | R | H | H | | H |
| 2. | 21. | —CH₂—CMe₂—CH₂— | H | H | R | H | H | | H |
| 2. | 22. | —CH₂—CH(4-F—Ph)—CH₂— | H | H | R | H | H | | H |
| 2. | 23. | —CH₂—CH₂—CH₂— | H | H | R | H | H | | H |
| 2. | 24. | —CH₂—O—CH₂— | H | H | R | H | H | | H |
| 2. | 25. | —CH₂—CMe₂—CH₂— | H | H | R | H | H | | H |
| 2. | 26. | —CH₂—CHMe—CH₂— | H | H | R | H | H | | H |
| 2. | 27. | —CH₂—CH₂—CH₂— | H | H | R | H | H | | H |
| 2. | 28. | —CH₂—O—CH₂— | H | H | R | H | H | | H |
| 2. | 29. | —CH₂—CH(CF₃)—CH₂— | H | H | R | H | H | | H |
| 2. | 30. | —CH₂—CH(4-F—Ph)—CH₂— | H | H | R | H | H | | H |
| 2. | 31. | —CH₂—CH₂—CH₂— | CH₃ | H | R | H | H | | H |
| 2. | 32. | —CH₂—CH₂—CH₂— | CH₃ | H | R | H | H | | H |
| 2. | 33. | —CH₂—CH₂—CH₂— | CF₃ | H | R | H | H | | H |
| 2. | 34. | —CH₂—CH₂—CH₂— | H | H | R | H | H | | H |
| 2. | 35. | —CH₂—CH₂—CH₂— | H | H | R | CH₃ | H | rac | H |
| 2. | 36. | —CH₂—CH₂—CH₂— | H | H | R | H | H | | H |
| 2. | 37. | —CH₂—CH₂—CH₂— | H | H | rac | H | H | | H |
| 2. | 38. | —CH₂—CH₂—CH₂— | H | H | R | H | H | | H |
| 2. | 39. | —CH₂—CHMe—CH₂— | H | H | R | H | H | | H |
| 2. | 40. | —CH₂—CH(CF₃)—CH₂— | H | H | R | H | H | | H |
| 2. | 41. | —CH₂—CH₂—CH₂— | H | H | R | H | H | | H |
| 2. | 42. | —CH₂—CH₂—CH₂— | H | H | rac | H | H | | H |
| 2. | 43. | —CH₂—CH₂—CH₂— | H | H | R | CH₃ | H | S | H |
| 2. | 44. | —CH₂—CHMe—CH₂— | H | H | R | CH₃ | H | S | H |
| 2. | 45. | —CH₂—CMe₂—CH₂— | H | H | R | CH₃ | H | S | H |
| 2. | 46. | —CH₂—CH(CF₃)—CH₂— | H | H | R | CH₃ | H | S | H |
| 2. | 47. | —CH₂—C(=O)—CH₂— | H | H | R | CH₃ | H | S | H |
| 2. | 48. | —CH₂—CH(Cycloprop)—CH₂— | H | H | R | CH₃ | H | S | H |
| 2. | 49. | —CH₂—CHPh—CH₂— | H | H | R | CH₃ | H | S | H |
| 2. | 50. | —CH₂—CH(2-F—Ph)—CH₂— | H | H | R | CH₃ | H | S | H |
| 2. | 51. | —CH₂—CH(2,4-di-F—Ph)—CH₂— | H | H | R | CH₃ | H | S | H |
| 2. | 52. | —CH₂—CH(4-F—Ph)—CH₂— | H | H | R | CH₃ | H | S | H |
| 2. | 53. | —CH₂—CH₂—CH₂— | CH₂CH₃ | H | R | CH₃ | H | S | H |
| 2. | 54. | —CH₂—S—CH₂— | H | H | R | CH₃ | H | S | H |
| 2. | 55. | —CH₂—S(=O)—CH₂— | H | H | R | CH₃ | H | S | H |
| 2. | 56. | —CH₂—S(=O)₂—CH₂— | H | H | R | CH₃ | H | S | H |
| 2. | 57. | —CH₂—CH₂—CH₂— | H | H | R | CH₃ | H | S | H |
| 2. | 58. | —CH₂—CH₂—CH₂— | H | H | rac | H | H | | |
| 2. | 59. | —CH₂—CH₂—CH₂— | H | H | rac | H | H | | H |
| 2. | 60. | —CH₂—CH₂—CH₂— | H | H | rac | H | H | | |
| 2. | 61. | —CH₂—CH₂—CH₂— | H | H | rac | H | H | | |
| 2. | 62. | —CH₂—CH₂—CH₂— | H | H | rac | H | H | | H |
| 2. | 63. | —CH₂—CH₂—CH₂— | H | H | rac | H | H | | H |
| 2. | 64. | —CH₂—CH₂—CH₂— | H | H | rac | H | H | | CH₃ |
| 2. | 65. | —CH₂—CH₂—CH₂— | H | CH₃ | rac | H | H | | H |
| 2. | 66. | —CH₂—CH₂—CH₂— | H | COOCH₃ | rac | H | H | | H |
| 2. | 67. | —CH₂—CH₂—CH₂— | H | H | rac | H | H | | H |
| 2. | 68. | —CH₂—CH₂—CH₂— | H | H | rac | H | H | | H |
| 2. | 69. | —CH₂—CH₂—CH₂— | H | H | rac | H | H | | H |
| 2. | 70. | —CH₂—CH₂—CH₂— | H | H | rac | H | H | | H |
| 2. | 71. | —CH₂—CH₂—CH₂— | H | H | rac | H | H | | H |
| 2. | 72. | —CH₂—CH₂—CH₂— | H | H | rac | H | H | | H |
| 2. | 73. | —CH₂—CH₂—CH₂— | H | H | rac | H | H | | H |
| 2. | 74. | —CH₂—CH₂—CH₂— | H | H | rac | H | H | | H |
| 2. | 75. | —CH₂—CH₂—CH₂— | H | H | rac | H | H | | H |
| 2. | 76. | —CH₂—CH₂—CH₂— | H | H | rac | H | H | | H |
| 2. | 77. | —CH₂—CH₂—CH₂— | H | H | rac | H | H | | H |
| 2. | 78. | —CH₂—CH₂—CH₂— | H | H | rac | H | H | | H |
| 2. | 79. | —CH₂—CH₂—CH₂— | H | H | rac | H | H | | H |
| 2. | 80. | —CH₂—CH₂—CH₂— | H | H | rac | H | H | | H |
| 2. | 81. | —CH₂—CH₂—CH₂— | H | H | rac | H | H | | H |
| 2. | 82. | —CH₂—CH₂—CH₂— | H | H | rac | H | H | | H |
| 2. | 83. | —CH₂—CH₂—CH₂— | H | H | rac | H | H | | H |
| 2. | 84. | —CH₂—CH₂—CH₂— | H | H | rac | H | H | | H |
| 2. | 85. | —CH₂—CH₂—CH₂— | H | H | rac | H | H | | H |

TABLE 2-continued

| | No. | | | | | | | | |
|---|---|---|---|---|---|---|---|---|---|
| 2. | 86. | —CH₂—CH₂—CH₂— | H | H | rac | H | H | | H |
| 2. | 87. | —CH₂—CH₂—CH₂— | H | H | rac | CH₃ | H | rac | H |
| 2. | 88. | —CH₂—CH₂—CH₂— | H | H | rac | CH₃ | H | rac | H |
| 2. | 89. | —CH₂—CH₂—CH₂— | H | H | rac | H | H | | CH₃ |
| 2. | 90. | —CH₂—CH₂—CH₂— | H | H | rac | H | H | | Ph |
| 2. | 91. | —CH₂—CH₂—CH₂— | H | H | rac | H | H | | H |
| 2. | 92. | —CH₂—CH(4-F—Ph)—CH₂— | H | H | R | H | H | | H |
| 2. | 93. | —CH₂—CH(2-F—Ph)—CH₂— | H | H | R | H | H | | H |
| 2. | 94. | —CH₂—CMe₂—CH₂— | H | H | rac | H | H | | H |
| 2. | 95. | —CH₂—CMe₂—CH₂— | H | H | rac | CH₃ | H | rac | H |
| 2. | 96. | —CH₂—CH(CF₃)—CH₂— | H | H | R | H | H | | H |
| 2. | 97. | —CH₂—O—CH₂— | H | H | R | CH₃ | H | S | H |
| 2. | 98. | —CH₂—CH₂—CH₂— | CF₃ | H | R | CH₃ | H | S | H |
| 2. | 99. | —CH₂—Ring5*—CH₂— | H | H | R | CH₃ | H | S | H |
| 2. | 100 | —CH₂—CH₂—CH₂— | H | H | R | H | H | | H |
| 2. | 101 | —CH₂—CH₂—CH₂— | H | H | R | H | H | | H |
| 2. | 102 | —CH₂—CHipr—CH₂— | H | H | R | H | H | | H |
| 2. | 103 | —CH₂—CHipr—CH₂— | H | H | R | H | H | | H |
| 2. | 104 | —CH₂—CHipr—CH₂— | H | H | R | CH₃ | H | S | H |
| 2. | 105 | —CH₂—Ring4*—CH₂— | H | H | R | H | H | | H |
| 2. | 106 | —CH₂—CH₂—CH₂— | H | H | rac | CH₂—CH₃ | H | rac | H |
| 2. | 107 | —CH₂—CH₂—CH₂— | H | H | rac | H | H | | H |
| 2. | 108 | —CH₂—CH₂—CH₂— | H | H | rac | CH₃ | H | rac | H |
| 2. | 109 | —CH₂—CH₂—CH₂— | H | H | rac | H | H | | H |
| 2. | 110 | —CH₂—Ring4*—CH₂— | H | H | R | H | H | | H |
| 2. | 111 | —CH₂—CH₂—CH₂— | H | H | rac | H | H | | H |
| 2. | 112 | —CH₂—Ring5*—CH₂— | H | H | R | H | H | | H |
| 2. | 113 | —CH₂—CH₂—CH₂— | H | H | rac | H | H | | H |
| 2. | 114 | —CH₂—CH₂—CH₂— | H | H | rac | H | H | | H |
| 2. | 115 | —CH₂—CH₂—CH₂— | H | H | rac | H | H | | H |
| 2. | 116 | —CH₂—CH₂—CH₂— | H | H | rac | H | H | | CH₃ |
| 2. | 117 | —CH₂—CH₂—CH₂— | H | H | rac | H | H | | H |
| 2. | 118 | —CH₂—CH₂—CH₂— | H | H | R | CH₃ | H | S | H |

| | No. | $R^7$ | N | St $R^6$ $R^7$ | $R^8$ | $R^9$ | $R^{10}$ | $R^{11}$ | X |
|---|---|---|---|---|---|---|---|---|---|
| 2. | 1. | H | 2 | | CH₃ | H | CH₃ | H | — |
| 2. | 2. | H | 2 | | CH₃ | H | CH₃ | H | — |
| 2. | 3. | H | 2 | | CH₃ | H | CH₃ | H | — |
| 2. | 4. | H | 2 | | CH₃ | H | CH₃ | H | — |
| 2. | 5. | H | 2 | | CH₃ | H | CH₃ | H | — |
| 2. | 6. | H | 2 | | CH₃ | H | CH₃ | H | — |
| 2. | 7. | H | 2 | | CH₃ | H | CH₃ | H | — |
| 2. | 8. | H | 2 | | CH₃ | H | CH₃ | H | — |
| 2. | 9. | H | 2 | | CH₃ | H | CH₃ | H | — |
| 2. | 10. | H | 2 | | CH₃ | H | CH₃ | H | — |
| 2. | 11. | H | 2 | | CH₃ | H | CH₃ | H | — |
| 2. | 12. | H | 2 | | CH₃ | H | CH₃ | H | — |
| 2. | 13. | H | 2 | | F | H | H | H | — |
| 2. | 14. | H | 2 | | F | H | H | H | — |
| 2. | 15. | H | 2 | | F | H | H | H | — |
| 2. | 16. | H | 2 | | F | H | H | H | — |
| 2. | 17. | H | 2 | | F | H | H | H | — |
| 2. | 18. | H | 2 | | F | H | H | H | — |
| 2. | 19. | H | 1 | | F | H | H | H | O |
| 2. | 20. | H | 1 | | F | H | H | H | S |
| 2. | 21. | H | 1 | | F | H | H | H | O |
| 2. | 22. | H | 2 | | F | H | H | H | — |
| 2. | 23. | H | 2 | | H | H | H | H | — |
| 2. | 24. | H | 2 | | H | H | H | H | — |
| 2. | 25. | H | 2 | | H | H | H | H | — |
| 2. | 26. | H | 2 | | H | H | H | H | — |
| 2. | 27. | H | 1 | | H | H | H | H | O |
| 2. | 28. | H | 1 | | H | H | H | H | O |
| 2. | 29. | H | 1 | | H | H | H | H | O |
| 2. | 30. | H | 1 | | H | H | H | H | O |
| 2. | 31. | H | 2 | | H | H | H | H | — |
| 2. | 32. | H | 1 | | H | H | H | H | O |
| 2. | 33. | H | 2 | | H | H | H | H | — |
| 2. | 34. | H | 2 | | H | H | CH₃ | H | — |
| 2. | 35. | H | 2 | | H | H | H | H | — |
| 2. | 36. | H | 1 | | CH₃ | H | CH₃ | H | —C(=O)— |
| 2. | 37. | H | 1 | | H | H | H | H | —NMe— |
| 2. | 38. | H | 1 | | H | H | H | H | — |
| 2. | 39. | H | 1 | | H | H | H | H | — |
| 2. | 40. | H | 1 | | H | H | H | H | — |
| 2. | 41. | H | 1 | | H | H | CH₃ | H | — |
| 2. | 42. | H | 1 | | H | H | F | H | — |

TABLE 2-continued

| | | R1/R2a | | | | | | |
|---|---|---|---|---|---|---|---|---|
| 2. | 43. | H | 1 | H | H | CH₃ | H | — |
| 2. | 44. | H | 1 | H | H | CH₃ | H | — |
| 2. | 45. | H | 1 | H | H | CH₃ | H | — |
| 2. | 46. | H | 1 | H | H | CH₃ | H | — |
| 2. | 47. | H | 1 | H | H | CH₃ | H | — |
| 2. | 48. | H | 1 | H | H | CH₃ | H | — |
| 2. | 49. | H | 1 | H | H | CH₃ | H | — |
| 2. | 50. | H | 1 | H | H | CH₃ | H | — |
| 2. | 51. | H | 1 | H | H | CH₃ | H | — |
| 2. | 52. | H | 1 | H | H | CH₃ | H | — |
| 2. | 53. | H | 1 | H | H | CH₃ | H | — |
| 2. | 54. | H | 1 | H | H | CH₃ | H | — |
| 2. | 55. | H | 1 | H | H | CH₃ | H | — |
| 2. | 56. | H | 1 | H | H | CH₃ | H | — |
| 2. | 57. | H | 1 | CH₃ | H | CH₃ | H | — |
| 2. | 58. |   | 0 | H | H | H | H | O |
| 2. | 59. | H | 1 | H | H | H | H | S |
| 2. | 60. |   | 0 | H | H | H | H | —CH₂—O— |
| 2. | 61. |   | 0 | H | H | H | H | —CH₂—S— |
| 2. | 62. | H | 1 | H | H | CH₃ | H | —NMe— |
| 2. | 63. | H | 1 | H | H | CH₃ | H | —C(=O)— |
| 2. | 64. | CH₃ | 1 | H | H | CH₃ | H | —CH₂— |
| 2. | 65. | H | 2 | H | H | H | H | — |
| 2. | 66. | H | 2 | H | H | H | H | — |
| 2. | 67. | H | 1 | H | H | Cl | H | — |
| 2. | 68. | H | 1 | H | H | OCH₃ | H | — |
| 2. | 69. | H | 1 | H | H | CN | H | — |
| 2. | 70. | H | 1 | H | H | Br | H | — |
| 2. | 71. | H | 1 | H | H | I | H | — |
| 2. | 72. | H | 1 | H | H | CH=CH₂ | H | — |
| 2. | 73. | H | 1 | H | H | CCH | H | — |
| 2. | 74. | H | 1 | H | H | C≡CCH₃ | H | — |
| 2. | 75. | H | 1 | H | H | C≡CPh | H | — |
| 2. | 76. | H | 1 | H | H | C≡CCH₂OH | H | — |
| 2. | 77. | H | 1 | H | H | C≡CCH₂OCH₃ | H | — |
| 2. | 78. | H | 1 | H | Cl | Cl | H | — |
| 2. | 79. | H | 1 | H | —O—CH₂—O— | | H | — |
| 2. | 80. | H | 1 | H | H | CF₃ | H | — |
| 2. | 81. | H | 1 | H | H | H | CH₃ | — |
| 2. | 82. | H | 1 | CH₃ | H | H | CH₃ | — |
| 2. | 83. | H | 1 | CH₃ | H | H | H | O |
| 2. | 84. | H | 1 | Cl | H | H | H | O |
| 2. | 85. | H | 1 | Cl | H | CH₃ | H | O |
| 2. | 86. | H | 1 | Ph | H | H | H | O |
| 2. | 87. | H | 1 | H | H | H | H | O |
| 2. | 88. | H | 1 | Cl | H | Cl | H | O |
| 2. | 89. | CH₃ | 1 | H | H | H | H | O |
| 2. | 90. | H | 1 | H | H | H | H | O |
| 2. | 91. | H | 1 | H | H | H | H | — |
| 2. | 92. | H | 2 | H | H | H | H | — |
| 2. | 93. | H | 2 | H | H | H | H | — |
| 2. | 94. | H | 1 | H | H | H | H | O |
| 2. | 95. | H | 2 | H | H | H | H | — |
| 2. | 96. | H | 2 | H | H | H | H | — |
| 2. | 97. | H | 1 | H | H | CH₃ | H | — |
| 2. | 98. | H | 1 | H | H | CH₃ | H | — |
| 2. | 99. | H | 1 | H | H | CH₃ | H | — |
| 2. | 100 | H | 1 | CH₃ | H | H | H | O |
| 2. | 101 | H | 2 | H | F | H | H | — |
| 2. | 102 | H | 2 | H | H | H | H | — |
| 2. | 103 | H | 1 | H | H | H | H | — |
| 2. | 104 | H | 1 | H | H | CH₃ | H | — |
| 2. | 105 | H | 1 | H | H | CH₃ | H | — |
| 2. | 106 | H | 1 | H | H | CH₃ | H | — |
| 2. | 107 | H | 1 | H | H | i-Pr | H | — |
| 2. | 108 | H | 1 | H | Cl | H | H | — |
| 2. | 109 | H | 2 | H | OCH₃ | H | H | — |
| 2. | 110 | H | 2 | H | H | H | H | — |
| 2. | 111 | H | 1 | H | H | H | H | CHCH₃ |
| 2. | 112 | H | 1 | H | H | CH₃ | H | — |
| 2. | 113 | H | 1 | H | H | i-Pr | H | O |
| 2. | 114 | H | 1 | H | H | F | H | S |
| 2. | 115 | H | 1 | CF₃ | H | H | H | — |
| 2. | 116 | CH₃ | 1 | H | O—CH₃ | H | H | O |
| 2. | 117 |   | 0 | H | H | CH₃ | H | O |
| 2. | 118 | H | 1 | H | H | CH₃ | H | — |

In table 2, Ring4* and Ring5* in the R1/R2a column respectively represent a four- and five-membered spirocycle with —CH₂—CH₂—CH₂—CH₂— and CH₂—CH₂—CH₂—CH₂—CH₂— as the ring.

The present invention further provides processes for preparing corresponding compounds of the general formula (I) and/or salts thereof and/or agrochemically acceptable quaternized nitrogen derivatives thereof:

a.) Compounds of the general formula (I)

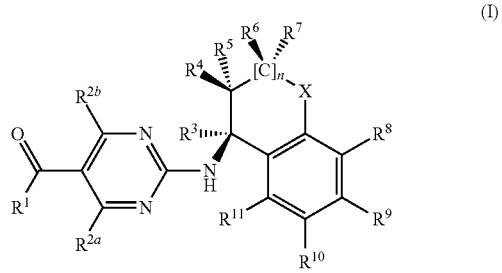

in which the $R^1$ to $R^{11}$ and X radicals have the definitions given above are prepared by reacting a compound of the general formula (II)

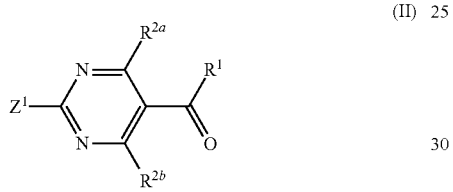

in which $R^1$ and $R^{2a}$ and also $R^{2b}$ have the above definition and $Z^1$ is an exchangeable radical or a leaving group, with an amine of general formula (III) or an acid addition salt of the amine of the general formula (III)

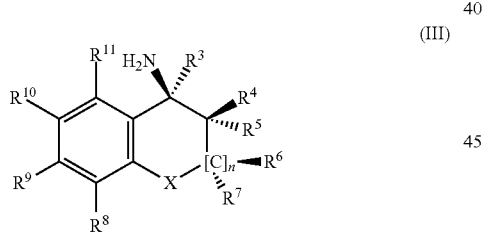

where the $R^3$ to $R^{11}$ and X radicals have the above definition.

The exchangeable $Z^1$ radical or the leaving $Z^1$ group is fluorine, chlorine, bromine, iodine, a $(C_1-C_4)$-alkylsulfanyl or a $(C_1-C_4)$-alkylsulfinyl or a $(C_1-C_4)$-alkylsulfonyl, an unsubstituted or substituted phenyl-$(C_1-C_4)$-alkylsulfonyl or a $(C_1-C_4)$-alkylphenylsulfonyl.

If necessary, a $Z^1$ radical can be converted to another group of better exchangeability. For example, in the context of a two-stage one-pot method, a $(C_1-C_4)$-alkylsulfanyl can be converted with an oxidizing agent such as m-chloroperbenzoic acid or Oxone® to a $(C_1-C_4)$-alkylsulfinyl or a $(C_1-C_4)$-alkylsulfonyl or mixtures thereof, and then reacted with an amine of the general formula (III) or an acid addition salt using an auxiliary base, for example triethylamine or potassium carbonate.

The compounds of the general formula (II) are commercially available or can be prepared by known methods.

The reaction may optionally also be catalyzed by various auxiliaries, for example by the reagents potassium phosphate, copper(I) iodide and N,N-diethyl-2-hydroxybenzamide, or in the manner of a Buchwald-Hartwig coupling by special transition metal catalyst systems.

The amines of the general formula (III) or the acid addition salt thereof are commercially available, or the synthesis thereof is described in WO2004/069814 A1.

b.) Compounds of the general formula (I) can also be prepared by first converting a compound of the general formula (II-A) analogously to the method described under a. with an amine of the formula (III) or an acid addition salt thereof to an intermediate of the formula (I-A)

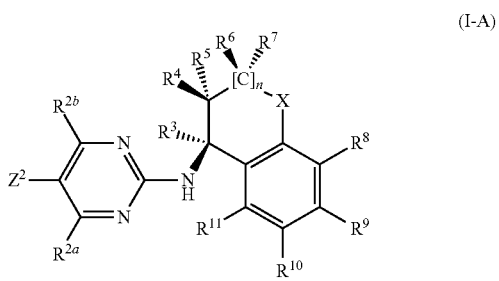

and then converting the $Z^2$ radical to a ketone. For example, in the case that $Z^2=(C_2-C_6)$-alkynyl, the $(C_2-C_6)$-alkynyl group can be converted to —C(=O)—CH$_2$—$(C_1-C_4)$-alkynyl or, when $Z^2$=trimethylsilylacetylene, to ethynyl; for example, the $Z^2$ radical=COOH or COO$(C_1-C_6)$-alkyl by methods known in the literature to C(=O)—$R^1$.

If necessary, a $Z^2$ radical can be converted to another $Z^2$ radical first. For example, by the methods described above, it is thus possible to prepare an intermediate of the (I-A) type in which the $Z^2$ radical is a halogen and to convert the halogen by methods known from the literature to a $(C_2-C_6)$-alkynyl or a 1-$(C_1-C_6)$-alkoxy-$(C_2-C_6)$-alkenyl and then to convert the $Z^2$ radical to a C(=O)—$R^1$.

c.) Compounds of the general formula (I) can also be prepared by condensing amidines of the (IV) type or acid addition salts thereof

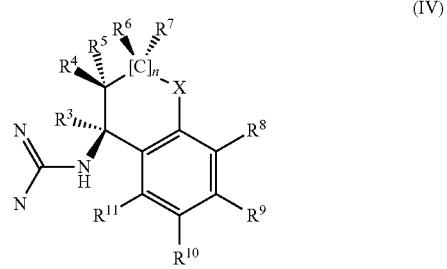

with a ketone of the formula (V)

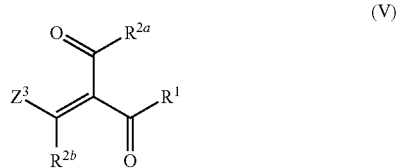

in the $Z^3$ radical is a $(C_1-C_6)$-alkoxy or di-$(C_1-C_6)$-alkylamino.

d.) Compounds of the general formula (I) can also be prepared in a three-component reaction by condensing amidines of the (IV) type or acid addition salts

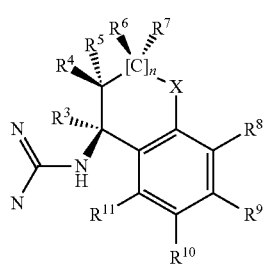

with a ketone of the formula (VI)

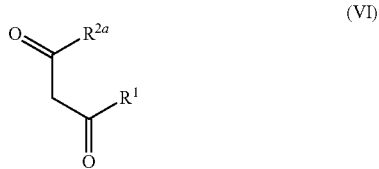

and with a fragment (VII) in which $Z^3$ is a $(C_1-C_6)$-alkoxy or di-$(C_1-C_6)$-alkylamino and $Z^4$ is a $(C_1-C_6)$-alkoxy

e.) Compounds of the general formula (II) in which the $Z^1$ radical is $(C_1-C_4)$-alkylsulfanyl can be prepared analogously to the methods described in c.) or d.), except using, rather than (IV), S—$(C_1-C_4)$-alkylisothioureas or the acid addition salts thereof.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor Gunther Jung), Wiley, 1999, on pages 1 to 34.

For the parallelized conduct of the reaction and workup, it is possible to use a number of commercially available instruments, for example reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from Teledyne ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, compounds of the general formula (I) and salts thereof can be prepared completely or partially by solid-phase-supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid-phase-supported synthesis methods permits a number of protocols, which are known from the literature and which for their part may be performed manually or in an automated manner.

Both in the solid and in the liquid phase, the conduction of individual or several synthesis steps may be supported by the use of microwave technology. The specialist literature describes a series of experimental protocols, for example in Microwaves in Organic and Medicinal Chemistry (editor: C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

On account of the herbicidal property of the compounds of the general formula (I), the invention also further provides for the use of the inventive compounds of the general formula (I) as herbicides for control of harmful plants.

Herbicides are used in agriculturally utilized crops during various cultivation phases. Thus, the application of some products even takes place before or during sowing. Others are applied before the crop plant emerges, i.e. before the seedling breaks through the earth's surface (pre-emergence herbicides). Finally, post-emergence herbicides are used if either already the seed leaves or foliage leaves have been formed by the crop plant.

The compounds of the invention can be employed either pre-emergence or post-emergence, preference being given to pre-emergence use of the compounds of the invention.

The pre-emergence treatment includes both the treatment of the area under cultivation prior to sowing (ppi=pre plant incorporation) and the treatment of the sown areas of cultivation which do not yet sustain any growth.

The compounds of the formula (I) according to the invention and their salts, also referred to synonymously and collectively hereinafter as compounds of the formula (I), have excellent herbicidal efficacy against a broad spectrum of economically important monocotyledonous and dicotyledonous harmful plants. The active ingredients also have good control over perennial weeds which are difficult to control and produce shoots from rhizomes, root stocks or other perennial organs. It does not matter here whether the substances are applied by the presowing method, the pre-emergence method or the post-emergence method.

Specific examples of some representatives of the monocotyledonous and dicotyledonous weed flora which can be controlled by the inventive compounds of the general formula (I) are mentioned hereinafter, without any intention that the enumeration is to impose a restriction to particular species.

On the side of the monocotyledonous weed species, e.g. *Agrostis, Alopecurus, Apera, Avena, Brachicaria, Bromus, Dactyloctenium, Digitaria, Echinochloa, Eleocharis, Eleusine, Festuca, Fimbristylis, Ischaemum, Lolium, Monochoria, Panicum, Paspalum, Phalaris, Phleum, Poa, Sagittaria, Scirpus, Setaria, Sphenoclea*, and also *Cyperus* species predominantly from the annual group and on the sides of the perennial species *Agropyron, Cynodon, Imperata* and *Sorghum* and also perennial *Cyperus* species are well controlled.

In the case of dicotyledonous weed species, the spectrum of action extends to species such as, for example,

*Galium, Viola, Veronica, Lamium, Stellaria, Amaranthus, Sinapis, Ipomoea, Matricaria, Abutilon* and *Sida* on the annual side, and *Convolvulus, Cirsium, Rumex* and *Artemisia* in the case of the perennial weeds. Moreover, herbicidal action is observed in the case of dicotyledonous weeds such as *Ambrosia, Anthemis, Carduus, Centaurea, Chenopodium, Cirsium, Convolvulus, Datura, Emex, Galeopsis, Galinsoga, Lepidium, Lindernia, Papaver, Portlaca, Polygonum, Ranunculus, Rorippa, Rotala, Seneceio, Sesbania, Solanum, Sonchus, Taraxacum, Trifolium, Urtica* and *Xanthium*.

If the inventive compounds of the general formula (I) are applied to the soil surface before germination, the weed seedlings are either prevented completely from emerging or else the weeds grow until they have reached the cotyledon stage, but then their growth stops, and, eventually, after three to four weeks have elapsed, they die completely.

If the active ingredients of the general formula (I) are applied post-emergence to the green parts of the plants, growth likewise stops very rapidly after the treatment, and the weed plants remain at the growth stage at the time of application or die completely after a certain time, such that competition by the weeds, which is harmful to the crop plants, is thus eliminated very early and in a lasting manner.

Although the inventive compounds of the general formula (I) have excellent herbicidal activity in respect of monocotyledonous and dicotyledonous weeds, crop plants of economically important crops, for example wheat, barley, rye, rice, corn, sugar beet, cotton, oilseed rape and soybean, are only damaged negligibly, if at all. This is why the present compounds are highly suitable for the selective control of unwanted plant growth in agriculturally useful plants.

In addition, the inventive substances of the general formula (I) have excellent growth regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Furthermore, they are also suitable for the general control and inhibition of unwanted vegetative growth without killing the plants in the process. Inhibition of vegetative growth plays a major role for many mono- and dicotyledonous crops since this can, for example, reduce or completely prevent lodging.

By virtue of their herbicidal and plant growth regulatory properties, the active ingredients can also be used to control harmful plants in crops of genetically modified plants which are known or are yet to be developed. In general, the transgenic plants are characterized by particular advantageous properties, for example by resistances to certain pesticides, especially certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or those with a different fatty acid composition in the harvested material. Other particular properties may be tolerance or resistance to abiotic stressors, for example heat, low temperatures, drought, salinity and ultraviolet radiation.

It is preferable to employ the inventive compounds of the general formula (I) or salts thereof in economically important transgenic crops of useful plants and ornamental plants, for example of cereals such as wheat, barley, rye, oats, sorghum and millet, rice, cassava and corn or else crops of sugar beet, cotton, soybean, oilseed rape, potato, tomato, peas and other vegetables.

It is preferable to employ the compounds of the general formula (I) as herbicides in crops of useful plants which are resistant, or have been made resistant by recombinant means, to the phytotoxic effects of the herbicides.

Conventional ways of producing novel plants which have modified properties in comparison to existing plants consist, for example, in traditional cultivation methods and the generation of mutants. Alternatively, novel plants with altered properties can be generated with the aid of recombinant methods (see, for example, EP 0221044, EP 0131624). For example, there have been descriptions in several cases of:

genetic modifications of crop plants for the purpose of modifying the starch synthesized in the plants (for example WO 92/011376, WO 92/014827, WO 91/019806), transgenic crop plants which are resistant to certain herbicides of the glufosinate type (cf., for example, EP 0242236, EP 0242246) or the glyphosate type (WO 92/000377) or the sulfonylurea type (EP 0257993, U.S. Pat. No. 5,013,659), transgenic crop plants, for example cotton, which is capable of producing *Bacillus thuringiensis* toxins (Bt toxins), which make the plants resistant to certain pests (EP 0142924, EP 0193259), transgenic crop plants having a modified fatty acid composition (WO 91/013972).

genetically modified crop plants with novel constituents or secondary metabolites, for example novel phytoalexins, which bring about an increased disease resistance (EP 0309862, EP 0464461), genetically modified plants having reduced photorespiration, which have higher yields and higher stress tolerance (EP 0305398), transgenic crop plants which produce pharmaceutically or diagnostically important proteins ("molecular pharming"), transgenic crop plants which feature higher yields or better quality, transgenic crop plants which feature a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. For the connection of the DNA fragments to one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene und Klone", VCH Weinheim, 2nd edition, 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product.

To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

It is preferable to use the inventive compounds of the general formula (I) in transgenic crops which are resistant to growth regulators, for example, dicamba, or to herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosate, glufosinate or benzoylisoxazoles and analogous active substances.

When the inventive active ingredients of the general formula (I) are used in transgenic crops, not only do the effects toward harmful plants which are observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the inventive compounds of the general formula (I) as herbicides for control of harmful plants in transgenic crop plants.

The compounds of the general formula (I) can be formulated in various ways according to which biological and/or physicochemical parameters are required. Possible formulations include, for example: Wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], Volume 7, C. Hanser Verlag Munich, 4th Ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J., H. v. Olphen, "Introduction to Clay Colloid Chemistry", 2nd ed., J. Wiley & Sons, N.Y., C. Marsden, "Solvents Guide", 2nd ed., Interscience, N.Y. 1963, McCutcheon's "Detergents and Emulsifiers Annual", MC Publ. Corp., Ridgewood N.J., Sisley and Wood, "Encyclopedia of Surface Active Agents", Chem. Publ. Co. Inc., N.Y. 1964, Schonfeldt, "Grenzflachenaktive Athylenoxidaddukte" [Interface-active Ethylene Oxide Adducts], Wiss. Verlagsgesell., Stuttgart 1976, Winnacker-Kichler, "Chemische Technologie", Volume 7, C. Hanser Verlag Munich, 4th ed. 1986.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tankmix.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleylmethyltauride. To produce the wettable powders, the herbicidally active ingredients are finely ground, for example in customary apparatus such as hammer mills, blower mills and air-jet mills, and simultaneously or subsequently mixed with the formulation auxiliaries.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophillite, or diatomaceous earth.

Suspension concentrates may be water- or oil-based. They can be produced, for example, by wet grinding by means of standard commercial bead mills and optionally the addition of surfactants, as have already been listed above, for example, for the other types of formulation.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active ingredient onto adsorptive granular inert material or by applying active ingredient concentrates to the surface of carriers, such as sand, kaolinites or granular inert material, by means of adhesives, for example polyvinyl alcohol, sodium polyacrylate or else mineral oils. Suitable active ingredients can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally 0.1% to 99% by weight, especially 0.1% to 95% by weight, of active ingredient of the formula (I).

In wettable powders, the active ingredient concentration is, for example, about 10% to 90% by weight, the remainder to 100% by weight consisting of customary formulation components. In emulsifiable concentrates, the active ingredient concentration may be about 1% to 90% and preferably 5% to 80% by weight. Formulations in the form of dusts comprise 1% to 30% by weight of active ingredient, preferably usually 5% to 20% by weight of active ingredient; sprayable solutions contain about 0.05% to 80% by weight, preferably 2% to 50% by weight of active ingredient. In the case of water-dispersible granules, the active ingredient content depends partially on whether the active ingredient is present in liquid or solid form and on which granulation auxiliaries, fillers, etc., are used. In the water-dispersible granules, the content of active ingredient is, for example, between 1% and 95% by weight, preferably between 10% and 80% by weight.

In addition, the active ingredient formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

The compounds of the general formula (I) or salts thereof can be used as such or in the form of their preparations (formulations) in a combination with other pesticidally active substances, for example insecticides, acaricides, nematicides, herbicides, fungicides, safeners, fertilizers and/or growth regulators, for example in the form of a finished formulation or of a tank mix.

For application, the formulations in the commercial form are diluted if appropriate in a customary manner, for example with water in the case of wettable powders, emulsifiable concentrates, dispersions and water-dispersible granules. Dust-type preparations, granules for soil application or granules for scattering and sprayable solutions are not normally diluted further with other inert substances prior to application.

The required application rate of the compounds of the general formula (I) varies according to the external conditions such as, inter alia, temperature, humidity and the type of herbicide used. It can vary within wide limits, for example between 0.001 and 10.0 kg/ha or more of active substance, but it is preferably between 0.005 and 5 kg/ha.

The present invention is illustrated in detail by the examples which follow, but these examples do not restrict the invention in any way.

A. Synthesis Examples

1-{2-[(1R)-1,2,3,4-tetrahydronaphthalen-1-ylamino] pyrimidin-5-yl}ethanone (Ex.: 1.3)

2.50 g (10.3 mmol) of 2-chloro-5-iodopyrimidine, 1.99 g (13.5 mmol) of (1R)-1,2,3,4-tetrahydronaphthalen-1-amine and 4.34 g (20.7 mmol) of dicyclohexylethylamine in 4.0 mL of 1-methyl-2-pyrrolidone are heated to 160° C. in a closed cuvette in the microwave for 90 minutes (Biotage Initiator, http://www.biotage.com/product-page/biotage-initiator). The crude mixture thus obtained is applied to silica gel and purified by column chromatography with heptane/ethyl acetate as the eluent. Concentration affords 4.00 g of 5-iodo-N-[(1R)-1,2,3,4-tetrahydronaphthalen-1-yl]pyrimidin-2-amine (in waxy form) (98% yield at 90% purity).

2.00 g (5.12 mmol) of 5-iodo-N-[(1R)-1,2,3,4-tetrahydronaphthalen-1-yl]pyrimidin-2-amine (90% purity), 1.07 g (10.2 mmol) of trimethylsilylacetylene, 0.05 g (0.07 mol) of bis(triphenylphosphine)palladium(II) chloride, 0.02 g (0.10 mol) of copper(I) iodide and 2.18 g (20.4 mol) of triethylamine in 3.0 mL of N,N-dimethylformamide are stirred at 70° C. for 6 hours. The crude mixture thus obtained is applied to silica gel and purified by column chromatography with heptane/ethyl acetate as the eluent. Concentration affords 1.30 g of N-[(1R)-1,2,3,4-tetrahydronaphthalen-1-yl]-5-[(trimethylsilyl)ethynyl]pyrimidin-2-amine (in waxy form) (75% yield at 95% purity).

1.30 g (4.04 mmol) of N-[(1R)-1,2,3,4-tetrahydronaphthalen-1-yl]-5-[(trimethylsilyl)ethynyl]pyrimidin-2-amine, 0.139 g (0.81 mmol) of 4-toluenesulfonic acid and 8.69 g (188.6 mol) of ethanol are heated to 120° C. in a closed cuvette in the microwave for 30 minutes (Biotage Initiator, http://www.biotage.com/product-page/biotage-initiator). The crude mixture thus obtained is applied to silica gel and purified by column chromatography with heptane/ethyl acetate as the eluent. Concentration affords 0.80 g of 1-{2-[(1R)-1,2,3,4-tetrahydronaphthalen-1-ylamino]pyrimidin-5-yl}ethanone (solid, m.p.: 128.2° C.) (70% yield at 95% purity).

1-{4-methyl-2-[(1R)-1,2,3,4-tetrahydronaphthalen-1-ylamino]pyrimidin-5-yl}ethanone (Ex.: 1.10)

Method A:
1.00 g (5.17 mmol) of 2-chloro-5-bromopyrimidine, 1.17 g (7.24 mmol) of (1R,2S)-2,6-dimethyl-2,3-dihydro-1H-inden-1-amine and 2.14 g (15.5 mmol) of potassium carbonate in 2.5 mL of 1-methyl-2-pyrrolidone are heated to 180° C. in a closed cuvette in the microwave for 180 minutes (Biotage Initiator, http://www.biotage.com/product-page/biotage-initiator). The crude mixture thus obtained is applied to silica gel and purified by column chromatography with heptane/ethyl acetate as the eluent. Concentration affords 1.39 g of 5-bromo-N-[(1R,2S)-2,6-dimethyl-2,3-dihydro-1H-inden-1-yl]pyrimidin-2-amine (in waxy form) (80% yield at 95% purity).
Method B:
2.5 g (12.9 mmol) of 2-chloro-5-bromopyrimidine, 2.50 g (15.5 mmol) of (1R,2S)-2,6-dimethyl-2,3-dihydro-1H-inden-1-amine and 2.61 g (25.8 mmol) of triethylamine in 6 mL of dioxane are heated to 120° C. in a closed cuvette in the microwave for 120 minutes (http://www.biotage.com/product-page/biotage-initiator). The crude mixture thus obtained is applied to silica gel and purified by column chromatography with heptane/ethyl acetate as the eluent. Concentration affords 3.30 g of 5-bromo-N-[(1R,2S)-2,6-dimethyl-2,3-dihydro-1H-inden-1-yl]pyrimidin-2-amine (in waxy form) (68% yield at 85% purity).

0.80 g (2.51 mmol) of 5-bromo-N-[(1R,2S)-2,6-dimethyl-2,3-dihydro-1H-inden-1-yl]pyrimidin-2-amine, 0.49 g (5.03 mmol) of trimethylsilylacetylene, 0.1 g (0.14 mol) of bis(triphenylphosphine)palladium(II) chloride, 0.02 g (0.10 mol) of copper(I) iodide and 1.45 g (13.6 mol) of triethylamine are stirred at 80° C. for 8 hours. The crude mixture thus obtained is applied to silica gel and purified by column chromatography with heptane/ethyl acetate as the eluent. Concentration affords 0.88 g of N-[(1R,2S)-2,6-dimethyl-2,3-dihydro-1H-inden-1-yl]-5-[(trimethylsilyl)ethynyl]pyrimidin-2-amine (in waxy form) (99% yield at 95% purity).

0.32 g (0.95 mmol) of N-[(1R,2S)-2,6-dimethyl-2,3-dihydro-1H-inden-1-yl]-5-[(trimethylsilyl)ethynyl]pyrimidin-2-amine, 0.03 g (0.19 mmol) of 4-toluenesulfonic acid and 1.58 g (34.3 mol) of ethanol are heated to 120° C. in a closed cuvette in the microwave for 30 minutes (Biotage Initiator, http://www.biotage.com/product-page/biotage-initiator). The crude mixture thus obtained is applied to silica gel and purified by column chromatography with heptane/ethyl acetate as the eluent. Concentration affords 0.16 g of N-[(1R,2S)-2,6-dimethyl-2,3-dihydro-1H-inden-1-yl]-5-[(trimethylsilyl)ethynyl]pyrimidin-2-amine (solid; m.p. 127.5° C.) (58% yield at 95% purity).

1-{4-methyl-2-[(1R)-1,2,3,4-tetrahydronaphthalen-1-ylamino]pyrimidin-5-yl}ethanone (Ex.: 1.82)

0.20 g (1.10 mmol) of 1-(4-methyl-2-methylsulfanylpyrimidin-5-yl)ethanone and 0.485 g (3.30 mmol) of (1R)-1,2,3,4-tetrahydronaphthalen-1-amine in 1.5 mL of 1-methyl-2-pyrrolidone are heated to 180° C. in a closed cuvette in the microwave for 180 minutes (Biotage Initiator, http://www.biotage.com/product-page/biotage-initiator). The crude mixture thus obtained is applied to silica gel and purified by column chromatography with heptane/ethyl acetate as the eluent. Concentration affords 0.037 g of 1-{4-methyl-2-[(1R)-1,2,3,4-tetrahydronaphthalen-1-ylamino]pyrimidin-5-yl}ethanone (in waxy form) (11% yield at 95% purity).

1-[2-(3,4-Dihydro-2H-chromen-4-ylamino)-4-methylpyrimidin-5-yl]ethanone (Ex.: 1.83)

0.22 g (1.21 mmol) of 1-[4-methyl-2-(methylsulfanyl)pyrimidin-5-yl]ethanone is initially charged in 7 mL of dichloromethane and cooled down to about 0-5° C., then 0.428 g (1.81 mmol) of meta-chloroperbenzoic acid (73%) is added while stirring. The mixture is then stirred for 2 hours and allowed to come to room temperature (about 20° C.) within that period. Subsequently, 0.252 g (1.69 mmol) of 3,4-dihydro-2H-chromen-4-amine and 0.643 g (6.04 mmol) of triethylamine are added. This reaction mixture is stirred at room temperature for about 3 hours and left to stand overnight. The crude mixture thus obtained is applied to silica gel and purified by column chromatography with heptane/ethyl acetate as the eluent. Concentration affords 0.191 g of 1-[2-(3,4-dihydro-2H-chromen-4-ylamino)-4-methylpyrimidin-5-yl]ethanone (solid, m.p.: 170.6° C.) (53% yield at 95% purity).

7,7-dimethyl-2-[(1R)-1,2,3,4-tetrahydronaphthalen-1-ylamino]-7,8-dihydroquinazolin-5(6H)-one (Ex.: 2.25)

2.00 g (14.2 mmol) of dimedone, 1.70 g (14.2 mmol) of N,N-dimethylformamide dimethyl acetal, 1.70 g (14.2 mmol) of dicyclohexylmethylamine and 2.00 g (7.14 mmol) of S-methylisothiourea sulfate in 5 mL of 1-methyl-2-pyrrolidone are heated to 180° C. in a closed cuvette in the microwave for 100 minutes. The crude mixture thus obtained is applied to silica gel and purified by column chromatography with heptane/ethyl acetate as the eluent. Concentration affords 1.35 g of 7,7-dimethyl-2-(methylsulfanyl)-7,8-dihydroquinazolin-5(6H)-one (solid) (40% yield at 95% purity).

0.18 g (0.87 mmol) of 7,7-dimethyl-2-(methylsulfanyl)-7,8-dihydroquinazolin-5(6H)-one is initially charged in 4 mL of dichloromethane and cooled down to about 0-5° C., then 0.383 g (1.61 mmol) of meta-chloroperbenzoic acid (73%) is added while stirring. The mixture is then stirred for 2 hours and allowed to come to room temperature (about 20° C.) within that period. Subsequently, 0.179 g (1.21 mmol) of (1R)-1,2,3,4-tetrahydronaphthalen-1-amine and 0.431 g (4.04 mmol) of triethylamine are added. This reaction mixture is stirred at room temperature for about 3 hours and left to stand overnight. The crude mixture thus obtained is applied to silica gel and purified by column chromatography with heptane/ethyl acetate as the eluent. Concentration affords 0.252 g of 7,7-dimethyl-2-[(1R)-1,2,3,4-tetrahydronaphthalen-1-ylamino]-7,8-dihydroquinazolin-5(6H)-one (in waxy form) (92% yield at 95% purity).

TABLE 3

(physicochemical characterization of selected synthesis examples)

Compound Description 1.3     solid, m.p.: 128-129° C.; logp (HCOOH): 2.51; 8.65 + 8.80 (2s, 1H, Pyr-6H);

1.4     oily; logp (HCOOH): 2.03; 1H-NMR (CDCL$_3$, 400 MHZ, δ in ppm): 2.15 (m, 1H, 1H from CH$_2$); 2.25 (s, 3H, CH$_3$); 2.30 (m, 1H, 1H from CH$_2$); 2.40 (s, 3H, CH$_3$); 4.30 (m, 2H, 2H from CH$_2$O); 5.35 (br, 1H, CH); 6.70 (br, 1H, NH); 6.90-7.00 (m, 2H, Ar—H); 7.20-7.35 (m, 2H, Ar—H); 8.20 + 8.90 (2s, 2H, Pyr-4H, Pyr-6H);

1.7     solid; m.p.: 167-168° C.; logp (HCOOH): 2.54; 1H-NMR (CDCl$_3$, 400 MHZ, δ in ppm): 2.15 (m, 1H, 1H from CH$_2$); 2.25 (s, 3H, CH$_3$); 2.30 (m, 1H, 1H from CH$_2$); 2.45 (s, 3H, CH$_3$); 4.25 (m, 2H, 2H from CH$_2$O); 5.35 (br, 1H, CH); 6.80-6.90 (m, 1H, Ar—H); 7.10-7.20 (m, 2H, Ar—H); 7.25 (br, 1H, NH); 8.15 + 8.90 (2s, 2H, Pyr-4H, Pyr-6H);

1.8     solid; m.p.: 181-182° C.; logp (HCOOH): 2.94; 1H-NMR (CDCl$_3$, 400 MHZ, δ in ppm): 2.15 (m, 1H, 1H from CH$_2$); 2.20 (s, 3H, CH$_3$); 2.25 (s, 3H, CH$_3$); 2.30 (m, 1H, 1H from CH$_3$); 2.45 (s, 3H, CH$_3$); 4.25 (m, 2H, 2H from CH$_3$O); 5.25 (br, 1H, CH); 6.80 (br, 1H, NH); 6.90 (m, 2H, Ar—H); 8.45 + 8.90 (2s, 2H, Pyr-4H, Pyr-6H);

1.10     solid; m.p.: 127-128° C.; logp (HCOOH): 2.99; 1H-NMR (CDCl$_3$, 400 MHZ, δ in ppm): 1.25 (d, 3H, CH$_3$); 1.70 (m, 2H, 2H from CH$_2$); 1.95 (m, 2H, 2H from CH$_2$); 2.45 (m, 3H, CH$_3$); 2.85 (m, 1H, 1H from CH); 5.35 (br, 1H, CH); 5.90 (br, 1H, NH); 6.95-7.10 (m, 3H, Ar—H); 8.80 + 8.90 (2s, 1H, Pyr-6H);

1.20     oily; logp (HCOOH): 2.93; 1H-NMR (CDCl$_3$, 400 MHZ, δ in ppm): 1.05 (d, 3H, CH$_3$); 2.30 (s, 3H, CH$_3$); 2.35 (m, 1H, 1H from CH$_2$); 2.45 (m, 3H, CH$_3$); 2.50 (m, 1H, 1H from CH$_2$); 3.05 (m, 1H, 1H from CH); 5.15 (br, 1H, CH); 6.30 (br, 1H, NH); 7.05-7.30 (m, 4H, Ar—H); 8.60 + 8.90 (2s, 1H, Pyr-6H);

1.26     solid; logp (HCOOH): 3.56; 1H-NMR (CDCl$_3$, 400 MHZ, δ in ppm): 1.20 (d, 3H, CH$_3$); 2.30 (m, 3H, CH$_3$); 2.35 (m, 1H, 1H from CH$_2$); 2.50 (m, 3H, CH$_3$); 2.55 (m, 1H, 1H from CH$_2$); 2.70 (m, 3H, CH$_3$); 3.05 (m, 1H, 1H from CH); 5.35 (br, 1H, CH); 5.90 (br, 1H, NH); 6.95-7.10 (m, 3H, Ar—H); 8.65 + 8.80 (2s, 1H, Pyr-6H);

1.65     solid; logp (HCOOH): 2.93; 1H-NMR (CDCl$_3$, 400 MHZ, δ in ppm): 2.20 (m, 1H, 1H from CH$_2$); 2.45 (s, 3H, CH$_3$); 2.65 (m, 1H, 1H from CH$_2$); 2.70 (s, 3H, CH$_3$); 3.10 (m, 2H, 2H from CH$_2$S); 5.45 (br, 1H, CH); 5.90 (br, 1H, NH); 6.90-7.20 (m, 3H, Ar—H); 8.65 + 8.80 (1s, 1H, Pyr-6H);

1.82     solid; logp (HCOOH): 3.03; 1H-NMR (CDCl$_3$, 400 MHZ, δ in ppm): 1.95 (m, 3H, 2H from CH$_2$, 1H from CH$_2$); 2.10 (m, 1H, 1H from CH$_2$); 2.50 (m, 3H, CH$_3$); 2.65 + 2.75 (2s, 3H, CH$_3$); 2.85 (m, 2H, 2H from CH$_2$); 5.40 (br, 1H, CH); 6.20 (br, 1H, NH); 7.10-7.30 (m, 4H, Ar—H); 8.60 + 8.80 (2s, 1H, Pyr-6H);

1.83     solid; m.p.: 170.6° C.; logp (HCOOH): 2.44; 1H-NMR (CDCl$_3$, 400 MHZ, δ in ppm): 2.15 (m, 1H, 1H from CH$_2$); 2.30 (m, 1H, 1H from CH$_2$); 2.50 (br, 3H, CH$_3$); 2.65 (br, 3H, CH$_3$); 4.25 (m, 2H, 2H from CH$_2$O); 5.35 (br, 1H, CH); 5.80 + 6.40 (br, 1H, NH); 6.90 (m, 2H, Ar—H); 7.20-7.30 (m, 2H, Ar—H); 8.40 + 8.80 (2s, 1H, Pyr-6H);

1.85     oily; logp (HCOOH): 4.65; 1H-NMR (CDCl$_3$, 400 MHZ, δ in ppm): 0.95 (t, 3H, CH$_3$); 1.25 (d, 3H, CH$_3$); 1.40 (m, 2H, 2H from CH$_2$); 1.75 (m, 2H, 2H from CH$_2$); 2.30 (s, 3H, CH$_3$); 2.35 (m, 1H, 1H from CH$_2$); 2.55 (m, 1H, 1H from CH$_2$); 2.70 (m, 3H, CH$_3$); 2.80 (m, 2H, 2H from CH$_2$); 3.05 (m, 1H, 1H from CH); 5.35 (br, 1H, CH); 5.80 (br, 1H, NH); 6.95-7.10 (m, 3H, Ar—H); 8.80 + 8.95 (2s, 2H, Pyr-4H, Pyr-6H);

1.86     oily; logp (HCOOH): 4.14; 1H-NMR (CDCl$_3$, 400 MHZ, δ in ppm): 0.20 (m, 2H, 2H from CH$_2$ in Cyclpropyl); 0.60 (m, 2H, 2H from CH$_2$ in Cyclpropyl); 1.10 (m, 1H, 1H from CH in Cyclpropyl); 1.25 (d, 3H, CH$_3$); 2.30 (s, 3H, CH$_3$); 2.35 (m, 1H, 1H from CH$_2$); 2.55 (m, 1H, 1H from CH$_2$); 2.75 (m, 2H, CH$_2$); 3.05 (m, 1H, 1H from CH); 5.35 (br, 1H, CH); 5.90 (br, 1H, NH); 6.95-7.10 (m, 3H, Ar—H); 8.75 + 8.90 (2s, 2H, Pyr-4H, Pyr-6H);

1.87     solid; m.p.: 127.2°C.; logp (HCOOH): 3.12; 1H-NMR (CDCl$_3$, 400 MHZ, δ in ppm): 2.15 (m, 1H, 1H from CH$_2$); ); 2.20 (s, 3H, CH$_3$); 2.30 (m, 1H, 1H from CH$_2$); 2.50 (br, 3H, CH$_3$); 2.65 (br, 3H, CH$_3$); 4.25 (m, 2H, 2H from CH$_2$O); 5.35 (br, 1H, CH); 5.60 + 5.90 (br, 1H, NH); 6.80 (m, 2H, Ar—H); 8.60 + 8.90 (2s, 1H, Pyr-6H);

1.88     solid; m.p.: 128.3° C.; logp (HCOOH): 3.10; 1H-NMR (CDCl$_3$, 400 MHZ, δ in ppm): 1.90 (m, 3H, 1H from CH$_2$, 2H from CH$_2$); 2.15 (m, 1H, 1H from CH$_2$); 2.50 (br, 3H, CH$_3$); 2.65 (br, 3H, CH$_3$); 2.85 (m, 2H, 2H from CH$_2$); 5.35 (br, 1H, CH); 5.60 (br, 1H, NH); 6.85 (m, 2H, Ar—H); 7.30 (m, 1H, Ar—H); 8.60 + 8.85 (2s, 1H, Pyr-6H);

1.89     solid; logp (HCOOH): 2.80; 1H-NMR (CDCl$_3$, 400 MHZ, δ in ppm: 1.90 (m, 1H, 1H from CH$_2$); 2.50 (s, 3H, CH$_3$); 2.65 (br, 4H, CH$_3$, 1H from CH$_2$); 2.90 (m, 1H, 1H from CH$_2$); 3.00 (m, 1H, 1H from CH); 5.65 (br, 1H, CH); 5.75 (br, 1H, NH); 7.10-7.3 (m, 4H, Ar—H); 8.70 + 8.90 (1s, 1H, Pyr-6H);

1.90     solid; m.p.: 111.5° C.; logp (HCOOH): 2.43; 1H-NMR (CDCl$_3$, 400 MHZ, δ in ppm: 1.95 (m, 1H, 1H from CH$_2$); 2.50 (s, 3H, CH$_3$); 2.75 (m, 1H, 1H from CH$_2$); 2.90 (m, 1H, 1H from CH$_2$); 3.10 (m, 1H, 1H from CH); 5.75 (m, 1H, CH); 6.30 (br, 1H, NH); 6.95-7.25 (m, 3H, Ar—H); 8.65 + 8.95 (2s, 2H, Pyr-4H, Pyr-6H);

1.91     solid; m.p.: 130.9° C.; logp (HCOOH): 3.90; 1H-NMR (CDCl$_3$, 400 MHZ, δ in ppm: 1.20 (d, 6H, 2*CH$_3$); 1.90 (m, 1H, 1H from CH$_2$); 2.50 (s, 3H, CH$_3$); 2.65 (br, 4H, CH$_3$, 1H from CH$_2$); 2.90 (m, 2H, 1H from CH$_2$, 1H from CH(CH$_3$)$_2$); 3.00 (m, 1H, 1H from CH); 5.65 (br, 1H, CH); 5.75 (br, 1H, NH); 7.10-7.25 (m, 3H, Ar—H); 8.60 + 8.85 (1s, 1H, Pyr-6H);

1.92     solid; m.p.: 134.0° C.; logp (HCOOH): 2.93; 1H-NMR (CDCl$_3$, 400 MHZ, δ in ppm): 1.90 (m, 3H, 1H from CH$_2$, 2H from CH$_2$); 2.10 (m, 1H, 1H from CH$_2$); 2.50 (br, 3H, CH$_3$); 2.65 (br, 3H, CH$_3$); 2.85 (m, 2H, 2H from CH$_2$); 3.80 (s, 3H, OCH$_3$); 5.35 (br, 1H, CH); 5.60 (br, 1H, NH); 6.75 (d, 1H, Ar—H); 6.85 (m, 1H, Ar—H); 7.25 (m, 1H, Ar—H); 8.60 + 8.80 (2s, 1H, Pyr-6H);

TABLE 3-continued (physicochemical characterization of selected synthesis examples)

Compound Description 1.93    solid; m.p.: 194.2° C.; logp (HCOOH): 3.14; 1H-NMR (CDCl$_3$, 400 MHZ, δ in ppm: 2.15 (br, 3H, CH$_3$); 2.25 (br, 3H, CH$_3$); 2.50 (br, 3H, CH$_3$); 2.65 (br, 3H, CH$_3$); 4.40 (m, 1H, 1H from CH$_2$); 4.80 (m, 1H, 1H from CH$_2$); 5.65 (br, 2H, CH, NH); 6.75 (d, 1H, Ar—H); 7.10 (d, 1H, Ar—H); 8.60 + 8.85 (1s, 1H, Pyr-6H);

1.94    solid; m.p.: 157.8° C.; logp (HCOOH): 3.48; 1H-NMR (CDCl$_3$, 400 MHZ, δ in ppm): 1.20 (d, 6H, 2*CH$_3$); 2.15 (m, 1H, 1H from CH$_2$); ); 2.30 (m, 1H, 1H from CH$_2$); 2.50 (br, 3H, CH$_3$); 2.65 (br, 3H, CH$_3$); 4.25 (m, 2H, 2H from CH$_2$O); 5.35 (br, 1H, CH); 5.60 + 5.90 (br, 1H, NH); 6.80 (m, 1H, Ar—H); 7.10 (m, 2H, Ar—H); 8.60 + 8.85 (2s, 1H, Pyr-6H);

1.95    solid; m.p.: 153.0° C.; logp (HCOOH): 3.45; 1H-NMR (CDCl$_3$, 400 MHZ, δ in ppm): 1.90 (m, 3H, 1H from CH$_2$, 2H from CH$_2$); 2.05 (m, 1H, 1H from CH$_2$); 2.20 (s, 3H, CH$_3$); 2.25 (s, 3H, CH$_3$); 2.50 (s, 3H, CH$_3$); 2.75 (m, 2H, 2H from CH$_2$); 5.35 (m, 1H, CH); 6.30 (br, 1H, NH); 6.95 (d, 1H, Ar—H); 7.00 (d, 1H, Ar—H); 8.60 + 8.90 (2s, 2H, Pyr-4H, Pyr-6H);

1.96    solid; m.p.: 183.5° C.; logp (HCOOH): 3.12; 1H-NMR (CDCl$_3$, 400 MHZ, δ in ppm): 1.35 (s, 3H, CH$_3$); 1.45 (s, 3H, CH$_3$); 1.80 (m, 1H, 1H from CH$_2$); ); 2.30 (m, 1H, 1H from CH$_2$); 2.50 (br, 3H, CH$_3$); 2.65 (br, 3H, CH$_3$); 3.75 (s, 3H, OCH$_3$, 5.45 (br, 1H, CH); 5.55 + 5.75 (br, 1H, NH); 6.40 (s, 1H, Ar—H); 6.50 (m, 1H, Ar—H); 7.15 (m, 1H, Ar—H); 8.60 + 8.85 (2s, 1H, Pyr-6H);

2.13    oily; logp (HCOOH): 3.03; 1H-NMR (CDCl$_3$, 400 MHZ, δ in ppm): 1.95 (m, 3H, 2H from CH$_2$, 1H from CH$_2$); 2.15 (m, 3H, 2H from CH$_2$, 1H from CH$_2$); 2.55 (m, 2H, 2H from CH$_2$); 2.70-2.90 (m, 4H, 2H from CH$_2$, 2H from CH$_2$); 5.45 (br, 1H, CH); 5.80 + 5.90 (br, 1H, NH); 6.95 (m, 1H, Ar—H); 7.15 (m, 2H, Ar—H); 8.80 + 8.85 (2s, 1H, Pyr-6H);

2.19    oily; logp (HCOOH): 2.29; 1H-NMR (CDCl$_3$, 400 MHZ, δ in ppm): 2.15 (m, 3H, 2H from CH$_2$, 1H from CH$_2$); 2.30 (m, 1H, 1H from CH$_2$); 2.55 (m, 2H, 2H from CH$_2$); 2.70-2.90 (m, 2H, 2H from CH$_2$); 4.30-4.45 (m, 2H, 2H from CH$_2$); 5.45 (m, 1H, CH); 5.80 + 5.90 (br, 1H, NH); 6.95 (m, 1H, Ar—H); 7.05 (m, 2H, Ar—H); 8.80 + 8.85 (2s, 1H, Pyr-6H);

2.23    solid; m.p.: 137.4° C.; logp (HCOOH): 2.93; 1H-NMR (CDCl$_3$, 400 MHZ, δ in ppm): 1.95 (m, 3H, 2H from CH$_2$, 1H from CH$_2$); 2.15 (m, 3H, 2H from CH$_2$, 1H from CH$_2$); 2.55 (m, 2H, 2H from CH$_2$); 2.80-3.00 (m, 4H, 2H from CH$_2$, 2H from CH$_2$); 5.45 (br, 1H, CH); 5.80 + 5.90 (br, 1H, NH); 7.10-7.30 (m, 4H, Ar—H); 8.80 + 9.00 (2s, 1H, Pyr-6H);

2.25    oily; logp (HCOOH): 3.71; 1H-NMR (CDCl$_3$, 400 MHZ, δ in ppm): 1.10 (m, 6H, 2*CH$_3$); 1.95 (m, 3H, 2H from CH$_2$, 1H from CH$_2$); 2.15 (m, 1H, 1H from CH$_2$); 2.45 (s, 2H, 2H from CH$_2$); 2.65 + 2.80 (2s, 2H, 2H from CH$_2$); 2.85 (m, 2H, 2H from CH$_2$); 5.45 (br, 1H, CH); 5.80 (br, 1H, NH); 7.10-7.30 (m, 4H, Ar—H); 8.80 + 8.95 (2s, 1H, Pyr-6H);

2.26    oily; logp (HCOOH): 3.45; 1H-NMR (CDCl$_3$, 400 MHZ, δ in ppm): 1.15 (m, 3H, CH$_3$); 1.95 (m, 3H, 2H from CH$_2$, 1H from CH$_2$); 2.15 (m, 1H, 1H from CH$_2$); 2.25-2.85 (m, 7H); 5.45 (br, 1H, CH); 5.80 + 5.90 (2br, 1H, NH); 7.10-7.30 (m, 4H, Ar—H); 8.75 + 8.95 (2s, 1H, Pyr-6H);

2.34    oily; logp (HCOOH): 3.37; 1H-NMR (CDCl$_3$, 400 MHZ, δ in ppm):

2.38    oily; logp (HCOOH): 4.84; 1H-NMR (CDCl$_3$, 400 MHZ, δ in ppm): 1.85 (m, 1H, 1H from CH$_2$); 2.15 (m, 2H, CH$_2$); 2.30 (m, 3H, 3H from CH$_3$); 2.55 (m, 2H, 2H from CH$_2$); 2.80 + 2.85 (m, 4H, 2*2H from CH$_2$); 5.70 (br, 2H, 1H from CH, 1H from NH); 7.05-7.20 (m, 3H, Ar—H); 8.80 + 8.95 (2s, 1H, Pyr-6H);

2.41    oily; logp (HCOOH): 3.21; 1H-NMR (CDCl$_3$, 400 MHZ, δ in ppm): 1.95 (m, 1H, 1H from CH$_2$); 2.15 (m, 2H, 2H from CH$_2$); 2.55 (m, 2H, 2H from CH$_2$); 2.65 (m, 2H, 2H from CH$_2$); 2.70 (m, 1H, 1H from CH$_2$); 2.90 (m, 2H, 2H from CH$_2$); 3.05 (m, 1H, 1H from CH$_2$); 5.70 (br, 1H, CH); 5.85 + 5.95 (br, 1H, NH); 7.15-7.35 (m, 4H, Ar—H); 8.65 + 8.95 (2s, 1H, Pyr-6H);

2.43    solid; logp (HCOOH): 3.45; 1H-NMR (CDCl$_3$, 400 MHZ, δ in ppm): 1.25 (t, 3H, CH$_3$); 2.15 (m, 2H, CH$_2$); 2.30 (m, 4H, 3H from CH$_3$, 1H from CH$_2$); 2.55 (m, 3H, 1H from CH$_2$, 2H from CH$_2$); 2.80 + 2.85 (2m, 2H, 2H from CH$_2$); 3.05 (m, 1H, 1H from CH); 5.40 (br, 1H, CH); 6.00 (br, 1H, NH); 6.95-7.10 (m, 3H, Ar—H); 8.80 + 8.95 (2s, 1H, Pyr-6H);

2.44    oily; logp (HCOOH): 3.90;

2.45    oily; logp (HCOOH): 4.23; 1H-NMR (CDCl$_3$, 400 MHZ, δ in ppm): 1.10 (m, 6H, 2*CH$_3$); 1.25 (t, 3H, CH$_3$); 2.30 (m + s, 4H, 3H, CH$_3$, 1H from CH$_2$); 2.45 (s, 2H, 2H from CH$_2$); 2.55 (m, 1H, 1H from CH$_2$); 2.70 + 2.80 (2s, 2H, 2H from CH$_2$); 3.05 (m, 1H, 1H from CH$_2$); 5.40 (t, 1H, CH); 5.70 (br, 1H, NH); 7.00-7.15 (m, 3H, Ar—H); 8.80 + 8.95 (2s, 1H, Pyr-6H);

2.46    oily; logp (HCOOH): 3.24; 1H-NMR (CDCl$_3$, 400 MHZ, δ in ppm): 1.25 (t, 3H, CH$_3$); 2.30 (m + s, 4H, 3H, CH$_3$, 1H from CH$_2$); 2.50 (m, 2H, 1H from CHCF$_3$, 1H from CH$_2$); 2.70-3.10 (m, 5H, 1H from CH$_2$, 2H from CH$_2$, 2H from CH$_2$); 5.35 (m, 1H, CH); 5.70 (br, 1H, NH); 7.00-7.15 (m, 3H, Ar—H); 8.85 + 8.95 (2s, 1H, Pyr-6H);

2.50    oily; logp (HCOOH): 4.86; 1H-NMR (CDCl$_3$, 400 MHZ, δ in ppm): 1.25 (t, 3H, CH$_3$); 2.30 (m + s, 4H, 3H, CH$_3$, 1H from CH$_2$); 2.50 (m, 1H, 1H from CH$_2$); 2.85 (m, 2H, 2H from CH$_2$); 3.10 (m, 3H, 1H from CH$_2$, 2H from CH$_2$); 3.85 (m, 1H, 1H from CHPh); 5.35 (m, 1H, CH); 5.80 (br, 1H, NH); 7.00-7.30 (m, 7H, Ar—H); 8.85 + 9.00 (2s, 1H, Pyr-6H);

2.52    oily; logp (HCOOH): 4.87; 1H-NMR (CDCl$_3$, 400 MHZ, δ in ppm): 1.25 (t, 3H, CH$_3$); 2.30 (m + s, 4H, 3H, CH$_3$, 1H from CH$_2$); 2.50 (m, 1H, 1H from CH$_2$); 2.70-2.90 (m, 2H, 2H from CH$_2$); 3.10 (m, 3H, 1H from CH$_2$, 2H from CH$_2$); 3.50 (m, 1H, 1H from

TABLE 3-continued (physicochemical characterization of selected synthesis examples)

| Compound | Description |
|---|---|
| | CHPh), 5.35 (m, 1H, CH); 5.80 (br, 1H, NH); 7.00-7.30 (m, 7H, Ar—H); 8.85 + 9.00 (2s, 1H, Pyr-6H); |
| 2.84 | oily; logp (HCOOH): 2.75; 1H-NMR (CDCl$_3$, 400 MHZ, δ in ppm): 2.15 (m, 3H, 2H from CH$_2$, 1H from CH$_2$); ); 2.25 (m, 1H, 1H from CH$_2$); 2.55 (q, 2H, 2H from CH$_2$); 2.70-2.85 (m, 2H, 2H from CH$_2$); 4.25 (m, 1H, 1H from CH$_2$—O); 4.40 (m, 1H, 1H from CH$_2$—O; 5.70 (br, 1H, CH); 5.85 (br, 1H, NH); 6.80 (m, 1H, Ar—H); 7.10 (m, 1H, Ar—H); 7.20 (m, 1H, Ar—H); 8.70 + 8.90 (2s, 1H, Pyr-6H); |
| 2.91 | oily; logp (HCOOH): 2.62; 1H-NMR (CDCl$_3$, 400 MHZ, δ in ppm): 1.25 (m, 1H, 1H from CH$_2$); 1.90 (m, 1H, 1H from CH$_2$); 2.15 (m, 2H, 2H from CH$_2$); 2.55 (q, 2H, 2H from CH$_2$); 2.70 (m, 1H, 1H from CH$_2$); 2.80-3.05 (m, 3H, 2H from CH$_2$, 1H from CH$_2$); 5.70 (br, 2H, CH, NH); 7.15-7.30 (m, 4H, Ar—H); 8.80 + 8.95 (2s, 1H, Pyr-6H); |
| 2.92 | oily; logp (HCOOH): 4.05; 1H-NMR (CDCl$_3$, 400 MHZ, δ in ppm): 1.95 (m, 3H, 2H from CH$_2$, 1H from CH$_2$); 2.15 (m, 1H, 1H from CH$_2$); 2.70-2.90 (m, 5H, 2*2H from CH$_2$, 1H from CH$_2$); 3.00-3.15 (m, 2H, 2*1H from CH$_2$); 3.50 (m, 1H, 1H from CHPh), 5.45 (m, 1H, CH); 5.85 (br, 1H, NH); 7.00-7.30 (m, 7H, Ar—H); 8.85 + 9.00 (2s, 1H, Pyr-6H); |
| 2.93 | oily; logp (HCOOH): 4.38; 1H-NMR (CDCl$_3$, 400 MHZ, δ in ppm): 1.95 (m, 3H, 2H from CH$_2$, 1H from CH$_2$); 2.15 (m, 1H, 1H from CH$_2$); 2.70-2.90 (m, 5H, 2*2H from CH$_2$, 1H from CH$_2$); 3.00-3.15 (m, 2H, 2*1H from CH$_2$); 3.75 (m, 1H, 1H from CHPh), 5.45 (m, 1H, CH); 5.95 (br, 1H, NH); 7.00-7.30 (m, 7H, Ar—H); 8.85 + 9.00 (2s, 1H, Pyr-6H); |
| 2.94 | oily; logp (HCOOH): 2.97; 1H-NMR (CDCl$_3$, 400 MHZ, δ in ppm): 1.10 (s, 6H, 2*CH$_3$); 2.15 (m, 1H, 1H from CH$_2$); 2.30 (m, 1H, 1H from CH$_2$); 2.45 (s, 2H, 2H from CH$_2$);, 2.65 (m, 1H, 1H from CH$_2$); 2.80 (m, 1H, 1H from CH$_2$); 4.25 (m, 2H, 2H from CH$_2$—O); 5.35 (m, 1H, CH); 5.85 (br, 1H, NH); 6.90 (m, 2H, Ar—H); 7.25 (m, 2H, Ar—H); 8.80 + 8.95 (2s, 1H, Pyr-6H); |
| 2.95 | oily; logp (HCOOH): 4.02; 1H-NMR (CDCl$_3$, 400 MHZ, δ in ppm): 1.10 (s + d, 9H, 2*CH$_3$, CH$_3$); 1.75 (m, 1H, 1H from CH$_2$); 1.95 (m, 2H, 21H from CH$_2$); 2.45 (s, 2H, 2H from CH$_2$); 2.65 (m, 1H, 1H from CH$_2$); 2.75 (m, 1H, 1H from CH$_2$); 2.85 (s, 2H, 2H from CH$_2$); 5.15 (m, 1H, CH); 5.65 (br, 1H, NH); 7.05-7.30 (m, 4H, Ar—H); 8.80 + 8.95 (2s, 1H, Pyr-6H); |
| 2.96 | oily; logp (HCOOH): 3.71; 1H-NMR (CDCl$_3$, 400 MHZ, δ in ppm): ): 1.95 (m, 3H, 2H from CH$_2$, 1H from CH$_2$); 2.15 (m, 1H, 1H from CH$_2$); 2.60 (m, 1H, 1H from CH$_2$); 2.75-3.15 (m, 7H, 3*2H from CH$_2$, 1H from CH$_2$); 5.40 (m, 1H, CH); 5.95 (br, 1H, NH); 7.05-7.30 (m, 4H, Ar—H); 8.80 + 9.00 (2s, 1H, Pyr-6H); |
| 2.97 | oily; logp (HCOOH): 3.26; 1H-NMR (CDCl$_3$, 400 MHZ, δ in ppm): ): 1.25 (t, 3H, CH$_3$); 2.30 (m + s, 4H, 3H, CH$_3$, 1H from CH$_2$); 2.55 (m, 1H, 1H from CH$_2$); 3.10 (m, 3H, 1H from CH$_2$); 4.30 (s, 2H, 2H from CH$_2$—O); 4.65 (s, 1H, 1H from CH$_2$); 4.75 (s, 1H, 2H from CH$_2$); 5.40 (m, 1H, CH); 5.85 (br, 1H, NH); 7.00-7.15 (m, 3H, Ar—H); 8.85-8.95 (2s, 1H, Pyr-6H); |
| 2.99 | oily; logp (HCOOH): 4.86; 1H-NMR (CDCl$_3$, 400 MHZ, δ in ppm): ): 1.25 (t, 3H, CH$_3$); 1.50 (m, 2H, 2H from CH$_2$); 1.70 (m, 2H, 2H from CH$_2$); 2.30 (m + s, 4H, 3H, CH$_3$, 1H from CH$_2$); 2.55 (m, 3H, 1H from CH$_2$, 2H from CH$_2$); 2.85 (m, 2H, 2H from CH$_2$); 3.10 (m, 3H, 1H from CH$_2$); 5.40 (m, 1H, CH); 5.65 (br, 1H, NH); 7.00-7.15 (m, 3H, Ar—H); 8.85 + 8.95 (2s, 1H, Pyr-6H); |
| 2.100 | solid; m.p.: 168.4° C.; logp (HCOOH): 2.80; 1H-NMR (CDCl$_3$, 400 MHZ, δ in ppm): 2.15 (m, 3H, 2H from CH$_2$, 1H from CH$_2$); ); 2.20 (s, 3H, 3H from CH$_3$); 2.25 (m, 1H, 1H from CH$_2$); 2.55 (q, 2H, 2H from CH$_2$); 2.70-2.85 (m, 2H, 2H from CH$_2$); 4.25 (m, 1H, 1H from CH$_2$—O); 4.35 (m, 1H, 1H from CH$_2$—O); 5.70 (br, 1H, CH); 5.95 (br, 1H, NH); 6.80 (m, 1H, Ar—H); 7.10 (m, 2H, Ar—H); 8.80 + 8.95 (2s, 1H, Pyr-6H); |
| 2.101 | oily; logp (HCOOH): 3.00; 1H-NMR (CDCl$_3$, 400 MHZ, δ in ppm): 1.90 (m, 7H, 1H from CH$_2$, 3*2H from CH$_2$); 2.35 (br, 3H, CH$_3$); 2.70 (m, s, 3H, 1H from CH$_2$, 2H from CH$_2$); 2.80-3.05 (m, 4H, 2*2H from CH$_2$); 5.65 (br, 2H, 1H from CH, 1H from NH); 6.85 (m, 2H, Ar—H); 7.25 (m, 1H, Ar—H); 8.80 + 8.95 (2s, 1H, Pyr-6H); |
| 2.102 | oily; |
| 2.103 | oily; |
| 2.104 | oily; |
| 2.105 | oily; logp (HCOOH): 4.14; 1H-NMR (CDCl$_3$, 400 MHZ, δ in ppm): ): 1.25 (t, 3H, CH$_3$); 1.50 (m, 2H, 2H from CH$_2$); 1.70 (m, 2H, 2H from CH$_2$); 2.30 (m + s, 4H, 3H, CH$_3$, 1H from CH$_2$); 2.55 (m, 3H, 1H from CH$_2$, 2H from CH$_2$); 2.85 (m, 2H, 2H from CH$_2$); 3.10 (m, 3H, 1H from CH$_2$); 5.40 (m, 1H, CH); 5.65 (br, 1H, NH); 7.05-7.15 (m, 3H, Ar—H) ; 8.80 + 8.95 (2s, 1H, Pyr-6H); |
| 2.106 | oily; logp (HCOOH): 3.90; 1H-NMR (CDCl$_3$, 400 MHZ, δ in ppm): 0.95 (t, 3H, CH$_3$); 1.80 (m, 1H, 1H from CH$_2$); 2.15 (m, 3H, 2H from CH$_2$, 1H from CH$_2$), 2.30 (br, 3H, CH$_3$); 2.50-2.60 (m, 3H, 1H from CH$_2$, 2H from CH$_2$), 2.80 (m, 2H, 2H from CH$_2$); 3.05 (m, 1H, 1H from CH$_2$); 5.50 (br, 1H, 1H from CH), 5.50 (br, 1H, 1H from NH); 7.00-7.15 (m, 3H, Ar—H); 8.80 + 8.95 (2s, 1H, Pyr-6H); |
| 2.107 | oily; logp (HCOOH): 3.83; 1H-NMR (CDCl$_3$, 400 MHZ, δ in ppm): 1.20 (d, 6H, 2*CH$_3$); 1.90 (m, 1H, 1H from CH$_2$); 2.10 (m, 2H, 2H from CH$_2$); 2.60 (m, 2H, 2H from CH$_2$); 2.70 (m, 2H, 2H from CH$_2$); 2.80-3.00 (m, 4H, 1H from CH(CH$_3$)$_2$, 1H from CH$_2$, 2H from CH$_2$); 5.65 (br, 2H, 1H from CH) 5.80 (br, 1H, 1H from NH); 7.10-7.25 (m, 3H, Ar—H); 8.80 + 8.95 (2s, 1H, Pyr-6H); |
| 2.108 | oily; logp (HCOOH): 3.58; 1H-NMR (CDCl$_3$, 400 MHZ, δ in ppm): 1.25 (d, 3H, CH$_3$); 2.15 (m, 2H, 2H from CH$_2$); 2.55 (m, 3H, 1H from CH$_2$, 2H from CH$_2$); 2.70 (m, 2H, 2H from CH$_2$); 3.10 (m, 1H, 1H from CH$_2$); 5.35 (br, 2H, 1H from CH) 5.80 (br, 1H, 1H from NH); 7.20-7.25 (m, 3H, Ar—H) 8.80 + 8.95 (2s, 1H, Pyr-6H); |

TABLE 3-continued (physicochemical characterization of selected synthesis examples)

Compound Description 2.109 solid; m.p.: 151.3° C.; logp (HCOOH): 2.83; 1H-NMR (CDCl$_3$, 400 MHZ, δ in ppm):
1.90 (m, 3H, 1H from CH$_2$, 2H from CH$_2$); 2.10 (m, 3H, 1H from CH$_2$, 2H from CH$_2$);
2.55 (m, 2H, 2H from CH$_2$); 2.80-2.95 (m, 4H, 2*2H from CH$_2$); 3.80 (s, 3H, OCH$_3$),
5.40 (br, 1H, 1H from CH), 5.70 (br, 1H, 1H from NH); 6.65 (m, 1H, Ar—H), 6.75 (m,
1H, Ar—H); 7.20 (m, 1H, Ar—H); 8.80 + 8.95 (2s, 1H, Pyr-6H);

2.110 oily; logp (HCOOH): 3.98

2.111 oily; logp (HCOOH): 3.37; 1H-NMR (CDCl$_3$, 400 MHZ, δ in ppm): 1.35 (d, 3H, 3H
from CH$_3$), 1.65 (m, 1H, 1H from CH$_2$); 2.10 (m, 4H, 2*1H from CH$_2$, 2H from CH$_2$);
2.55 (m, 2H, 2H from CH$_2$); 2.75-2.95 (m, 4H, 2*2H from CH$_2$); 5.40 (br, 1H, 1H
from CH), 5.80 (br, 1H, 1H from NH); 7.10-7.35 (m, 4H, Ar—H), 8.80 + 8.95 (2s, 1H,
Pyr-6H);

2.112 oily; logp (HCOOH): 4.51; 1H-NMR (CDCl$_3$, 400 MHZ, δ in ppm):, 1.50 und 1.70 (br,
je 4H, je 2*2H from CH$_2$); 1.90 (m, 1H, 1H from CH$_2$); 2.30 (s, 3H, CH$_3$), 2.55 (m,
2H, 2H from CH$_2$); 2.70 (m, 2H, 2*1H from CH$_2$); 2.80-2.95 (m, 3H, 3*1H from
CH$_2$); 5.70 (br, 1H, 1H from CH), 5.90 (br, 1H, 1H from NH); 7.10-7.20 (m, 3H,
Ar—H), 8.80 + 8.95 (2s, 1H, Pyr-6H);

2.113 solid; m.p.: 168.2° C.; logp (HCOOH): 3.41; 1H-NMR (CDCl$_3$, 400 MHZ, δ in ppm):
1.20 (d, 6H, 2*3H from CH(CH$_3$)$_2$), 2.15 (m, 3H, 2H from CH$_2$, 1H from CH$_2$); ); 2.25
(m, 1H, 1H from CH$_2$); 2.55 (m, 2H, 2H from CH$_2$); 2.70-2.85 (m, 3H, 1H from CH$_2$,
2H from CH$_2$); 4.25 (m, 1H, 1H from CH$_2$—O); 4.30 (m, 1H, 1H from CH$_2$—O); 5.30
(br, 1H, CH); 5.90 (br, 1H, NH); 6.80 (m, 1H, Ar—H); 7.10 (m, 2H, Ar—H); 8.80 +
8.95 (2s, 1H, Pyr-6H);

2.114 oily; logp (HCOOH): 2.77; 1H-NMR (CDCl$_3$, 400 MHZ, δ in ppm): 2.10 (m, 2H, 2H
from CH$_2$); 2.20 (m, 1H, 1H from CH$_2$); 2.40 (m, 1H, 1H from CH$_2$); 2.60 (m, 2H, 2H
from CH$_2$); 2.75-2.95 (m, 2H, 2*1H from CH$_2$), 3.00-3.15 (m, 2H, 2*1H from CH$_2$);
5.40 (br, 1H, 1H from CH), 5.90 und 6.15 (br, 1H, 1H from NH); 6.90 (m, 1H, Ar—H),
7.05 (m, 1H, Ar—H); 7.15 (m, 1H, Ar—H); 8.80 + 8.95 (2s, 1H, Pyr-6H);

2.115 oily;

2.116 solid; m.p.: 141.6° C.; logp (HCOOH): 2.90; 1H-NMR (CDCl$_3$, 400 MHZ, δ in ppm):
1.40 und 1.45 (s, 2*3H, 2*3H from CH$_3$), 1.80 ( m, 1H, 1H from CH$_2$); 2.15 (m, 2H,
2H from CH$_2$); 2.30 (m, 1H, 1H from CH$_2$); 2.55 (m, 2H, 2H from CH$_2$); 2.70-2.85
(m, 2H,, 2H from CH$_2$); 5.40 (br, 1H, CH); 5.60 (br, 1H, NH); 6.40 (m, 1H, Ar—H);
6.50 (m, 1H, Ar—H); 7.15 (m, 1H, Ar—H); 8.80 + 8.95 (2s, 1H, Pyr-6H);

2.117 oily; logp (HCOOH): 2.52; 1H-NMR (CDCl$_3$, 400 MHZ, δ in ppm): 2.10 (m, 2H, 2H
from CH$_2$); 2.30 (s, 3H, 3H from CH$_3$); 2.60 (m, 2H, 2H from CH$_2$); 2.75-2.95 (m,
2H, 2*1H from CH$_2$), 4.25 (m, 1H, 1H from CH$_2$); 4.80 (m, 1H, 1H from CH$_2$); 5.75
(br, 1H, 1H from CH), 5.80 (br, 1H, 1H from NH); 6.80 (m, 1H, Ar—H), 7.05 (m, 1H,
Ar—H); 7.15 (m, 1H, Ar—H); 8.80 + 8.95 (2s, 1H, Pyr-6H);

2.118 oily; logp (HCOOH): 4.51; 1H-NMR (CDCl$_3$, 400 MHZ, δ in ppm): 1.25 (d, 3H, 3H
from CH$_3$); 1.85-2.00 (m, 6H, 3*2H from CH$_2$); 2.30 (s, m, 4H, 3H from CH$_3$, 1H
from CH$_2$); 2.50 (m, 1H, 1H from CH$_2$); 2.70 (s, 2H, 2H from CH$_2$); 2.90 (2s, 2H, 2H
from CH$_2$); 3.05 (m, 1H, 1H from CH$_2$), 5.40 (br, 1H, 1H from CH), 5.70 (br, 1H, 1H
from NH); 7.00-7.15 (m, 3H, Ar—H), 8.80 + 8.95 (2s, 1H, Pyr-6H);

B. Formulation Examples a) A dusting product is obtained by mixing 10 parts by weight of a compound of the formula (I) and/or salts thereof and 90 parts by weight of talc as an inert substance and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.), and grinding the mixture in a friction ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing 75 parts by weight of a compound of the formula (I) and/or salts thereof, 10 parts by weight of calcium lignosulfonate, 5 parts by weight of sodium lauryl sulfate, 3 parts by weight of polyvinyl alcohol and 7 parts by weight of kaolin, grinding the mixture in a pinned-disk mill, and granulating the powder in a fluidized bed by spray application of water as a granulating liquid.

f) Water-dispersible granules are also obtained by homogenizing and precomminuting, in a colloid mill, 25 parts by weight of a compound of the formula (I) and/or salts thereof, 5 parts by weight of sodium 2,2'-dinaphthylmethane-6,6'-disulfonate 2 parts by weight of sodium oleoylmethyltaurate, 1 part by weight of polyvinyl alcohol 17 parts by weight of calcium carbonate and 50 parts by weight of water, then grinding the mixture in a bead mill and atomizing and drying the resulting suspension in a spray tower by means of a one-phase nozzle.

C. Biological Examples

Test Description

1. Pre-Emergence Herbicidal Effect and Crop Plant Compatibility

Seeds of monocotyledonous and dicotyledonous weed plants and crop plants are laid out in wood-fiber pots in sandy loam and covered with soil. The compounds of the invention, formulated in the form of wettable powders (WP) or as emulsion concentrates (EC), are then applied to the surface of the covering soil as aqueous suspension or emulsion at a water application rate equating to 600 to 800 L/ha with addition of 0.2% wetting agent.

After the treatment, the pots are placed in a greenhouse and kept under good growth conditions for the trial plants. The damage to the trial plants is scored visually after a trial duration of 3 weeks by comparison with untreated controls (herbicidal activity in percent (%): 100% efficacy=the plants have died, 0% efficacy=like control plants).

In the tables below, the following abbreviations are used:

| Crops: | | | |
|---|---|---|---|
| BRSNW: | *Brassica napus* | ORYSA: | *Oryza sativa* |
| TRZAS: | *Triticum aestivum* (spring) | ZEAMX: | *Zea mays* |

| Undesired plants/weeds: | | | |
|---|---|---|---|
| ABUTH: | *Abutilon theophrasti* | ALOMY: | *Alopecurus myosuroides* |
| AMARE: | *Amaranthus retroflexus* | AVEFA: | *Avena fatua* |
| CYPES: | *Cyperus esculentus* | ECHCG: | *Echinochloa crus-galli* |
| LOLMU: | *Lolium multiflorum* | MATIN: | *Matricaria inodora* |
| PHBPU: | *Ipomoea purpurea* | POLCO: | *Polygonum convolvulus* |
| SETVI: | *Setaria viridis* | STEME: | *Stellaria media* |
| VERPE: | *Veronica persica* | VIOTR: | *Viola tricolor* |

TABLE 4

(pre-emergence efficacy):

| Ex. No | Dosage | Unit | ORYSA | TRZAS | ZEAMX | ALOMY | AVEFA | CYPES | ECHCG | LOLMU |
|---|---|---|---|---|---|---|---|---|---|---|
| 1.3 | 320 | g/ha | | 20 | | | | | 100 | |
| 1.3 | 80 | g/ha | 20 | 20 | 20 | | | | 80 | |
| 1.4 | 320 | g/ha | | | | 100 | 100 | 100 | 90 | |
| 1.4 | 80 | g/ha | | | | 100 | 100 | 80 | | |
| 1.7 | 320 | g/ha | | 0 | 20 | 100 | | | 90 | 100 |
| 1.7 | 80 | g/ha | | 0 | 0 | 80 | | | | |
| 1.8 | 320 | g/ha | | 0 | 0 | 0 | | | 90 | |
| 1.8 | 80 | g/ha | | 0 | 0 | 0 | | | | |
| 1.10 | 320 | g/ha | | 20 | | 80 | | | 100 | 100 |
| 1.10 | 80 | g/ha | | 0 | 0 | | | | 100 | |
| 1.20 | 1280 | g/ha | | | 0 | | | | | |
| 1.20 | 320 | g/ha | | 20 | 0 | | | | | |
| 1.26 | 320 | g/ha | | | 0 | 90 | | 80 | 100 | 100 |
| 1.26 | 80 | g/ha | | 0 | 0 | 90 | | 80 | 100 | 80 |
| 1.82 | 320 | g/ha | 3 | 0 | | | | | | |
| 1.82 | 80 | g/ha | 0 | 0 | 0 | | | | | |
| 1.83 | 1280 | g/ha | | | | 100 | 90 | | 100 | 100 |
| 1.85 | 320 | g/ha | | | | 80 | 100 | | 90 | 90 |
| 1.85 | 80 | g/ha | | | | | | | 90 | |
| 1.86 | 320 | g/ha | 10 | 10 | 0 | | | | 100 | |
| 1.86 | 80 | g/ha | 0 | 0 | 0 | | | | | |
| 1.87 | 320 | g/ha | | 0 | 10 | | | | 100 | |
| 1.87 | 80 | g/ha | 0 | 0 | 0 | | | | | |
| 1.88 | 320 | g/ha | | 0 | 0 | | | | | |
| 1.88 | 80 | g/ha | 0 | 0 | 0 | | | | | |
| 1.89 | 320 | g/ha | 0 | 0 | 0 | | | | | |
| 1.89 | 80 | g/ha | | 0 | 0 | | | | | |
| 1.90 | 1280 | g/ha | 20 | 0 | 20 | | 100 | | 80 | |
| 1.90 | 320 | g/ha | 20 | 0 | 20 | | | | | |
| 1.92 | 320 | g/ha | 0 | 0 | 20 | | | | | |
| 1.92 | 80 | g/ha | | 0 | 20 | | | | | |
| 2.13 | 320 | g/ha | | 10 | | 100 | 90 | 100 | 100 | 100 |
| 2.13 | 80 | g/ha | | 0 | 0 | | | 100 | 100 | |
| 2.19 | 320 | g/ha | | 0 | 10 | 100 | 90 | | 100 | 100 |
| 2.23 | 320 | g/ha | | | | 100 | 90 | 90 | 100 | 100 |
| 2.23 | 80 | g/ha | 5 | 0 | 0 | 80 | | | 80 | 80 |
| 2.25 | 320 | g/ha | 0 | | 0 | | | | 100 | |
| 2.25 | 80 | g/ha | 0 | 0 | 0 | | | | | |
| 2.26 | 320 | g/ha | | | | 90 | 90 | | 100 | 100 |
| 2.26 | 80 | g/ha | | 0 | 0 | | | | 80 | |
| 2.43 | 320 | g/ha | | | | 100 | 100 | 80 | 100 | 100 |
| 2.43 | 80 | g/ha | | 0 | 20 | 100 | | | 100 | 100 |
| 2.44 | 320 | g/ha | | | | 100 | 80 | | 100 | 100 |
| 2.44 | 80 | g/ha | 20 | | 10 | 80 | 0 | | 90 | 100 |
| 2.45 | 320 | g/ha | 10 | | | 90 | 80 | | 100 | 100 |
| 2.45 | 80 | g/ha | 0 | | 10 | | | | 100 | 80 |
| 2.46 | 320 | g/ha | | 0 | 0 | 90 | | | 100 | 100 |
| 2.46 | 80 | g/ha | | 0 | 0 | 90 | | | 90 | 100 |

TABLE 4-continued (pre-emergence efficacy):

| | | | | | | | | | | |
|---|---|---|---|---|---|---|---|---|---|---|
| 2.50 | 1280 | g/ha | | | 0 | | | | | |
| 2.50 | 320 | g/ha | | | 0 | | | | | |
| 2.52 | 320 | g/ha | 20 | 30 | 10 | | | | 100 | 90 |
| 2.52 | 80 | g/ha | 0 | 0 | 0 | | | | | |
| 2.91 | 320 | g/ha | 20 | | 20 | 90 | 80 | | 100 | 100 |
| 2.92 | 320 | g/ha | 20 | 20 | 20 | | | | 100 | |
| 2.92 | 80 | g/ha | 0 | 0 | 0 | | | | | |
| 2.93 | 1280 | g/ha | 20 | 0 | 0 | | | 100 | | |
| 2.94 | 320 | g/ha | 0 | 0 | 0 | 80 | | | 100 | 90 |
| 2.95 | 80 | g/ha | | 0 | 0 | | | | | |
| 2.95 | 320 | g/ha | 0 | 0 | 0 | | | | 80 | |
| 2.95 | 80 | g/ha | 0 | 0 | 0 | | | | | |
| 2.96 | 320 | g/ha | 0 | 0 | 10 | 80 | | | 100 | 90 |
| 2.96 | 80 | g/ha | | 0 | 0 | | | | | |
| 2.97 | 320 | g/ha | | 20 | | 100 | 100 | | 100 | 100 |
| 2.97 | 80 | g/ha | | 10 | 0 | 100 | | | 100 | |
| 2.99 | 320 | g/ha | 10 | 20 | 10 | | 80 | | 100 | 80 |
| 2.99 | 80 | g/ha | 0 | 10 | 0 | | | | | |
| 2.100 | 320 | g/ha | | 10 | 10 | 80 | | | 100 | 100 |
| 2.100 | 80 | g/ha | | 0 | 0 | | | | 100 | |
| 2.101 | 320 | g/ha | | 0 | 10 | | 80 | | 100 | 100 |
| 2.101 | 80 | g/ha | | 0 | 10 | | | | | |
| 2.102 | 320 | g/ha | 0 | 0 | 0 | 100 | | | 100 | 100 |
| 2.102 | 80 | g/ha | 0 | 0 | 0 | | | | | |
| 2.103 | 320 | g/ha | 0 | 0 | 0 | 80 | | | 100 | 90 |
| 2.103 | 80 | g/ha | 0 | 0 | 0 | | | | 90 | |
| 2.104 | 320 | g/ha | 20 | | 0 | | | | | 90 |
| 2.104 | 80 | g/ha | 20 | 0 | 0 | | | | | |
| 2.117 | 320 | g/ha | 0 | 0 | 20 | | | | | |
| 2.118 | 320 | g/ha | 10 | | 0 | 90 | | | 100 | 100 |
| 2.118 | 80 | g/ha | 10 | 0 | 0 | | | | | 80 |

| Ex. No | SETVI | ABUTH | AMARE | MATIN | PHBPU | POLCO | STEME | VERPE | VIOTR |
|---|---|---|---|---|---|---|---|---|---|
| 1.3 | 80 | | 100 | 100 | | 100 | 90 | 100 | |
| 1.3 | | | 100 | 90 | | 80 | | 100 | |
| 1.4 | 90 | | 100 | 100 | 100 | 100 | 100 | 100 | 100 |
| 1.4 | | | 100 | 100 | | 100 | 90 | 100 | 100 |
| 1.7 | 90 | | 100 | 100 | 100 | 90 | 100 | 100 | 100 |
| 1.7 | | | | 90 | | | 80 | 100 | |
| 1.8 | 80 | | 100 | 100 | | | | 100 | 100 |
| 1.8 | | | 100 | | | | | | |
| 1.10 | 100 | 80 | 100 | 100 | | | 100 | 100 | 100 |
| 1.10 | 100 | | 100 | 100 | | | 100 | 100 | 100 |
| 1.20 | | | 100 | 100 | | 100 | 100 | 100 | 100 |
| 1.20 | | | 90 | 90 | | | 100 | 100 | 90 |
| 1.26 | 100 | | 100 | 100 | | 100 | 100 | 100 | 100 |
| 1.26 | 100 | | 100 | 100 | | 100 | 100 | 100 | 100 |
| 1.82 | | | 90 | 90 | | 80 | 100 | 100 | 100 |
| 1.82 | | | 90 | 90 | | | | 100 | 100 |
| 1.83 | 100 | 100 | 100 | 100 | 100 | 100 | 100 | 100 | 100 |
| 1.85 | 90 | | 100 | 90 | | 80 | 100 | 100 | 100 |
| 1.85 | | | 80 | 80 | | | 100 | 100 | 100 |
| 1.86 | 100 | | 100 | 100 | | | 100 | 100 | 100 |
| 1.86 | | | | | | | 100 | 100 | 80 |
| 1.87 | 100 | | 100 | 100 | | | 100 | 100 | 100 |
| 1.87 | | | 80 | 90 | | | | | 100 |
| 1.88 | | | 100 | 100 | | | 100 | 100 | 90 |
| 1.88 | | | 80 | 100 | | | | 100 | |
| 1.89 | | | 100 | 100 | | | 80 | 100 | 100 |
| 1.89 | | | | 100 | | | 80 | 80 | 90 |
| 1.90 | | | 100 | 100 | | 90 | 100 | 100 | 100 |
| 1.90 | | | 90 | 100 | | | 80 | 100 | |
| 1.92 | | | 100 | 100 | | | | 100 | 100 |
| 1.92 | | | 100 | | | | | 100 | |
| 2.13 | | | 100 | 100 | | 100 | 100 | 100 | 100 |
| 2.13 | 100 | | 100 | 100 | | 100 | 100 | 100 | 100 |
| 2.19 | 100 | | 100 | 100 | | 100 | 100 | 100 | 100 |
| 2.23 | 100 | | 100 | 100 | | 100 | 100 | 100 | 100 |
| 2.23 | 100 | | 100 | 100 | | 100 | 100 | 100 | 100 |
| 2.25 | 100 | | 100 | 100 | | 100 | 100 | 100 | 100 |
| 2.25 | | | 90 | 90 | | | 100 | 100 | 100 |
| 2.26 | 90 | | 100 | 100 | | 100 | 100 | 100 | 100 |
| 2.26 | | | 100 | | | | 100 | 80 | 90 |
| 2.43 | 100 | 100 | 100 | 100 | | 100 | 100 | 100 | 100 |
| 2.43 | 90 | | 100 | 100 | | 100 | 100 | 100 | 100 |
| 2.44 | 100 | | 100 | 100 | | 100 | 100 | 100 | 100 |

TABLE 4-continued (pre-emergence efficacy):

| | | | | | | | | |
|---|---|---|---|---|---|---|---|---|
| 2.44 | 100 | | 100 | 90 | | 90 | 100 | 100 | 100 |
| 2.45 | 100 | 80 | 100 | 90 | 90 | 100 | 100 | 100 | 100 |
| 2.45 | 100 | 80 | 100 | 90 | | 100 | 100 | 100 | 100 |
| 2.46 | 90 | 80 | 100 | 100 | | 100 | 100 | 100 | 100 |
| 2.46 | 90 | | 90 | 90 | | | 100 | 100 | 100 |
| 2.50 | 80 | | 100 | | | | 100 | 100 | 90 |
| 2.50 | | | | | | | 100 | 100 | 90 |
| 2.52 | 70 | 0 | 100 | 100 | | 60 | 100 | 100 | 100 |
| 2.52 | | | | | | | | 90 | 100 |
| 2.91 | 100 | 100 | 100 | 100 | 100 | 80 | 100 | 100 | 100 |
| 2.92 | 100 | | 100 | 90 | | | 100 | 100 | 100 |
| 2.92 | | | 80 | | | | 100 | 100 | 90 |
| 2.93 | | | 80 | | 90 | | 100 | 100 | 80 |
| 2.94 | 90 | | 100 | 100 | | 100 | 100 | 100 | 100 |
| 2.95 | | | 100 | 90 | | | 100 | 100 | 90 |
| 2.95 | | | 100 | 90 | | | 100 | 100 | 100 |
| 2.95 | | | | 90 | | | 100 | 100 | 100 |
| 2.96 | 90 | | 100 | 90 | | 80 | 100 | 100 | 100 |
| 2.96 | | | 100 | | | | 100 | 100 | 100 |
| 2.97 | 100 | | 100 | 100 | | 100 | 100 | 100 | 100 |
| 2.97 | 100 | | 100 | 100 | | 100 | 100 | 100 | 100 |
| 2.99 | 100 | | 100 | 100 | | 100 | 100 | 100 | 100 |
| 2.99 | | | 90 | 90 | | | 90 | 100 | 100 |
| 2.100 | 100 | 90 | 100 | 100 | | 90 | 100 | 100 | 100 |
| 2.100 | 100 | | 100 | 100 | | 90 | 100 | 100 | 100 |
| 2.101 | 100 | | 100 | 100 | | 100 | 100 | 100 | 100 |
| 2.101 | 100 | | 100 | 100 | | | 100 | 100 | 100 |
| 2.102 | 100 | | 100 | 100 | | 90 | 100 | 100 | 100 |
| 2.102 | 100 | | 80 | 90 | | | 100 | 100 | 100 |
| 2.103 | | | 100 | 100 | | | 100 | 100 | 100 |
| 2.103 | | | 100 | 100 | | | 100 | 100 | |
| 2.104 | 100 | | 100 | 100 | | 100 | 100 | 100 | 100 |
| 2.104 | | | | 80 | | | 100 | 100 | 90 |
| 2.117 | | 80 | | 100 | | | | | |
| 2.118 | 100 | | 100 | 100 | | 100 | 100 | 100 | 100 |
| 2.118 | 100 | | 100 | 90 | | | 100 | 100 | 100 |

As shown by the results, the compounds of the invention have good herbicidal pre-emergence activity against a broad spectrum of weed grasses and broad-leaved weeds. For example, the compounds from table 1 have very good herbicidal activity against harmful plants such as *Avena fatua, Stellaria media, Echinochloa crus-galli, Lolium multiflorum, Setaria viridis, Abutilon theophrasti, Amaranthus retroflexus* and *Alopecurus myosuroides* when applied by the pre-emergence method at an application rate of 1.28 kg or less of active substance per hectare. The compounds of the invention are therefore suitable for control of unwanted plant growth by the pre-emergence method.

2. Post-Emergence Herbicidal Effect and Crop Plant Compatibility

Seeds of monocotyledonous and dicotyledonous weed and crop plants are laid out in sandy loam in wood-fiber pots, covered with soil and cultivated in a greenhouse under good growth conditions. 2 to 3 weeks after sowing, the test plants are treated at the one-leaf stage. The compounds of the invention, formulated in the form of wettable powders (WP) or as emulsion concentrates (EC), are then sprayed onto the green parts of the plants as aqueous suspension or emulsion at a water application rate equating to 600 to 800 L/ha with addition of 0.2% wetting agent. After the trial plants have been left to stand in a greenhouse under optimal growth conditions for about 3 weeks, the efficacy of the formulations is scored visually in comparison to untreated controls (herbicidal action in percent (%): 100% efficacy=the plants have died, 0% efficacy=like control plants).

TABLE 5

(post-emergence efficacy):

| Ex. No | Dosage | Unit | ORYSA | TRZAS | ZEAMX | BRSNW | ALOMY | AVEFA | ECHCG | LOLMU |
|---|---|---|---|---|---|---|---|---|---|---|
| 1.10 | 320 | g/ha | | | | | | | 90 | |
| 1.10 | 80 | g/ha | | 20 | | | | | | |
| 1.26 | 320 | g/ha | 0 | | 0 | | 90 | 80 | 100 | 80 |
| 1.26 | 80 | g/ha | 0 | 0 | 0 | | | | 90 | |
| 1.82 | 320 | g/ha | | 0 | | | | | | |
| 1.85 | 320 | g/ha | 20 | 20 | 20 | | | | 90 | |
| 1.85 | 80 | g/ha | 20 | 10 | 0 | | | | | |
| 1.86 | 320 | g/ha | 0 | 0 | 0 | | | | | |
| 1.86 | 80 | g/ha | 0 | 0 | 0 | | | | | |
| 1.88 | 320 | g/ha | 0 | 20 | 10 | | | | | |
| 1.88 | 80 | g/ha | 0 | 0 | 0 | | | | | |

TABLE 5-continued (post-emergence efficacy):

| | | | | | | | | | |
|---|---|---|---|---|---|---|---|---|---|
| 2.13 | 320 | g/ha | 0 | 20 | | | 90 | | 100 |
| 2.13 | 80 | g/ha | 0 | 10 | 10 | | | | 90 |
| 2.19 | 320 | g/ha | 20 | 20 | | | | 100 | 100 |
| 2.23 | 320 | g/ha | 20 | 0 | | | 100 | 90 | 100 |
| 2.23 | 80 | g/ha | 20 | 0 | 0 | | | | |
| 2.25 | 320 | g/ha | 0 | 20 | 0 | | | | |
| 2.25 | 80 | g/ha | 0 | 10 | 0 | | | | |
| 2.26 | 320 | g/ha | 0 | 0 | 0 | | | | |
| 2.26 | 80 | g/ha | 0 | 0 | 0 | 20 | | | |
| 2.43 | 320 | g/ha | | 10 | | | 100 | 90 | 100 |
| 2.43 | 80 | g/ha | 10 | 10 | 0 | | | 90 | 80 |
| 2.44 | 320 | g/ha | 0 | 0 | | | 90 | 100 | |
| 2.44 | 80 | g/ha | 0 | 0 | 10 | | | 100 | |
| 2.45 | 320 | g/ha | | 10 | 0 | 80 | 80 | 100 | 100 |
| 2.45 | 80 | g/ha | 20 | 10 | 0 | | | 100 | |
| 2.46 | 320 | g/ha | 20 | 10 | 0 | 100 | | | 100 |
| 2.46 | 80 | g/ha | 10 | 10 | 0 | | | | 80 |
| 2.52 | 320 | g/ha | 0 | 0 | 0 | | | | |
| 2.52 | 80 | g/ha | 0 | 0 | 0 | 20 | | | |
| 2.91 | 320 | g/ha | 0 | | | | | 100 | 100 |
| 2.92 | 320 | g/ha | 0 | 10 | 0 | | | | |
| 2.92 | 80 | g/ha | 0 | 0 | 0 | | | | |
| 2.94 | 320 | g/ha | 0 | 20 | 0 | | | | |
| 2.94 | 80 | g/ha | 0 | 10 | 0 | | | | |
| 2.96 | 320 | g/ha | 0 | 20 | 10 | | | | |
| 2.96 | 80 | g/ha | 0 | 10 | 0 | | | | |
| 2.97 | 320 | g/ha | | 0 | | 100 | | 100 | 100 |
| 2.97 | 80 | g/ha | | 0 | | | | 90 | |
| 2.99 | 320 | g/ha | 0 | 0 | 0 | | 80 | 100 | 90 |
| 2.99 | 80 | g/ha | 0 | 0 | 0 | | | | |
| 2.100 | 320 | g/ha | 0 | 20 | 10 | | | 100 | 100 |
| 2.100 | 80 | g/ha | 0 | 10 | 10 | | | 100 | |
| 2.101 | 320 | g/ha | 0 | 0 | 0 | 100 | | 100 | |
| 2.101 | 80 | g/ha | 0 | 0 | 0 | | | | |
| 2.102 | 320 | g/ha | 0 | | 0 | | | 100 | |
| 2.102 | 80 | g/ha | 0 | 20 | 0 | | | | |
| 2.103 | 320 | g/ha | 0 | 20 | 0 | | | | 80 |
| 2.103 | 80 | g/ha | 0 | 10 | 0 | | | | |
| 2.104 | 320 | g/ha | 0 | 0 | 0 | | | | |
| 2.104 | 80 | g/ha | 0 | 0 | 0 | | | | |
| 2.118 | 320 | g/ha | 0 | 10 | | | | 100 | 80 |
| 2.118 | 80 | g/ha | 0 | 0 | 0 | | | | |

| Ex. No | SETVI | ABUTH | AMARE | MATIN | PHBPU | POLCO | STEME | VERPE | VIOTR |
|---|---|---|---|---|---|---|---|---|---|
| 1.10 | | 80 | 90 | | 90 | 90 | 80 | 100 | |
| 1.10 | | | 80 | | | 80 | | 90 | |
| 1.26 | 90 | | 100 | | 90 | 90 | | 90 | 90 |
| 1.26 | | | 80 | | | 90 | | 90 | 90 |
| 1.82 | | | | | | | | 90 | |
| 1.85 | | | 100 | | | 80 | 100 | 80 | |
| 1.85 | | | 90 | | | | 90 | 80 | |
| 1.86 | 90 | | 100 | | | | 100 | 100 | 90 |
| 1.86 | | | 90 | | | | 100 | 90 | 90 |
| 1.88 | | | 80 | | | | | 100 | |
| 1.88 | | | | | | | | 90 | |
| 2.13 | 100 | | 90 | 90 | 100 | | 100 | 90 | 90 |
| 2.13 | | | 90 | | | | 100 | 80 | |
| 2.19 | | | 100 | 100 | 80 | 90 | 100 | 90 | 80 |
| 2.23 | | 80 | 100 | | 80 | | 100 | 100 | |
| 2.23 | | | | | | | 80 | | |
| 2.25 | | | 100 | | 90 | 80 | 100 | 90 | 80 |
| 2.25 | | | 90 | | | | 90 | 90 | |
| 2.26 | | 80 | 80 | | | | | 90 | 80 |
| 2.26 | | 80 | 80 | | | | | 90 | |
| 2.43 | 80 | 80 | 100 | 80 | | 90 | 100 | 100 | 90 |
| 2.43 | | | 90 | | 80 | 90 | 100 | 90 | |
| 2.44 | | 80 | 100 | | 100 | 90 | 100 | | 100 |
| 2.44 | | | 90 | | 100 | 90 | 80 | | 90 |
| 2.45 | 90 | 100 | 100 | 90 | 100 | 80 | 100 | 100 | 100 |
| 2.45 | | 100 | 100 | 90 | 100 | 80 | 90 | 90 | 100 |
| 2.46 | | 80 | 100 | | | 90 | 100 | 90 | 100 |
| 2.46 | | 80 | 90 | | | | 100 | 80 | 100 |
| 2.52 | | | 100 | | | | | 80 | |
| 2.52 | | | 100 | | | | | 80 | |
| 2.91 | 90 | 100 | 100 | 100 | | 80 | 100 | 100 | 90 |
| 2.92 | | | 90 | | | | 80 | 90 | 90 |

TABLE 5-continued (post-emergence efficacy):

| | | | | | | | | | |
|---|---|---|---|---|---|---|---|---|---|
| 2.92 | | 80 | | | | | 80 | 90 | 90 |
| 2.94 | | | 90 | | 80 | 90 | | 90 | 100 |
| 2.94 | | | | | | | | 90 | 90 |
| 2.96 | | | 80 | | 80 | | 100 | 90 | 90 |
| 2.96 | | | | | | | 100 | 90 | 80 |
| 2.97 | 80 | 80 | 100 | 80 | 100 | 90 | 100 | 100 | 100 |
| 2.97 | | 80 | 100 | | | 80 | 80 | 100 | 90 |
| 2.99 | | | 100 | | 100 | 80 | 100 | 90 | 100 |
| 2.99 | | | 90 | | 100 | | 80 | 90 | 100 |
| 2.100 | 90 | | 100 | 90 | | 80 | 100 | 90 | |
| 2.100 | 90 | | 80 | | | | 100 | 90 | |
| 2.101 | | | 100 | | 80 | 80 | 100 | 80 | |
| 2.101 | | | 100 | | | | 100 | | |
| 2.102 | | | 100 | | | | 100 | 100 | 100 |
| 2.102 | | | 80 | | | | 90 | 90 | 80 |
| 2.103 | | | 100 | | | | 100 | 100 | 80 |
| 2.103 | | | 80 | | | | 100 | 80 | 80 |
| 2.104 | | | 80 | | | | 80 | 100 | 100 |
| 2.104 | | | 80 | | | | 80 | 90 | 90 |
| 2.118 | 80 | | 100 | | 100 | 90 | 100 | 90 | 100 |
| 2.118 | | | 90 | | | | 80 | 90 | 100 |

As the results show, inventive compounds have good herbicidal post-emergence efficacy against a broad spectrum of weed grasses and broad-leaved weeds. For example, the compounds from table 2 have very good herbicidal activity against harmful plants such as *Avena fatua*, *Stellaria media*, *Echinochloa crus-galli*, *Lolium multiflorum*, *Setaria viridis*, *Abutilon theophrasti*, *Amaranthus retroflexus* and *Alopecurus myosuroides* when applied by the post-emergence method at an application rate of 1.28 kg or less of active substance per hectare. The compounds of the invention are therefore suitable for control of unwanted plant growth by the post-emergence method.

The invention claimed is:

1. A compound of formula (I)

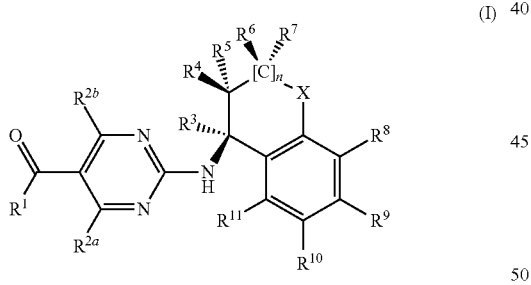

and/or an agrochemically acceptable salt thereof in which $R^1$ is selected from the group consisting of $(C_1-C_6)$-alkyl, $(C_1-C_6)$-haloalkyl, $(C_1-C_6)$-alkylcarbonyl-$(C_1-C_4)$-alkyl;

$(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkoxycarbonyl-$(C_1-C_6)$-haloalkyl, $(C_1-C_6)$-haloalkoxycarbonyl-$(C_1-C_6)$-haloalkyl;

$(C_2-C_6)$-alkenyl, $(C_2-C_6)$-haloalkenyl;

$(C_2-C_6)$-alkynyl, $(C_2-C_6)$-haloalkynyl;

tri-$(C_1-C_6)$-alkylsilyl-$(C_2-C_6)$-alkynyl, di-$(C_1-C_6)$-alkylsilyl-$(C_2-C_6)$-alkynyl, mono-$(C_1-C_6)$-alkylsilyl-$(C_2-C_6)$-alkynyl; phenylsilyl-$(C_2-C_6)$-alkynyl;

$(C_6-C_{14})$-aryl which may be substituted in the aryl moiety in each case by halogen, $(C_1-C_6)$-alkyl and/or $(C_1-C_6)$-haloalkyl;

$(C_6-C_{14})$-aryl-$(C_1-C_6)$-alkyl;

aminocarbonyl-$(C_1-C_6)$-alkyl;

$(C_1-C_6)$-alkoxy-$(C_1-C_6)$-alkyl;

$(C_3-C_8)$-cycloalkyl which may optionally be substituted in the cycloalkyl radical by $(C_1-C_6)$-alkyl and/or halogen; $(C_3-C_8)$-cycloalkyl-$(C_1-C_6)$-alkyl, $(C_3-C_8)$-cycloalkyl-$(C_1-C_6)$-haloalkyl $(C_3-C_8)$-cycloalkenyl, $(C_3-C_8)$-cycloalkenyl-$(C_1-C_6)$-alkyl, $(C_3-C_8)$-cycloalkenyl-$(C_1-C_6)$-haloalkyl, hydroxy-$(C_1-C_6)$-alkyl, cyano-$(C_1-C_6)$-alkyl;

$(C_1-C_6)$-alkylsulfonyl-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-haloalkylthio-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-haloalkyl, $(C_1-C_6)$-alkylthio-$(C_1-C_6)$-haloalkyl, $(C_1-C_6)$-alkylsulfinyl-$(C_1-C_6)$-haloalkyl, $(C_1-C_6)$-haloalkylsulfonyl-$(C_1-C_6)$-haloalkyl, $(C_1-C_6)$-haloalkylthio-$(C_1-C_6)$-haloalkyl, and $(C_1-C_6)$-haloalkylsulfinyl-$(C_1-C_6)$-haloalkyl, and $R^{2a}$ and $R^{2b}$ are each independently selected from the group consisting of hydrogen, halogen, hydroxyl, cyano, nitro, C(O)OH, C(O)NH$_2$;

$(C_1-C_6)$-alkyl, $(C_1-C_6)$-haloalkyl, $(C_1-C_6)$-alkylcarbonyl, $(C_1-C_6)$-haloalkylcarbonyl, $(C_1-C_6)$-alkylcarbonyloxy, $(C_1-C_6)$-haloalkylcarbonyloxy, $(C_1-C_6)$-alkylcarbonyl-$(C_1-C_4)$-alkyl;

$(C_1-C_6)$-alkoxy, $(C_1-C_6)$-haloalkoxy, $(C_1-C_6)$-alkoxycarbonyl, $(C_1-C_6)$-haloalkoxycarbonyl, $(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkoxycarbonyl-$(C_1-C_6)$-haloalkyl, $(C_1-C_6)$-haloalkoxycarbonyl-$(C_1-C_6)$-haloalkyl;

$(C_2-C_6)$-alkenyl, $(C_2-C_6)$-haloalkenyl, $(C_2-C_6)$-alkenylcarbonyl, $(C_2-C_6)$-haloalkenylcarbonyl, $(C_2-C_6)$-alkenyloxy, $(C_2-C_6)$-haloalkenyloxy, $(C_2-C_6)$-alkenyloxycarbonyl, $(C_2-C_6)$-haloalkenyloxycarbonyl;

$(C_2-C_6)$-alkynyl, $(C_2-C_6)$-haloalkynyl, $(C_2-C_6)$-alkynylcarbonyl, $(C_2-C_6)$-haloalkynylcarbonyl, $(C_2-C_6)$-alkynyloxy, $(C_2-C_6)$-haloalkynyloxy, $(C_2-C_6)$-alkynyloxycarbonyl, $(C_2-C_6)$-haloalkynyloxycarbonyl;

tri-$(C_1$-$C_6)$-alkylsilyl-$(C_2$-$C_6)$-alkynyl, di-$(C_1$-$C_6)$-alkylsilyl-$(C_2$-$C_6)$-alkynyl, mono-$(C_1$-$C_6)$-alkylsilyl-$(C_2$-$C_6)$-alkynyl; phenylsilyl-$(C_2$-$C_6)$-alkynyl;

$(C_6$-$C_{14})$-aryl, $(C_6$-$C_{14})$-aryloxy, $(C_6$-$C_{14})$-arylcarbonyl and $(C_6$-$C_{14})$-aryloxycarbonyl, each of which may be substituted in the aryl moiety by halogen, $(C_1$-$C_6)$-alkyl and/or $(C_1$-$C_6)$-haloalkyl;

$(C_6$-$C_{14})$-aryl-$(C_1$-$C_6)$-alkyl, $(C_6$-$C_{14})$-aryl-$(C_1$-$C_6)$-alkoxy, $(C_6$-$C_{14})$-aryl-$(C_1$-$C_6)$-alkylcarbonyl, $(C_6$-$C_{14})$-aryl-$(C_1$-$C_6)$-alkylcarbonyloxy, $(C_6$-$C_{14})$-aryl-$(C_1$-$C_6)$-alkoxycarbonyl, $(C_6$-$C_{14})$-aryl-$(C_1$-$C_6)$-alkoxycarbonyloxy;

aminocarbonyl-$(C_1$-$C_6)$-alkyl, di-$(C_1$-$C_6)$-alkylaminocarbonyl-$(C_1$-$C_6)$-alkyl;

N—(($C_1$-$C_6)$-haloalkanoyl)-aminocarbonyl, mono-(($C_6$-$C_{14})$-aryl)-aminocarbonyl, di-(($C_6$-$C_{14})$-aryl)-aminocarbonyl;

$(C_1$-$C_6)$-alkoxy-$(C_1$-$C_6)$-alkyl, $(C_1$-$C_6)$-alkoxy-$(C_1$-$C_6)$-alkoxy, $(C_1$-$C_6)$-alkoxycarbonyl-$(C_1$-$C_6)$-alkoxy;

$(C_3$-$C_8)$-cycloalkyl which may optionally be substituted in the cycloalkyl radical by $(C_1$-$C_6)$-alkyl and/or halogen; $(C_3$-$C_8)$-cycloalkoxy, $(C_3$-$C_8)$-cycloalkyl-$(C_1$-$C_6)$-alkyl, $(C_3$-$C_8)$-cycloalkyl-$(C_1$-$C_6)$-haloalkyl, $(C_3$-$C_8)$-cycloalkyl-$(C_1$-$C_6)$-alkoxy, $(C_3$-$C_8)$-cycloalkyl-$(C_1$-$C_6)$-haloalkoxy, $(C_3$-$C_5)$-cycloalkylcarbonyl, $(C_3$-$C_8)$-cycloalkoxycarbonyl, $(C_3$-$C_8)$-cycloalkyl-$(C_1$-$C_6)$-alkylcarbonyl, $(C_3$-$C_8)$-cycloalkyl-$(C_1$-$C_6)$-haloalkylcarbonyl, $(C_3$-$C_8)$-cycloalkyl-$(C_1$-$C_6)$-alkoxycarbonyl, $(C_3$-$C_8)$-cycloalkyl-$(C_1$-$C_6)$-haloalkoxycarbonyl, $(C_3$-$C_8)$-cycloalkylcarbonyloxy, $(C_3$-$C_8)$-cycloalkoxycarbonyloxy, $(C_3$-$C_8)$-cycloalkyl-$(C_1$-$C_6)$-alkylcarbonyloxy, $(C_3$-$C_8)$-cycloalkyl-$(C_1$-$C_6)$-haloalkylcarbonyloxy, $(C_3$-$C_8)$-cycloalkyl-$(C_1$-$C_6)$-alkoxycarbonyloxy, $(C_3$-$C_8)$-cycloalkyl-$(C_1$-$C_6)$-haloalkoxycarbonyloxy;

$(C_3$-$C_8)$-cycloalkenyl, $(C_3$-$C_8)$-cycloalkenyloxy, $(C_3$-$C_8)$-cycloalkenyl-$(C_1$-$C_6)$-alkyl, $(C_3$-$C_8)$-cycloalkenyl-$(C_1$-$C_6)$-haloalkyl, $(C_3$-$C_8)$-cycloalkenyl-$(C_1$-$C_6)$-alkoxy, $(C_3$-$C_8)$-cycloalkenyl-$(C_1$-$C_6)$-haloalkoxy, $(C_3$-$C_8)$-cycloalkenylcarbonyl, $(C_3$-$C_8)$-cycloalkenyloxycarbonyl, $(C_3$-$C_8)$-cycloalkenyl-$(C_1$-$C_6)$-alkylcarbonyl, $(C_3$-$C_8)$-cycloalkenyl-$(C_1$-$C_6)$-haloalkylcarbonyl, $(C_3$-$C_8)$-cycloalkenyl-$(C_1$-$C_6)$-alkoxycarbonyl, $(C_3$-$C_8)$-cycloalkenyl-$(C_1$-$C_6)$-haloalkoxycarbonyl, $(C_3$-$C_8)$-cycloalkenylcarbonyloxy, $(C_3$-$C_8)$-cycloalkenyloxycarbonyloxy, $(C_3$-$C_8)$-cycloalkenyl-$(C_1$-$C_6)$-alkylcarbonyloxy, $(C_3$-$C_8)$-cycloalkenyl-$(C_1$-$C_6)$-haloalkylcarbonyloxy, $(C_3$-$C_8)$-cycloalkenyl-$(C_1$-$C_6)$-alkoxycarbonyloxy, $(C_3$-$C_8)$-cycloalkenyl-$(C_1$-$C_6)$-haloalkoxycarbonyloxy;

hydroxy-$(C_1$-$C_6)$-alkyl, hydroxy-$(C_1$-$C_6)$-alkoxy, cyano-$(C_1$-$C_6)$-alkoxy, cyano-$(C_1$-$C_6)$-alkyl;

$(C_1$-$C_6)$-alkylsulfonyl, $(C_1$-$C_6)$-alkylthio, $(C_1$-$C_6)$-alkylsulfinyl, $(C_1$-$C_6)$-haloalkylsulfonyl, $(C_1$-$C_6)$-haloalkylthio, $(C_1$-$C_6)$-haloalkylsulfinyl, $(C_1$-$C_6)$-alkylsulfonyl-$(C_1$-$C_6)$-alkyl, $(C_1$-$C_6)$-alkylthio-$(C_1$-$C_6)$-alkyl, $(C_1$-$C_6)$-alkylsulfinyl-$(C_1$-$C_6)$-alkyl, $(C_1$-$C_6)$-haloalkylsulfonyl-$(C_1$-$C_6)$-alkyl, $(C_1$-$C_6)$-haloalkylthio-$(C_1$-$C_6)$-alkyl, $(C_1$-$C_6)$-haloalkylsulfinyl-$(C_1$-$C_6)$-alkyl, $(C_1$-$C_6)$-alkylsulfonyl-$(C_1$-$C_6)$-haloalkyl, $(C_1$-$C_6)$-alkylthio-$(C_1$-$C_6)$-haloalkyl, $(C_1$-$C_6)$-alkylsulfinyl-$(C_1$-$C_6)$-haloalkyl, $(C_1$-$C_6)$-haloalkylsulfonyl-$(C_1$-$C_6)$-haloalkyl, $(C_1$-$C_6)$-haloalkylthio-$(C_1$-$C_6)$-haloalkyl, $(C_1$-$C_6)$-haloalkylsulfinyl-$(C_1$-$C_6)$-haloalkyl, $(C_1$-$C_6)$-alkylsulfonyloxy, $(C_1$-$C_6)$-haloalkylsulfonyloxy, $(C_1$-$C_6)$-alkylthiocarbonyl, $(C_1$-$C_6)$-haloalkylthiocarbonyl, $(C_1$-$C_6)$-alkylthiocarbonyloxy, $(C_1$-$C_6)$-haloalkylthiocarbonyloxy, $(C_1$-$C_6)$-alkylthio-$(C_1$-$C_6)$-alkyl, $(C_1$-$C_6)$-alkylthio-$(C_1$-$C_6)$-alkoxy, $(C_1$-$C_6)$-alkylthio-$(C_1$-$C_6)$-alkylcarbonyl, $(C_1$-$C_6)$-alkylthio-$(C_1$-$C_6)$-alkylcarbonyloxy; $(C_4$-$C_{14})$-arylsulfonyl, $(C_6$-$C_{14})$-arylthio, $(C_6$-$C_{14})$-arylsulfinyl, $(C_3$-$C_8)$-cycloalkylthio, $(C_3$-$C_8)$-alkenylthio, $(C_3$-$C_8)$-cycloalkenylthio, and $(C_3$-$C_6)$-alkynylthio; and $R^1$ and $R^{2a}$ may be joined to one another via a bond so as to form, together with carbon 4 (or carbon 6) and 5 of the pyrimidine and the carbonyl group in the 5 position of the pyrimidine, a 5- to 7-membered partly hydrogenated carbo- or heterocycle which may also be substituted;

$R^3$ is selected from the group consisting of hydrogen, $(C_1$-$C_6)$-alkyl, $(C_1$-$C_6)$-alkoxy, $(C_1$-$C_6)$-alkoxy-$(C_1$-$C_6)$-alkyl, $(C_1$-$C_6)$-alkoxycarbonyl and aminocarbonyl;

$R^4$ and $R^5$ are each independently selected from the group consisting of hydrogen, $(C_1$-$C_6)$-alkyl, $(C_1$-$C_6)$-alkylphenyl, $(C_1$-$C_6)$-haloalkyl, hydroxyl, $(C_1$-$C_6)$-alkoxy and $(C_1$-$C_6)$-haloalkoxy; or the $R^4$ and $R^5$ radicals together with the carbon atom to which they are bonded form a three- to seven-membered ring; and $R^6$ and $R^7$ are each independently selected from the group consisting of hydrogen, $(C_1$-$C_6)$-alkyl, $(C_1$-$C_6)$-haloalkyl, $(C_1$-$C_6)$-alkoxy, $(C_1$-$C_6)$-haloalkoxy, $(C_6$-$C_{14})$-aryl, $(C_6$-$C_{14})$-aryloxy, $(C_6$-$C_{14})$-arylcarbonyl and $(C_6$-$C_{14})$-aryloxycarbonyl; or the $R^6$ and $R^7$ radicals together form a $(C_1$-$C_7)$-alkylene group which may contain one or more oxygen and/or sulfur atoms, where the $(C_1$-$C_7)$-alkylene group may be mono- or polysubstituted by halogen and the respective halogen substituents may be the same or different, and n is 0, 1 or 2 and $R^8$ is selected from the group consisting of hydrogen, halogen, cyano, C(O)OH, C(O)NH$_2$, $(C_1$-$C_6)$-alkyl, $(C_1$-$C_6)$-alkylcarbonyl, $(C_1$-$C_6)$-alkyloxycarbonyl, $(C_1$-$C_6)$-alkylaminocarbonyl, $(C_1$-$C_6)$-dialkylaminocarbonyl, $(C_1$-$C_6)$-haloalkyl, $(C_1$-$C_6)$-alkoxy, $(C_1$-$C_6)$-haloalkoxy, $(C_2$-$C_6)$-alkenyl, $(C_2$-$C_6)$-alkynyl, $(C_2$-$C_6)$-haloalkynyl, $(C_2$-$C_6)$-alkynylcarbonyl, $(C_2$-$C_6)$-haloalkynylcarbonyl, $(C_2$-$C_6)$-alkynyloxy, $(C_2$-$C_6)$-haloalkynyloxy, $(C_2$-$C_6)$-alkynyloxycarbonyl, $(C_6$-$C_{14})$-aryl, $(C_2$-$C_6)$-haloalkynyloxycarbonyl and nitro;

$R^9$ and $R^{11}$ are each independently selected from the group consisting of hydrogen, halogen, cyano, C(O)OH, C(O)NH$_2$, $(C_1$-$C_6)$-alkyl, $(C_1$-$C_6)$-alkylcarbonyl, $(C_1$-$C_6)$-alkyloxycarbonyl, $(C_1$-$C_6)$-alkylaminocarbonyl, $(C_1$-$C_6)$-dialkylaminocarbonyl, $(C_1$-$C_6)$-haloalkyl, $(C_1$-$C_6)$-alkoxy, $(C_1$-$C_6)$-haloalkoxy, $(C_2$-$C_6)$-alkenyl, $(C_2$-$C_6)$-alkynyl, $(C_2$-$C_6)$-haloalkynyl, $(C_2$-$C_6)$-alkynylcarbonyl, $(C_2$-$C_6)$-haloalkynylcarbonyl, $(C_2$-$C_6)$-alkynyloxy, $(C_2$-$C_6)$-haloalkynyloxy, $(C_2$-$C_6)$-alkynyloxycarbonyl, $(C_2$-$C_6)$-haloalkynyloxycarbonyl and nitro;

$R^{10}$ is selected from the group consisting of hydrogen, halogen, cyano, C(O)OH, C(O)NH$_2$, $(C_1$-$C_6)$-alkyl, $(C_1$-$C_6)$-alkylcarbonyl, $(C_1$-$C_6)$-alkyloxycarbonyl, $(C_1$-$C_6)$-alkylaminocarbonyl, $(C_1$-$C_6)$-dialkylaminocarbonyl, $(C_1$-$C_6)$-haloalkyl, $(C_1$-$C_6)$-alkoxy, $(C_1$-$C_6)$-haloalkoxy, $(C_2$-$C_6)$-alkenyl, $(C_2$-$C_6)$-alkynyl, $(C_1$-$C_6)$-alkyl-$(C_2$-$C_6)$-alkynyl, hydroxy-$(C_1$-$C_6)$-alkyl-$(C_2$-$C_6)$-alkynyl, $(C_1$-$C_6)$-alkoxy-$(C_2$-$C_6)$-alkynyl and aryl-$(C_2$-$C_6)$-alkynyl, $(C_2$-$C_6)$-haloalkynyl, $(C_2$-$C_6)$- alkynylcarbonyl, $(C_2-C_6)$-haloalkynylcarbonyl, $(C_2-C_6)$-alkynyloxy, $(C_2-C_6)$-haloalkynyloxy, $(C_2-C_6)$-alkynyloxycarbonyl, $(C_2-C_6)$-haloalkynyloxycarbonyl and nitro;

X is a bond, $CH_2$, O, S, carbonyl, NH, $CR^{12}R^{13}$ and $NR^{14}$ or $CH_2O$, $CH_2S$, where the carbon atom in the two latter groups is bonded to the aromatic moiety;

wherein if n is 0, X is not a bond;

and $R^{12}$ and $R^{13}$ are each independently selected from the group consisting of hydrogen, $(C_1-C_6)$-alkyl and $(C_1-C_6)$-haloalkyl; and $R^{14}$ is selected from the group consisting of hydrogen, $(C_1-C_6)$-alkyl, and $(C_1-C_6)$-haloalkyl.

2. A compound of formula (I) and/or salt as claimed in claim 1, wherein 1-[2-[(7-methoxy-2,2-dimethylchroman-4-yl)amino]-4-methylpyrimidin-5-yl]ethanone having empirical formula $C_{19}H_{23}N_3O_3$ is excluded.

3. A compound of formula (I) and/or salt as claimed in claim 1, wherein $R^1$ is selected from the group consisting of $(C_1-C_6)$-alkyl, $(C_1-C_6)$-haloalkyl, $(C_1-C_6)$-alkoxy-$(C_1-C_6)$-alkyl, $(C_3-C_8)$-cycloalkyl which may optionally be substituted in the cycloalkyl radical by $(C_1-C_6)$-alkyl and/or halogen, $(C_3-C_8)$-cycloalkyl-$(C_1-C_6)$-alkyl and $(C_3-C_8)$-cycloalkyl-$(C_1-C_6)$-haloalkyl.

4. A compound of formula (I) and/or salt as claimed in claim 1, wherein the $R^{2a}$ and $R^{2b}$ radicals are each independently selected from the group consisting of hydrogen, $(C_1-C_6)$-alkyl, $(C_1-C_6)$-haloalkyl, $(C_1-C_6)$-alkoxy, $(C_1-C_6)$-alkoxy-$(C_1-C_6)$-alkyl, $(C_3-C_8)$-cycloalkyl which may optionally be substituted in the cycloalkyl radical by $(C_1-C_6)$-alkyl and/or halogen, $(C_3-C_8)$-cycloalkyl-$(C_1-C_6)$-alkyl and $(C_3-C_8)$-cycloalkyl-$(C_1-C_6)$-haloalkyl.

5. A compound of formula (I) and/or salt as claimed in claim 1, wherein the radical $R^3$ is selected from the group consisting of hydrogen, $(C_1-C_6)$-alkyl, $(C_1-C_6)$-alkoxy, $(C_1-C_6)$-alkoxy-$(C_1-C_6)$-alkyl, $(C_1-C_6)$-alkoxycarbonyl and aminocarbonyl.

6. A compound of formula (I) and/or salt as claimed in claim 1, wherein the $R^4$ and $R^5$ radicals are each independently selected from the group consisting of hydrogen, hydroxyl, $(C_1-C_6)$-alkyl, $(C_1-C_6)$-alkylphenyl and $(C_1-C_6)$-alkoxy.

7. A compound of formula (I) and/or salt as claimed in claim 1, wherein the $R^6$ and $R^7$ radicals are each independently selected from the group consisting of hydrogen, $(C_1-C_6)$-alkyl and $(C_6-C_{14})$-aryl.

8. A compound of formula (I) and/or salt as claimed in claim 1, wherein the $R^8$ radical is selected from the group consisting of hydrogen, halogen, $(C_1-C_6)$-alkyl, $(C_1-C_6)$-alkoxy and $(C_6-C_{14})$-aryl.

9. A compound of formula (I) and/or salt as claimed in claim 1, wherein the $R^9$ radical is selected from the group consisting of hydrogen, halogen, $(C_1-C_6)$-alkyl and $(C_1-C_6)$-alkoxy.

10. A compound of formula (I) and/or salt as claimed in claim 1, wherein the $R^{10}$ radical is selected from the group consisting of hydrogen, halogen, cyano, C(O)OH, C(O)$NH_2$, $(C_1-C_6)$-alkyl, $(C_1-C_6)$-haloalkyl, $(C_1-C_6)$-alkoxy, $(C_2-C_6)$-alkenyl, $(C_2-C_6)$-alkynyl, $(C_1-C_6)$-alkyl-$(C_2-C_6)$-alkynyl, hydroxy-$(C_1-C_6)$-alkyl-$(C_2-C_6)$-alkynyl, $(C_1-C_6)$-alkoxy-$(C_2-C_6)$-alkynyl and aryl-$(C_2-C_6)$-alkynyl.

11. A compound of formula (I) and/or salt as claimed in claim 1, wherein the $R^{11}$ radical is selected from the group consisting of hydrogen and $(C_1-C_6)$-alkyl.

12. A compound of formula (I) and/or salt as claimed in claim 1, wherein the X radical is a chemical bond or the X radical is selected from the group consisting of O, S, carbonyl, $CH_2$, NH, $CH(C_1-C_6)$alkyl, and $(C_1-C_6)$alkylamino.

13. A compound of formula (I) and/or salt as claimed in claim 1, wherein the $R^1$ and $R^{2a}$ radicals together with carbons 4 and 5 of the pyrimidine and the carbonyl group in the 5 position of the pyrimidine form a 5- to 7-membered partly hydrogenated carbo- or heterocycle in which the heteroatoms are selected from the group consisting of oxygen and sulfur, where a sulfoxide group or a sulfonyl group may be present in place of the sulfur, and the carbo- or heterocycle is unsubstituted or at least monosubstituted and where the substituents are selected from the group consisting of $(C_1-C_6)$-alkyl, $(C_1-C_6)$-haloalkyl, aryl, phenyl $(C_6H_5)$ which is unsubstituted or at least monosubstituted by fluorine, chlorine, bromine or iodine, and $(C_1-C_6)$-cycloalkyl.

14. A compound of formula (I)

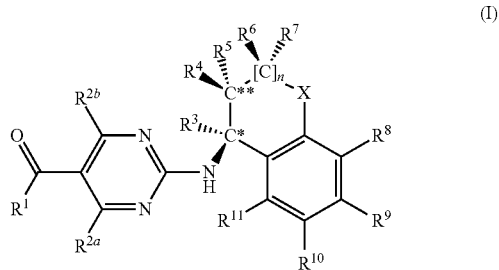

and/or salt as claimed in claim 1, wherein the chiral carbon atom indicated by (*) has (R) configuration, wherein the chiral carbon atom indicated by () has (R) or (S) configuration, and wherein the chiral carbon atom indicated by (*) has (R) or (S) configuration.

15. A compound of formula (I) and/or salt as claimed in claim 14, wherein the chiral carbon atom indicated by (**) has (S) configuration.

16. A herbicidal composition or plant growth-regulating composition, comprising one or more compounds of formula (I) and/or one or more salts thereof as claimed in claim 1.

17. A method of controlling harmful plants or of regulating the growth of plants, comprising applying an effective amount of one or more compounds of formula (I) or one or more salts thereof as claimed in claim 1 to one or more plants, plant parts, plant seeds or an area under cultivation.

18. A product comprising one or more compounds of formula (I) or one or more salts thereof as claimed in claim 1 as herbicides or as plant growth regulators.

19. The product as claimed in claim 18, wherein the one or more compounds of formula (I) or one or more salts thereof are adapted in said product to be used to control harmful plants or to regulate the growth of plants in crops of useful plants or ornamental plants.

20. The product as claimed in claim 19, wherein the crop plants are transgenic crop plants.

21. A process for preparing one or more compounds of formula (I) and/or one or more agrochemically acceptable salts thereof and/or one or more agrochemically acceptable quaternized nitrogen derivatives thereof

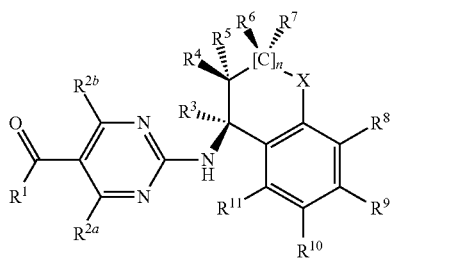

(I)

in which the $R^1$ to $R^{11}$ and X radicals are
$R^1$ is selected from the group consisting of
- $(C_1-C_6)$-alkyl, $(C_1-C_6)$-haloalkyl, $(C_1-C_6)$-alkylcarbonyl-$(C_1-C_4)$-alkyl;
- $(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkoxycarbonyl-$(C_1-C_6)$-haloalkyl, $(C_1-C_6)$-haloalkoxycarbonyl-$(C_1-C_6)$-haloalkyl;
- $(C_2-C_6)$-alkenyl, $(C_2-C_6)$-haloalkenyl;
- $(C_2-C_6)$-alkynyl, $(C_2-C_6)$-haloalkynyl;
- tri-$(C_1-C_6)$-alkylsilyl-$(C_2-C_6)$-alkynyl, di-$(C_1-C_6)$-alkylsilyl-$(C_2-C_6)$-alkynyl, mono-$(C_1-C_6)$-alkylsilyl-$(C_2-C_6)$-alkynyl; phenylsilyl-$(C_2-C_6)$-alkynyl;
- $(C_6-C_{14})$-aryl which may be substituted in the aryl moiety in each case by halogen, $(C_1-C_6)$-alkyl and/or $(C_1-C_6)$-haloalkyl;
- $(C_6-C_{14})$-aryl-$(C_1-C_6)$-alkyl;
- aminocarbonyl-$(C_1-C_6)$-alkyl;
- $(C_1-C_6)$-alkoxy-$(C_1-C_6)$-alkyl;
- $(C_3-C_8)$-cycloalkyl which may optionally be substituted in the cycloalkyl radical by $(C_1-C_6)$-alkyl and/or halogen; $(C_3-C_8)$-cycloalkyl-$(C_1-C_6)$-alkyl, $(C_3-C_8)$-cycloalkyl-$(C_1-C_6)$-haloalkyl
- $(C_3-C_8)$-cycloalkenyl, $(C_3-C_8)$-cycloalkenyl-$(C_1-C_6)$-alkyl, $(C_3-C_8)$-cycloalkenyl-$(C_1-C_6)$-haloalkyl, hydroxy-$(C_1-C_6)$-alkyl, cyano-$(C_1-C_6)$-alkyl;
- $(C_1-C_6)$-alkylsulfonyl-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-haloalkylthio-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-haloalkyl, $(C_1-C_6)$-alkylthio-$(C_1-C_6)$-haloalkyl, $(C_1-C_6)$-alkylsulfinyl-$(C_1-C_6)$-haloalkyl, $(C_1-C_6)$-haloalkylsulfonyl-$(C_1-C_6)$-haloalkyl, $(C_1-C_6)$-haloalkylthio-$(C_1-C_6)$-haloalkyl, $(C_1-C_6)$-haloalkylsulfinyl-$(C_1-C_6)$-haloalkyl, and $R^{2a}$ and $R^{2b}$ are each independently selected from the group consisting of
- hydrogen, halogen, hydroxyl, cyano, nitro, C(O)OH, C(O)NH$_2$;
- $(C_1-C_6)$-alkyl, $(C_1-C_6)$-haloalkyl, $(C_1-C_6)$-alkylcarbonyl, $(C_1-C_6)$-haloalkylcarbonyl, $(C_1-C_6)$-alkylcarbonyloxy, $(C_1-C_6)$-haloalkylcarbonyloxy, $(C_1-C_6)$-alkylcarbonyl-$(C_1-C_4)$-alkyl;
- $(C_1-C_6)$-alkoxy, $(C_1-C_6)$-haloalkoxy, $(C_1-C_6)$-alkoxycarbonyl, $(C_1-C_6)$-haloalkoxycarbonyl, $(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkoxycarbonyl-$(C_1-C_6)$-haloalkyl, $(C_1-C_6)$-haloalkoxycarbonyl-$(C_1-C_6)$-haloalkyl;
- $(C_2-C_6)$-alkenyl, $(C_2-C_6)$-haloalkenyl, $(C_2-C_6)$-alkenylcarbonyl, $(C_2-C_6)$-haloalkenylcarbonyl, $(C_2-C_6)$-alkenyloxy, $(C_2-C_6)$-haloalkenyloxy, $(C_2-C_6)$-alkenyloxycarbonyl, $(C_2-C_6)$-haloalkenyloxycarbonyl;
- $(C_2-C_6)$-alkynyl, $(C_2-C_6)$-haloalkynyl, $(C_2-C_6)$-alkynylcarbonyl, $(C_2-C_6)$-haloalkynylcarbonyl, $(C_2-C_6)$-alkynyloxy, $(C_2-C_6)$-haloalkynyloxy, $(C_2-C_6)$-alkynyloxycarbonyl, $(C_2-C_6)$-haloalkynyloxycarbonyl;
- tri-$(C_1-C_6)$-alkylsilyl-$(C_2-C_6)$-alkynyl, di-$(C_1-C_6)$-alkylsilyl-$(C_2-C_6)$-alkynyl, mono-$(C_1-C_6)$-alkylsilyl-$(C_2-C_6)$-alkynyl; phenylsilyl-$(C_2-C_6)$-alkynyl;
- $(C_6-C_{14})$-aryl, $(C_6-C_{14})$-aryloxy, $(C_6-C_{14})$-arylcarbonyl and $(C_6-C_{14})$-aryloxycarbonyl, each of which may be substituted in the aryl moiety by halogen, $(C_1-C_6)$-alkyl and/or $(C_1-C_6)$-haloalkyl;
- $(C_6-C_{14})$-aryl-$(C_1-C_6)$-alkyl, $(C_6-C_{14})$-aryl-$(C_1-C_6)$-alkoxy, $(C_6-C_{14})$-aryl-$(C_1-C_6)$-alkylcarbonyl, $(C_6-C_{14})$-aryl-$(C_1-C_6)$-alkylcarbonyloxy, $(C_6-C_{14})$-aryl-$(C_1-C_6)$-alkoxycarbonyl, $(C_6-C_{14})$-aryl-$(C_1-C_6)$-alkoxycarbonyloxy;
- aminocarbonyl-$(C_1-C_6)$-alkyl, di-$(C_1-C_6)$-alkylaminocarbonyl-$(C_1-C_6)$-alkyl;
- N—(($(C_1-C_6)$-haloalkanoyl)-aminocarbonyl, mono-(($(C_6-C_{14})$-aryl)-aminocarbonyl, di-(($(C_6-C_{14})$-aryl)-aminocarbonyl;
- $(C_1-C_6)$-alkoxy-$(C_1-C_6)$-alkyl, $(C_1-C_6)$-alkoxy-$(C_1-C_6)$-alkoxy, $(C_1-C_6)$-alkoxycarbonyl-$(C_1-C_6)$-alkoxy;
- $(C_3-C_8)$-cycloalkyl which may optionally be substituted in the cycloalkyl radical by $(C_1-C_6)$-alkyl and/or halogen; $(C_3-C_8)$-cycloalkoxy, $(C_3-C_8)$-cycloalkyl-$(C_1-C_6)$-alkyl, $(C_3-C_8)$-cycloalkyl-$(C_1-C_6)$-haloalkyl, $(C_3-C_8)$-cycloalkyl-$(C_1-C_6)$-alkoxy, $(C_3-C_8)$-cycloalkyl-$(C_1-C_6)$-haloalkoxy, $(C_3-C_8)$-cycloalkylcarbonyl, $(C_3-C_8)$-cycloalkoxycarbonyl, $(C_3-C_8)$-cycloalkyl-$(C_1-C_6)$-alkylcarbonyl, $(C_3-C_8)$-cycloalkyl-$(C_1-C_6)$-haloalkylcarbonyl, $(C_3-C_8)$-cycloalkyl-$(C_1-C_6)$-alkoxycarbonyl, $(C_3-C_8)$-cycloalkyl-$(C_1-C_6)$-haloalkoxycarbonyl, $(C_3-C_8)$-cycloalkylcarbonyloxy, $(C_3-C_8)$-cycloalkoxycarbonyloxy, $(C_3-C_8)$-cycloalkyl-$(C_1-C_6)$-alkylcarbonyloxy, $(C_3-C_8)$-cycloalkyl-$(C_1-C_6)$-haloalkylcarbonyloxy, $(C_3-C_8)$-cycloalkyl-$(C_1-C_6)$-alkoxycarbonyloxy, $(C_3-C_8)$-cycloalkyl-$(C_1-C_6)$-haloalkoxycarbonyloxy;
- $(C_3-C_8)$-cycloalkenyl, $(C_3-C_8)$-cycloalkenyloxy, $(C_3-C_8)$-cycloalkenyl-$(C_1-C_6)$-alkyl, $(C_3-C_8)$-cycloalkenyl-$(C_1-C_6)$-haloalkyl, $(C_3-C_8)$-cycloalkenyl-$(C_1-C_6)$-alkoxy, $(C_3-C_8)$-cycloalkenyl-$(C_1-C_6)$-haloalkoxy, $(C_3-C_8)$-cycloalkenylcarbonyl, $(C_3-C_8)$-cycloalkenyloxycarbonyl, $(C_3-C_8)$-cycloalkenyl-$(C_1-C_6)$-alkylcarbonyl, $(C_3-C_8)$-cycloalkenyl-$(C_1-C_6)$-haloalkylcarbonyl, $(C_3-C_8)$-cycloalkenyl-$(C_1-C_6)$-alkoxycarbonyl, $(C_3-C_8)$-cycloalkenyl-$(C_1-C_6)$-haloalkoxycarbonyl, $(C_3-C_8)$-cycloalkenylcarbonyloxy, $(C_3-C_8)$-cycloalkenyloxycarbonyloxy, $(C_3-C_8)$-cycloalkenyl-$(C_1-C_6)$-alkylcarbonyloxy, $(C_3-C_8)$-cycloalkenyl-$(C_1-C_6)$-haloalkylcarbonyloxy, $(C_3-C_8)$-cycloalkenyl-$(C_1-C_6)$-alkoxycarbonyloxy, $(C_3-C_8)$-cycloalkenyl-$(C_1-C_6)$-haloalkoxycarbonyloxy;
- hydroxy-$(C_1-C_6)$-alkyl, hydroxy-$(C_1-C_6)$-alkoxy, cyano-$(C_1-C_6)$-alkoxy, cyano-$(C_1-C_6)$-alkyl;
- $(C_1-C_6)$-alkylsulfonyl, $(C_1-C_6)$-alkylthio, $(C_1-C_6)$-alkylsulfinyl, $(C_1-C_6)$-haloalkylsulfonyl, $(C_1-C_6)$-haloalkylthio, $(C_1-C_6)$-haloalkylsulfinyl, $(C_1-C_6)$-alkylsulfonyl-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-$ $C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl, ($C_1$-$C_6$)-alkylsulfonyloxy, ($C_1$-$C_6$)-haloalkylsulfonyloxy, ($C_1$-$C_6$)-alkylthiocarbonyl, ($C_1$-$C_6$)-haloalkylthiocarbonyl, ($C_1$-$C_6$)-alkylthiocarbonyloxy, ($C_1$-$C_6$)-haloalkylthiocarbonyloxy, ($C_1$-$C_6$)-alkylthio-($C_1$-$C_6$)-alkyl, ($C_1$-$C_6$)-alkylthio-($C_1$-$C_6$)-alkoxy, ($C_1$-$C_6$)-alkylthio-($C_1$-$C_6$)-alkylcarbonyl, ($C_1$-$C_6$)-alkylthio-($C_1$-$C_6$)-alkylcarbonyloxy; ($C_4$-$C_{14}$)-arylsulfonyl, ($C_6$-$C_{14}$)-arylthio, ($C_6$-$C_{14}$)-arylsulfinyl, ($C_3$-$C_8$)-cycloalkylthio, ($C_3$-$C_8$)-alkenylthio, ($C_3$-$C_8$)-cycloalkenylthio, and ($C_3$-$C_6$)-alkynylthio; and $R^1$ and $R^{2a}$ may be joined to one another via a bond so as to form, together with carbon 4 (or carbon 6) and 5 of the pyrimidine and the carbonyl group in the 5 position of the pyrimidine, a 5- to 7-membered partly hydrogenated carbo- or heterocycle which may also be substituted;

$R^3$ is selected from the group consisting of hydrogen, ($C_1$-$C_6$)-alkyl, ($C_1$-$C_6$)-alkoxy, ($C_1$-$C_6$)-alkoxy-($C_1$-$C_6$)-alkyl, ($C_1$-$C_6$)-alkoxycarbonyl and aminocarbonyl;

$R^4$ and $R^5$ are each independently selected from the group consisting of hydrogen, ($C_1$-$C_6$)-alkyl, ($C_1$-$C_6$)-haloalkyl, hydroxyl, ($C_1$-$C_6$)-alkoxy and ($C_1$-$C_6$)-haloalkoxy; or the $R^4$ and $R^5$ radicals together with the carbon atom to which they are bonded form a three- to seven-membered ring; and $R^6$ and $R^7$ are each independently selected from the group consisting of hydrogen, ($C_1$-$C_6$)-alkyl, ($C_1$-$C_6$)-haloalkyl, ($C_1$-$C_6$)-alkoxy, ($C_1$-$C_6$)-haloalkoxy, ($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl; or the $R^6$ and $R^7$ radicals together form a ($C_1$-$C_7$)-alkylene group which may contain one or more oxygen and/or sulfur atoms, where the ($C_1$-$C_7$)-alkylene group may be mono- or polysubstituted by halogen and the respective halogen substituents may be the same or different, and n is 0, 1 or 2 and $R^8$, $R^9$, $R^{10}$ and $R^{11}$ are each independently selected from the group consisting of hydrogen, halogen, cyano, C(O)OH, C(O)NH$_2$, ($C_1$-$C_6$)-alkyl, ($C_1$-$C_6$)-alkylcarbonyl, ($C_1$-$C_6$)-alkyloxycarbonyl, ($C_1$-$C_6$)-alkylaminocarbonyl, ($C_1$-$C_6$)-dialkylaminocarbonyl, ($C_1$-$C_6$)-haloalkyl, ($C_1$-$C_6$)-alkoxy, ($C_1$-$C_6$)-haloalkoxy, ($C_2$-$C_6$)-alkenyl, ($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl and nitro;

X is a bond, CH$_2$, O, S, carbonyl, NH, CR$^{12}$R$^{13}$ and NR$^{14}$ or CH$_2$O, CH$_2$S, where the carbon atom in the two latter groups is bonded to the aromatic moiety;

wherein if n is 0, X is not a bond; and $R^{12}$ and $R^{13}$ are each independently selected from the group consisting of hydrogen, ($C_1$-$C_6$)-alkyl and ($C_1$-$C_6$)-haloalkyl; and $R^{14}$ is selected from the group consisting of hydrogen, ($C_1$-$C_6$)-alkyl, ($C_1$-$C_6$)-haloalkyl;

said process comprising reacting a compound of formula (II)

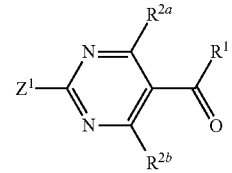

wherein $Z^1$ is an exchangeable radical or a leaving group and $R^1$, $R^{2a}$, and $R^{2b}$ are as defined above, with an amine of formula (III) or with an acid addition salt of an amine of formula (III)

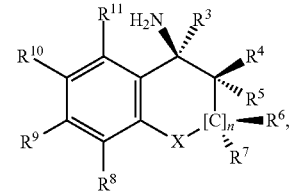

in which $R^3$, $R^4$, $R^5$, $R^6$, $R^7$, $R^8$, $R^9$, $R^{10}$, $R^{11}$, X, and n are as defined above.

22. The process as claimed in claim 21, wherein the exchangeable radical or the leaving group $Z^1$ is fluorine, chlorine, bromine, iodine, a ($C_1$-$C_4$)-alkylsulfanyl or a ($C_1$-$C_4$)-alkylsulfinyl or a ($C_1$-$C_4$)-alkylsulfonyl, an unsubstituted or substituted phenyl-($C_1$-$C_4$)-alkylsulfonyl or a ($C_1$-$C_4$)-alkylphenylsulfonyl.

23. A process for preparing compounds of formula (I) and/or agrochemically acceptable salts thereof and/or agrochemically acceptable quaternized nitrogen derivatives thereof

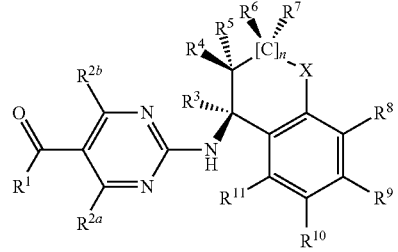

in which the $R^1$ to $R^{11}$ and X radicals are $R^1$ is selected from the group consisting of
($C_1$-$C_6$)-alkyl, ($C_1$-$C_6$)-haloalkyl, ($C_1$-$C_6$)-alkylcarbonyl-($C_1$-$C_4$)-alkyl;
($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;
($C_2$-$C_6$)-alkenyl, ($C_2$-$C_6$)-haloalkenyl;
($C_2$-$C_6$)-alkynyl, ($C_2$-$C_6$)-haloalkynyl;
tri-($C_1$-$C_6$)-alkylsilyl-($C_2$-$C_6$)-alkynyl, di-($C_1$-$C_6$)-alkylsilyl-($C_2$-$C_6$)-alkynyl, mono-($C_1$-$C_6$)-alkylsilyl-($C_2$-$C_6$)-alkynyl; phenylsilyl-($C_2$-$C_6$)-alkynyl;

($C_6$-$C_{14}$)-aryl which may be substituted in the aryl moiety in each case by halogen, ($C_1$-$C_6$)-alkyl and/or ($C_1$-$C_6$)-haloalkyl;
($C_6$-$C_{14}$)-aryl-($C_1$-$C_6$)-alkyl;
aminocarbonyl-($C_1$-$C_6$)-alkyl;
($C_1$-$C_6$)-alkoxy-($C_1$-$C_6$)-alkyl;
($C_3$-$C_8$)-cycloalkyl which may optionally be substituted in the cycloalkyl radical by ($C_1$-$C_6$)-alkyl and/or halogen; ($C_3$-$C_8$)-cycloalkyl-($C_1$-$C_6$)-alkyl, ($C_3$-$C_8$)-cycloalkyl-($C_1$-$C_6$)-haloalkyl
($C_3$-$C_8$)-cycloalkenyl, ($C_3$-$C_8$)-cycloalkenyl-($C_1$-$C_6$)-alkyl, ($C_3$-$C_8$)-cycloalkenyl-($C_1$-$C_6$)-haloalkyl, hydroxy-($C_1$-$C_6$)-alkyl, cyano-($C_1$-$C_6$)-alkyl;
($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl, and $R^{2a}$ and $R^{2b}$ are each independently selected from the group consisting of
hydrogen, halogen, hydroxyl, cyano, nitro, C(O)OH, C(O)$NH_2$;
($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-haloalkylcarbonyloxy, ($C_1$-$C_6$)-alkylcarbonyl-($C_1$-$C_4$)-alkyl;
($C_1$-$C_6$)-alkoxy, ($C_1$-$C_6$)-haloalkoxy, ($C_1$-$C_6$)-alkoxycarbonyl, ($C_1$-$C_6$)-haloalkoxycarbonyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl;
($C_2$-$C_6$)-alkenyl, ($C_2$-$C_6$)-haloalkenyl, ($C_2$-$C_6$)-alkenylcarbonyl, ($C_2$-$C_6$)-haloalkenylcarbonyl, ($C_2$-$C_6$)-alkenyloxy, ($C_2$-$C_6$)-haloalkenyloxy, ($C_2$-$C_6$)-alkenyloxycarbonyl, ($C_2$-$C_6$)-haloalkenyloxycarbonyl;
($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl;
tri-($C_1$-$C_6$)-alkylsilyl-($C_2$-$C_6$)-alkynyl, di-($C_1$-$C_6$)-alkylsilyl-($C_2$-$C_6$)-alkynyl, mono-($C_1$-$C_6$)-alkylsilyl-($C_2$-$C_6$)-alkynyl; phenylsilyl-($C_2$-$C_6$)-alkynyl;
($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl, each of which may be substituted in the aryl moiety by halogen, ($C_1$-$C_6$)-alkyl and/or ($C_1$-$C_6$)-haloalkyl;
($C_6$-$C_{14}$)-aryl-($C_1$-$C_6$)-alkyl, ($C_6$-$C_{14}$)-aryl-($C_1$-$C_6$)-alkoxy, ($C_6$-$C_{14}$)-aryl-($C_1$-$C_6$)-alkylcarbonyl, ($C_6$-$C_{14}$)-aryl-($C_1$-$C_6$)-alkylcarbonyloxy, ($C_6$-$C_{14}$)-aryl-($C_1$-$C_6$)-alkoxycarbonyl, ($C_6$-$C_{14}$)-aryl-($C_1$-$C_6$)-alkoxycarbonyloxy;
aminocarbonyl-($C_1$-$C_6$)-alkyl, di-($C_1$-$C_6$)-alkylaminocarbonyl-($C_1$-$C_6$)-alkyl;
N—(($C_1$-$C_6$)-haloalkanoyl)-aminocarbonyl, mono-(($C_6$-$C_{14}$)-aryl)-aminocarbonyl, di-(($C_6$-$C_{14}$)-aryl)-aminocarbonyl;
($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy;
($C_3$-$C_8$)-cycloalkyl which may optionally be substituted in the cycloalkyl radical by ($C_1$-$C_6$)-alkyl and/or halogen; ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-haloalkyl, ($C_3$-$C_8$)-cycloalkyl-($C_1$-$C_6$)-alkoxy, ($C_3$-$C_8$)-cycloalkyl-($C_1$-$C_6$)-haloalkoxy, ($C_3$-$C5$)-cycloalkylcarbonyl, ($C_3$-$C_8$)-cycloalkoxycarbonyl, ($C_3$-$C_8$)-cycloalkyl-($C_1$-$C_6$)-alkylcarbonyl, ($C_3$-$C_8$)-cycloalkyl-($C_1$-$C_6$)-haloalkylcarbonyl, ($C_3$-$C_8$)-cycloalkyl-($C_1$-$C_6$)-alkoxycarbonyl, ($C_3$-$C_8$)-cycloalkyl-($C_1$-$C_6$)-haloalkoxycarbonyl, ($C_3$-$C_8$)-cycloalkylcarbonyloxy, ($C_3$-$C_8$)-cycloalkoxycarbonyloxy, ($C_3$-$C_8$)-cycloalkyl-($C_1$-$C_6$)-alkylcarbonyloxy, ($C_3$-$C_8$)-cycloalkyl-($C_1$-$C_6$)-haloalkylcarbonyloxy, ($C_3$-$C_8$)-cycloalkyl-($C_1$-$C_6$)-alkoxycarbonyloxy, ($C_3$-$C_8$)-cycloalkyl-($C_1$-$C_6$)-haloalkoxycarbonyloxy;
($C_3$-$C_8$)-cycloalkenyl, ($C_3$-$C_8$)-cycloalkenyloxy, ($C_3$-$C_8$)-cycloalkenyl-($C_1$-$C_6$)-alkyl, ($C_3$-$C_8$)-cycloalkenyl-($C_1$-$C_6$)-haloalkyl, ($C_3$-$C_8$)-cycloalkenyl-($C_1$-$C_6$)-alkoxy, ($C_3$-$C_8$)-cycloalkenyl-($C_1$-$C_6$)-haloalkoxy, ($C_3$-$C_8$)-cycloalkenylcarbonyl, ($C_3$-$C_8$)-cycloalkenyloxycarbonyl, ($C_3$-$C_8$)-cycloalkenyl-($C_1$-$C_6$)-alkylcarbonyl, ($C_3$-$C_8$)-cycloalkenyl-($C_1$-$C_6$)-haloalkylcarbonyl, ($C_3$-$C_8$)-cycloalkenyl-($C_1$-$C_6$)-alkoxycarbonyl, ($C_3$-$C_8$)-cycloalkenyl-($C_1$-$C_6$)-haloalkoxycarbonyl, ($C_3$-$C_8$)-cycloalkenylcarbonyloxy, ($C_3$-$C_8$)-cycloalkenyloxycarbonyloxy, ($C_3$-$C_8$)-cycloalkenyl-($C_1$-$C_6$)-alkylcarbonyloxy, ($C_3$-$C_8$)-cycloalkenyl-($C_1$-$C_6$)-haloalkylcarbonyloxy, ($C_3$-$C_8$)-cycloalkenyl-($C_1$-$C_6$)-alkoxycarbonyloxy, ($C_3$-$C_8$)-cycloalkenyl-($C_1$-$C_6$)-haloalkoxycarbonyloxy;
hydroxy-($C_1$-$C_6$)-alkyl, hydroxy-($C_1$-$C_6$)-alkoxy, cyano-($C_1$-$C_6$)-alkoxy, cyano-($C_1$-$C_6$)-alkyl;
($C_1$-$C_6$)-alkylsulfonyl, ($C_1$-$C_6$)-alkylthio, ($C_1$-$C_6$)-alkylsulfinyl, ($C_1$-$C_6$)-haloalkylsulfonyl, ($C_1$-$C_6$)-haloalkylthio, ($C_1$-$C_6$)-haloalkylsulfinyl, ($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl, ($C_1$-$C_6$)-alkylsulfonyloxy, ($C_1$-$C_6$)-haloalkylsulfonyloxy, ($C_1$-$C_6$)-alkylthiocarbonyl, ($C_1$-$C_6$)-haloalkylthiocarbonyl, ($C_1$-$C_6$)-alkylthiocarbonyloxy, ($C_1$-$C_6$)-haloalkylthiocarbonyloxy, ($C_1$-$C_6$)-alkylthio-($C_1$-$C_6$)-alkyl, ($C_1$-$C_6$)-alkylthio-($C_1$-$C_6$)-alkoxy, ($C_1$-$C_6$)-alkylthio-($C_1$-$C_6$)-alkylcarbonyl, ($C_1$-$C_6$)-alkylthio-($C_1$-$C_6$)-alkylcarbonyloxy; ($C_4$-$C_{14}$)-arylsulfonyl, ($C_6$-$C_{14}$)-arylthio, ($C_6$-$C_{14}$)-arylsulfinyl, ($C_3$-$C_8$)-cycloalkylthio, ($C_3$-$C_8$)-alkenylthio, ($C_3$-$C_8$)-cycloalkenylthio, and ($C_3$-$C_6$)-alkynylthio; and $R^1$ and $R^{2a}$ may be joined to one another via a bond so as to form, together with carbon 4 (or carbon 6) and 5 of the pyrimidine and the carbonyl group in the 5 position of the pyrimidine, a 5- to 7-membered partly hydrogenated carbo- or heterocycle which may also be substituted;

$R^3$ is selected from the group consisting of hydrogen, ($C_1$-$C_6$)-alkyl, ($C_1$-$C_6$)-alkoxy, ($C_1$-$C_6$)-alkoxy-($C_1$-$C_6$)-alkyl, ($C_1$-$C_6$)-alkoxycarbonyl and aminocarbonyl;

$R^4$ and $R^5$ are each independently selected from the group consisting of hydrogen, $(C_1\text{-}C_6)$-alkyl, $(C_1\text{-}C_6)$-haloalkyl, hydroxyl, $(C_1\text{-}C_6)$-alkoxy and $(C_1\text{-}C_6)$-haloalkoxy; or the $R^4$ and $R^5$ radicals together with the carbon atom to which they are bonded form a three- to seven-membered ring; and $R^6$ and $R^7$ are each independently selected from the group consisting of hydrogen, $(C_1\text{-}C_6)$-alkyl, $(C_1\text{-}C_6)$-haloalkyl, $(C_1\text{-}C_6)$-alkoxy, $(C_1\text{-}C_6)$-haloalkoxy, $(C_6\text{-}C_{14})$-aryl, $(C_6\text{-}C_{14})$-aryloxy, $(C_6\text{-}C_{14})$-arylcarbonyl and $(C_6\text{-}C_{14})$-aryloxycarbonyl; or the $R^6$ and $R^7$ radicals together form a $(C_1\text{-}C_7)$-alkylene group which may contain one or more oxygen and/or sulfur atoms, where the $(C_1\text{-}C_7)$-alkylene group may be mono- or polysubstituted by halogen and the respective halogen substituents may be the same or different, and n is 0, 1 or 2 and $R^8$, $R^9$, $R^{10}$ and $R^{11}$ are each independently selected from the group consisting of hydrogen, halogen, cyano, C(O)OH, C(O)NH$_2$, $(C_1\text{-}C_6)$-alkyl, $(C_1\text{-}C_6)$-alkylcarbonyl, $(C_1\text{-}C_6)$-alkyloxycarbonyl, $(C_1\text{-}C_6)$-alkylaminocarbonyl, $(C_1\text{-}C_6)$-dialkylaminocarbonyl, $(C_1\text{-}C_6)$-haloalkyl, $(C_1\text{-}C_6)$-alkoxy, $(C_1\text{-}C_6)$-haloalkoxy, $(C_2\text{-}C_6)$-alkenyl, $(C_2\text{-}C_6)$-alkynyl, $(C_2\text{-}C_6)$-haloalkynyl, $(C_2\text{-}C_6)$-alkynylcarbonyl, $(C_2\text{-}C_6)$-haloalkynylcarbonyl, $(C_2\text{-}C_6)$-alkynyloxy, $(C_2\text{-}C_6)$-haloalkynyloxy, $(C_2\text{-}C_6)$-alkynyloxycarbonyl and $(C_2\text{-}C_6)$-haloalkynyloxycarbonyl and nitro;

X is a bond, CH$_2$, O, S, carbonyl, NH, CR$^{12}$R$^{13}$ and NR$^{14}$ or CH$_2$O, CH$_2$S, where the carbon atom in the two latter groups is bonded to the aromatic moiety;

wherein if n is 0, X is not a bond; and $R^{12}$ and $R^{13}$ are each independently selected from the group consisting of hydrogen, $(C_1\text{-}C_6)$-alkyl and $(C_1\text{-}C_6)$-haloalkyl; and $R^{14}$ is selected from the group consisting of hydrogen, $(C_1\text{-}C_6)$-alkyl, $(C_1\text{-}C_6)$-haloalkyl;

said process comprising condensing an amidine of the (IV) type or an acid addition salt thereof

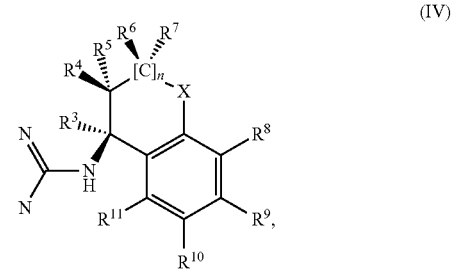

(IV)

wherein $R^3$, $R^4$, $R^5$, $R^6$, $R^7$, $R^8$, $R^9$, $R^{10}$, $R^{11}$, X and n are as defined above, with a ketone of formula (V)

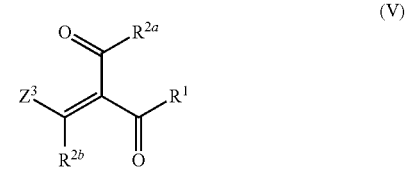

(V)

in which the $Z^3$ radical is a $(C_1\text{-}C_6)$-alkoxy or di-$(C_1\text{-}C_6)$-alkylamino, and $R^{2a}$, and $R^{2b}$ are as defined above.

* * * * *